United States Patent
Cheney

(10) Patent No.: US 10,851,148 B2
(45) Date of Patent: Dec. 1, 2020

(54) ANTIBODIES TO MICA AND MICB PROTEINS

(71) Applicant: Novelogics Biotechnology, Inc., Vancouver (CA)

(72) Inventor: Ian Wayne Cheney, Port Coquitlam (CA)

(73) Assignee: Novelogics Biotechnology, Inc., Vancouver (CA)

( * ) Notice: Subject to any disclaimer, the term of this patent is extended or adjusted under 35 U.S.C. 154(b) by 550 days.

(21) Appl. No.: 14/776,640

(22) PCT Filed: Mar. 15, 2014

(86) PCT No.: PCT/IB2014/001157
§ 371 (c)(1),
(2) Date: Sep. 14, 2015

(87) PCT Pub. No.: WO2014/140904
PCT Pub. Date: Sep. 18, 2014

(65) Prior Publication Data
US 2016/0046689 A1 Feb. 18, 2016

Related U.S. Application Data

(60) Provisional application No. 61/940,372, filed on Feb. 15, 2014, provisional application No. 61/801,329, filed on Mar. 15, 2013.

(51) Int. Cl.
| | | |
|---|---|---|
| C07K 16/28 | (2006.01) | |
| A61K 39/00 | (2006.01) | |
| C07K 14/705 | (2006.01) | |
| C07K 14/74 | (2006.01) | |

(52) U.S. Cl.
CPC ...... *C07K 14/705* (2013.01); *C07K 14/70539* (2013.01); *C07K 16/2833* (2013.01); *C07K 2317/30* (2013.01); *C07K 2317/56* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 7,563,450 B2 | 7/2009 | Cosman |
| 7,666,417 B2 | 2/2010 | Spies |
| 7,771,718 B2 | 8/2010 | Spies |
| 7,959,916 B2 | 6/2011 | Spies |
| 8,182,809 B1 | 5/2012 | Wu |
| 2003/0195337 A1 | 10/2003 | Cosman |
| 2005/0233391 A1 | 10/2005 | Spies |
| 2009/0274699 A1 | 11/2009 | Cosman |
| 2010/0111973 A1 | 5/2010 | Dranoff |
| 2010/0316650 A1 | 12/2010 | Spies |
| 2011/0311535 A1 | 12/2011 | Dranoff |
| 2011/0311561 A1 | 12/2011 | Martin |
| 2012/0295288 A1 | 11/2012 | Yu |
| 2014/0004112 A1 | 1/2014 | Wucherpfennig |
| 2014/0037630 A1 | 2/2014 | Dranoff |
| 2016/0030659 A1 | 2/2016 | Cheney |

FOREIGN PATENT DOCUMENTS

| | | |
|---|---|---|
| EP | 01949915 A2 | 7/2008 |
| WO | WO 98/019167 | 5/1998 |
| WO | WO 2003/089616 | 10/2003 |
| WO | WO 2006/024367 | 3/2006 |
| WO | WO 2008/036981 | 3/2008 |
| WO | WO 2013/117614 | 8/2013 |
| WO | WO 2013/117647 | 8/2013 |
| WO | WO 2014/140884 | 9/2014 |

OTHER PUBLICATIONS

Edwards et al (JMB, 2003, 334: 103-118).*
Lloyd et al (Protein Engineering, Eng. Design & Selection, 2009, 22(3): 159-168).*
Goel et al (J. Immunol., 2004, 173: 7358-7367).*
Khan and Salunke (J. Immunol, 2014, 192: 5398-5405).*
Poosarla et al (Biotechn. Bioeng., 2017, 114(6): 1331-1342).*
Torres and Casadevall (Trend. Immunol., 2008, 29(2): 91-97).*
Rudikoff et al (PNAS USA 1982, 79: 1979-1983) (Year: 1982).*
Vajdos et al (JMB, 2002, 320: 415-428) (Year: 2002).*
Holm et al (Mol. Immunol. 2007, 44: 1075-1084) (Year: 2007).*
De Pascalis et al (J. Immunol. 2002, 169: 3076-3084) (Year: 2002).*
Wu et al (J. Mol. Biol. 1999, 294: 151-162) (Year: 1999).*
Arreygue-Garcia et al., "Augmented serum level of major histocompatibility complex class I-related chain A (MICA) protein and reduced NKG2D expression on NK and T cells in patients with cervical cancer and precursor lesions," *BMC Cancer* 8:16 (2008).
Ashiru et al., "Natural Killer Cell Cytotoxicity Is Suppressed by Exposure to the Human NKG2D Ligand MICA*008 That Is Shed by Tumor Cells in Exosomes," *Cancer Res.* 70(2):481-9 (2010).
Bahram et al., "A second lineage of mammalian major histocompatbility complex class I genes," *Proc Nat'l Acad Sci USA.* 91:6259-63 (1994).

(Continued)

Primary Examiner — G. R. Ewoldt
Assistant Examiner — Marianne DiBrino
(74) Attorney, Agent, or Firm — Dechert LLP

(57) ABSTRACT

MICA and MICB are expressed on the surface of stressed, virus infected and cancer cells; they bind to their common receptor NKG2D on immune effector cells such as natural killer (NK) cells and some T cells to signal immune responses, including cytotoxicity, towards cells expressing surface MICA or MICB. To evade this immune-surveillance, virus infected cells and cancer cells shed the extracellular domain of their MICA and MICB as soluble forms (sMICA and sMICB) which act as decoys by binding and down-regulating expression of NKG2D on the immune effector cells. Antibodies are provided that specifically bind the soluble forms of both MICA and MICB to inhibit their adverse effects, but do not bind cell- or membrane-bound MICA and MICB to preserve their beneficial immune effects.

3 Claims, 15 Drawing Sheets

Specification includes a Sequence Listing.

(56) References Cited

OTHER PUBLICATIONS

Bahram et al., "Nucleotide sequence of the human MHC class I MCA gene," *Immunogenetics* 44:80-81 (1996).
Bahram et al., "Nucleotide sequence of a human MHC class I MICB cDNA," *Immunogenetics* 43:230-233 (1996).
Barlow et al., "Continuous and discontinuous antigenic determinants," *Nature* 322:747-748 (1986).
Bauer et al., "Expression and purification, crystallization and crystallographic characterization of the human MHC class 1 related protein MICA," *Acta Cryst* D54:451-453 (1998).
Bauer et al., "Activation of NK Cells and T Cells by NKG2D, a Receptor for Stress-Inducible MICA," *Science* 285(5428):727-9 (1999).
Boissel et al., "BCR/ABL Oncogene Directly Controls MHC Class I Chain-Related Molecule A Expression in Chronic Myelogenous Leukemia," *J Immunol.* 176(8):5108-5116 (2006).
Bonnafous et al., "Targeting MICA with therapeutic antibodies for the treatment of cancer," *J ImmunoTherapy Cancer* 1(Suppl 1):p. 41 (2013).
Bonnafous et al., "Targeting MICA with therapeutic antibodies for the treatment of cancer," Innate Pharma Poster Presentation (2013).
Cao et al., "RAET1E2, a Soluble Isoform of the UL16-binding Protein RAET1E Produced by Tumor Cells, Inhibits NKG2D-mediated NK," Cytotoxicity, *J Biol Chem.* 282(26):18922-18928 (2007).
Chai, J-G., "Mechanisms of endogenous MHC class II presentation by tumor cells," *Immunotherapy* 4(8):777-779 (2012).
Chalupny et al., "Down-regulation of the NKG2D ligand MICA by the human cytomegalovirus glycoprotein UL142," *Biochem Biophys Res Commun.* 346(1):175-81 (2006).
Chang et al., "Secretome-Based Identification of ULBP2 as a Novel Serum Marker for Pancreatic Cancer Detection," *PLoS One* 6(5):e20029 (2011).
Chen et al., "Soluble TNF-a Receptors Are Constitutively Shed and Downregulates Adhresion Molecule Expression in Malignant Gliomas," *J Neuropathol Exp Neurol.* 56(5):541-550 (1997).
Doubrovina et al., "Evasion from NK Cell Immunity by MHC Class I Chain-Related Molecules Expressing Colon Adenocarcinoma," *J Immunol.* 171:6891-6899 (2003).
Champsaur et al., "Effect of NKG2D ligand expression on host immune responses," *Immunol Rev.* 235(1): 267-285 (2010).
Eisele et al., "TGF-β and metalloproteinases differentially suppress NKG2D ligand surface expression on malignant glioma cells," *Brain* 129:2416-2425 (2006).
Fodil et al., "Allelic repertoire of the human MHC class I MICA gene," *Immunogenetics* 44:351-357 (1996).
Frigoul et al., "MICA: Standardized IMGT allele nomenclature, polymorphisms and diseases," *Recent Res Devel Human Genet.* 3:95-145 (2005).
Gatanaga et al., "Purification and characterization of an inhibitor (soluble necrosis factor receptor) for tumor necrosis factor and lymphotoxin obtained from the serum ultrafiltrates of human cancer patients," *Proc Natl Acad Sci USA.* 87:8781-8784 (1990).
Groh et al., "Broad tumor-associated expression and recognition by tumor-derived γδ T cells of MICA and MICB," *Proc Nat'l Acad Sci USA.* 96:6879-6884 (1999).
Groh et al., "Tumour-derived soluble MIC ligands impair expression of NKG2D and T-cell activation," *Nature* 419:734-8 (2002).
Groh et al., "Fas-ligand-mediated paracrine T cell regulation by the receptor NKG2D in tumor immunity," *Nat Immunol.* 7:755-62 (2006).
Hilpert et al., "Comprehensive Analysis of NKG2D Ligand Expression and Release in Leukemia: Implications for NKG2D-Mediated NK Cell Responses," J Immunol. 1360-1371 (2012).
Holdenreider et al, "Soluble MICA in malignant diseases," *Int'l J Cancer* 118:684-687 (2005).
Holmes et al., "Structural Studies of Allelic Diversity of the MHC Class I Homolog MIC-B, a Stress-Inducible Ligand for the Activating Immunoreceptor NKG2D," *J Immunol* 169:1395-400 (2002).
Hue et al, "Potential Role of NKG2D/MHC Class I-Related Chain A Interaction in Intrathymic Maturation of Single-Positive CD8 T Cells," *J Immunol.* 171:1909-1917 (2003).
Hue S, et al., "A Direct Role for NKG2D/MICA Interaction in Villous Atrophy during Celiac Disease," *Immunity* 21:367-377 (2004).
Jimenez-Perez et al., "Cervical cancer cell lines expressing NKG2Dligands are able to down-modulate the NKG2D receptor on NKL cells with functional implications," *BMC Immunology* 13:7 (2012).
Jinushi et al., "Therapy-induced antibodies to MHC class I chain-related protein A antagonize immune suppression and stimulate antitumor cytotoxicity," *Proc Natl Acad Sci USA.* 103(24):9190-9195 (2006).
Jinushi et al., "MHC class I chain-related protein A antibodies and shedding are associated with the progression of multiple myeloma," *Proc Natl Acad Sci USA.* 105(4): 1285-1290 (2008).
Jonjic et al., "Immune evasion of natural killer cells by viruses," *Curr Opin Immunol.* 20(1):30-8 (2008).
Kaiser et al., "Disulphide-isomerase-enabled shedding of tumour-associated NKG2D ligands," *Nature* 447(7143):482-6 (2007).
Kong et al., "The NKG2D ligand ULBP4 binds to TCRγ9/δ2 and induces cytotoxicity to tumor cells through both TCRγδ and NKG2D2009," *Blood* 114(2):310-17 (2009).
Kringelum et al., "Reliable B Cell Epitope Predictions: Impacts of Method Development and Improved Benchmarking," *PLoS Computational Biol.* 8(12):e1002829 (2012).
Kumar et al., Soluble MICA and a MICA Variation as Possible Prognostic Biomarkers for HBV-Induced Hepatocellular Carcinoma,, *PLoS One* 7(9):1-6 e44743 (2012).
Leelayuwat et al., "A new polymorphic and multicopy MHC gene family related to nonmammalian class I," *Immunogenetics* 40:339-351 (1994).
Li et al., "Crystal Structure of the MHC Class I Homolog MIC-A, a γδ T Cell Ligand," *Immunity* 10:577-84 (1999).
Li et al., "Complex structure of the activating immunoreceptor NKG2D and its MHC class I-like ligand MICA," *Nature Immunol.* 2(5):443-451 (2001).
Li et al., "Clinical significance of the NKG2D ligands, MICA/B and ULBP2 in ovarian cancer: high expression of ULBP2 is an indicator of poor prognosis," *Cancer Immunol Immunother.* 58(5):641-52 (2009).
Liu, et al., "Perturbation of NK cell peripheral homeostasis accelerates prostate carcinoma metastasis," *J Clin Invest.* 123(10):4410-4422 (2013).
Matusali et al., "Soluble ligands for the NKG2D receptor are released during HIV-1 infection and impair NKG2D expression and cytotoxicity of NK cells," *FASEB J.* 27(6):2440-50 (2013).
McFarland et al., "Symmetry Recognizing Asymmetry: Analysis of the Interactions between the C-Type Lectin-like Immunoreceptor NKG2D and MHC Class I-like Ligands," *Structure* 11:411-422 (2003).
Muller et al., "Structure of the HCMV UL16-MICB Complex Elucidates Select Binding of a Viral Immunoevasin to Diverse NKG2D Ligands," *PLoS Pathogens* 6(1):e1000723 (2010).
Nolting et al., "MHC class I chain-related protein A shedding in chronic HIV-1 infection is associated with profound NK cell dysfunction," *Virology* 406:12-20 (2010).
Ohashi et al., "Post-translational Modification of the NKG2D Ligand RAET1G Leads to Cell Surface Expression of a Glycosylphosphatidylinositol-linked Isoform," *J Biol Chem.* 285(22):16408-16415 (2010).
Onda et al., "A novel secreted tumor antigen with a glycosylphosphatidylinositol anchored structure ubiquitously expressed in human cancers," *Biochem Biophys Res Commun.* 285(2):235-43 (2001).
Panter et al., "Dynamics of Major Histocompatibility Complex Class I Association with the Human Peptide-loading Complex," *J Biol Chem.* 287(37):31172-31184 (2012).
Paschen et al., "Differential Clinical Significance of Individual NKG2D Ligands in Melanoma: Soluble ULBP2 as an Indicator of Poor Prognosis Superior to S100B," *Clin Cancer Res.* 15(16):5208-5215 (2009).

(56) References Cited

OTHER PUBLICATIONS

Raffaghello et al., "Downregulation and/or Release of NKG2D Ligands as Immune Evasion Strategy of Human Neuroblastoma," *Neoplasia* 6(5):558-568 (2004).
Rebmann et al., "Soluble MICA as an independent prognostic factor for the overall survival and progression-free survival of multiple myeloma patients," *Clin Immunol.* 123(1):114-20 (2007).
Radosavljevic et al., "A cluster of ten novel MHC class I related genes on human chromosome 6q24.2-q25.3," *Genomics* 79:114-23 (2002).
Robinson et al., "IMGT/HLA and IMGT/MHC: Sequence databases for the study of the major histocompatibility complex," *Nucleic Acids Res.* 31:311-314 (2003).
Salih et al., "Functional expression and release of ligands for the activating immunoreceptor NKG2D in leukemia," *Blood* 102(4):1389-96 (2003).
Salih et al., "Cutting Edge: Down-Regulation of MICA on Human Tumors by Proteolytic Shedding," *J Immunol.* 169:4098-102 (2002).
Schneider et al., "The Human Herpesvirus-7 (HHV-7) U21 Immunoevasin Subverts NK-Mediated Cytotoxicity through Modulation of MICA and MICB," *PLoS Pathogens*, 7(11):e1002362 (2011).
Song et al., "Soluble ULBP suppresses natural killer cell activity via down-regulating NKG2D expression," *Cell Immunol.* 239(1):22-30 (2006).
Steinle et al., "Diversification, expression, and γδ T cell recognition of evolutionarily distant members of the MIC family of major histocompatibility complex class I-related molecules," *Proc. Natl. Acad. Sci. USA.* 95:12510-12515, (1998).
Steinle et al., "Interactions of human NKG2D with its ligands MICA, MICB, and homologs of the mouse RAE-1protein family," *Immunogenectics* 53:279±287, (2001).
Sutherland et al., "The UL16-binding proteins, a novel family of MHC class I-related ligands for NKG2D, activate natural killer cell functions," *Immunol Rev.* 181:185-92 (2001).
Testa et al., "MHC Class I-Presented T Cell Epitopes Identified by Immunoproteomics Analysis Are Targets for a Cross Reactive Influenza-Specific T Cell Response," *PLoS ONE* 7(11):e48484 (2012).
Thibodeau et al., "Targeting the MHC Class II antigen presentation pathway in cancer immunotherapy," *Oncoimmunology* 1(6):908-916 (2012).
Waldhauer et al., "Tumor-Associated MICA Is Shed by ADAM Proteases," *Cancer Res* 68(15): 6368-6376 (2008).
Wang et al., "An Six-Amino Acid Motif in the α3 domain of MICA Is the Cancer Therapeutic Target to Inhibit Shedding," *Biochem Biophys Res Commun.* 387(3): 476-481 (2009).
Welte et al., "Selective intracellular retention of virally induced NKG2D ligands by the human cytomegalovirus UL16 glycoprotein," *Eur. J. Immunol.* 33:194-203 (2003).
Wu et al., "Prevalent expression of the immunostimulatory MHC class I chain-related molecule is counteracted by shedding in prostate cancer," *J Clin Invest.* 114:560-8 (2004).
Wu et al., "Obstructing Shedding of the Immune Stimulatory MICB Prevents Tumor Formation: Implication for Targeted Cancer Therapy," *Clin Cancer Res.* 15(2): 632-640 (2009).
Zou et al., "MICA is a Target for Complement-Dependent Cytotoxicity With Mouse Monoclonal Antibodies and Human Alloantibodies," *Human Immunology* 63:30-39 (2002).
Zdrenghea et al., "RSV infection modulates IL-15 production and MICA levels in respiratory epithelial cells," *Immunogenetics* 47:139-41 (1998).
Zwirner et al., "Identification of MICA as a New Polymorphic Alloantigen Recognized by Antibodies in Sera of Organ Transplant Recipients." *Human Immunology* 61:917-924 (2000).
Zwirner et al., "Immunobiology of the human MHC class I chain-related gene A (MICA): from transplantation immunology to tumor immune escape." *Eur Respir J.* 39:712-20 (2012).
International Preliminary Report on Patentability for PCT/IB2014/001157, dated Sep. 15, 2015.
International Search Report by the International Searching Authority for PCT/IB2014/001157 dated Oct. 15, 2014.

\* cited by examiner

```
  1 MGLGPVFLLL AGIFPFAPPG AAAEPHSLRY NLTVLSWDGS VQSGFLTEVH LDGQPFLRCD
 61 RQKCRAKPQG QWAEDVLGNK TWDRETRDLT GNGKDLRMTL AHIKDQKEGL HSLQEIRVCE
121 IHEDNSTRSS QHFYYDGELF LSQNLETKEW TMPQSSRAQT LAMNVRNFLK EDAMKTKTHY
181 HAMHADCLQE LRRYLKSGVV LRRTVPPMVN VTRSEASEGN ITVTCRASGF YPWNITLSWR
241 QDGVSLSHDT QQWGDVLPDG NGTYQTWVAT RICQGEEQRF TCYMEHSGNH STHPVPSGKV
301 LVLQSHWQTF HVSAVAAAAI FVIIIFYVRC CKKKTSAAEG PELVSLQVLD QHPVGTSDHR
361 DATQLGFQPL MSDLGSTGST EGA  (SEQ ID NO:1)
```

FIG._1A

```
  1 MGLGRVLLFL AVAFPFAPPA AAAEPHSLRY NLMVLSQDES VQSGFLAEGH LDGQPFLRYD
 61 RQKRRAKPQG QWAEDVLGAK TWDTETEDLT ENGQDLRRTL THIKDQKGGL HSLQEIRVCE
121 IHEDSSTRGS RHFYYDGELF LSQNLETQES TVPQSSRAQT LAMNVTNFWK EDAMKTKTHY
181 RAMQADCLQK LQRYLKSGVA IRRTVPPMVN VTCSEVSEGN ITVTCRASSF YPRNITLTWR
241 QDGVSLSHNT QQWGDVLPDG NGTYQTWVAT RIRQGEEQRF TCYMEHSGNH GTHPVPSGKV
301 LVLQSQRTDF PYVSAAMPCF VIIIILCVPC CKKKTSAAEG PELVSLQVLD QHPVGTGDHR
361 DAAQLGFQPL MSATGSTGST EGA  (SEQ ID NO:2)
```

FIG._1B

MICA alpha-3 domain: residues 205-297

```
205_VPPMVNVTRSEASEGNITVTCRASGFYPWNITLSWRQDGVSLSHDTQQWGDVLPDGNGTYQT
WVATRICQGEEQRFTCYMEHSGNHSTHPVPS_297  (SEQ ID NO:3)
```

FIG._1C

MICB alpha-3 domain: residues 205-297

```
205_VPPMVNVTCSEVSEGNITVTCRASSFYPRNITLTWRQDGVSLSHNTQQWGDVLPDGNGTYQT
WVATRIRQGEEQRFTCYMEHSGNHGTHPVPS_297  (SEQ ID NO:4)
```

FIG._1D

Human MICA cDNA

```
   1 cactgcttga gccgctgaga gggtggcgac gtcggggcca tggggctggg cccggtcttc
  61 ctgcttctgg ctggcatctt ccctttttgca cctccgggag ctgctgctga gccccacagt
 121 cttcgttata acctcacggt gctgtcctgg gatggatctg tgcagtcagg gtttctcact
 181 gaggtacatc tggatggtca gcccttcctg cgctgtgaca ggcagaaatg cagggcaaag
 241 ccccagggac agtgggcaga agatgtcctg ggaaataaga catgggacag agagaccaga
 301 gacttgacag ggaacggaaa ggacctcagg atgaccctgg ctcatatcaa ggaccagaaa
 361 gaaggcttgc attccctcca ggagattagg gtctgtgaga tccatgaaga caacagcacc
 421 aggagctccc agcatttcta ctacgatggg gagctcttcc tctcccaaaa cctggagact
 481 aaggaatgga caatgcccca gtcctccaga gctcagacct tggccatgaa cgtcaggaat
 541 ttcttgaagg aagatgccat gaagaccaag acacactatc acgctatgca tgcagactgc
 601 ctgcaggaac tacggcgata tctaaaatcc ggcgtagtcc tgaggagaac agtgcccccc
 661 atggtgaatg tcacccgcag cgaggcctca gagggcaaca ttaccgtgac atgcagggct
 721 tctggcttct atccctggaa tatcacactg agctggcgtc aggatggggt atctttgagc
 781 cacgacaccc agcagtgggg ggatgtcctg cctgatggga atggaaccta ccagacctgg
 841 gtggccacca ggatttgcca aggagaggag cagaggttca cctgctacat ggaacacagc
 901 gggaatcaca gcactcaccc tgtgccctct gggaaagtgc tggtgcttca gagtcattgg
 961 cagacattcc atgtttctgc tgttgctgct gctgctattt ttgttattat tattttctat
1021 gtccgttgtt gtaagaagaa aacatcagct gcagagggtc cagagctcgt gagcctgcag
1081 gtcctggatc aacacccagt tgggacgagt gaccacaggg atgccacaca gctcggattt
1141 cagcctctga tgtcagatct tgggtccact ggctccactg agggcgccta gactctacag
1201 ccaggcagct gggattcaat tccctgcctg gatctcacga gcactttccc tcttggtgcc
1261 tcagtttcct gacctatgaa acagagaaaa taaaagcact tatttattgt tgttggaggc
1321 tgcaaaatgt tagtagatat gaggcgtttg cagctgtacc atatt   (SEQ ID NO:5)
```

FIG. 2

Human MICB cDNA

```
   1 gggccatggg gctgggccgg gtcctgctgt ttctggccgt cgccttccct tttgcacccc
  61 cggcagccgc cgctgagccc cacagtcttc gttacaacct catggtgctg tcccaggatg
 121 aatctgtgca gtcagggttt ctcgctgagg gacatctgga tggtcagccc ttcctgcgct
 181 atgacaggca gaaacgcagg gcaaagcccc agggacagtg ggcagaagat gtcctgggag
 241 ctaagacctg ggacacagag accgaggact tgacagagaa tgggcaagac ctcaggagga
 301 ccctgactca tatcaaggac cagaaggag gcttgcattc cctccaggag attagggtct
 361 gtgagatcca tgaagacagc agcaccaggg gctcccggca tttctactac gatggggagc
 421 tcttcctctc ccaaaacctg gagactcaag aatcgacagt gccccagtcc tccagagctc
 481 agaccttggc tatgaacgtc acaaatttct ggaaggaaga tgccatgaag accaagacac
 541 actatcgcgc tatgcaggca gactgcctgc agaaactaca gcgatatctg aaatccgggg
 601 tggccatcag gagaacagtg cccccatgg tgaatgtcac ctgcagcgag gtctcagagg
 661 gcaacatcac cgtgacatgc agggcttcca gcttctatcc ccggaatata cactgacct
 721 ggcgtcagga tggggtatct ttgagccaca cacccagca gtgggggat gtcctgcctg
 781 atgggaatgg aacctaccag acctgggtgg ccaccaggat cgccaagga gaggagcaga
 841 ggttcacctg ctacatggaa cacagcggga atcacggcac tcaccctgtg ccctctggga
 901 aggtgctggt gcttcagagt caacggacag actttccata tgtttctgct gctatgccat
 961 gtttgttat tattattat ctctgtgtcc cttgttgcaa gaagaaaaca tcagcggcag
1021 agggtccaga gcttgtgagc ctgcaggtcc tggatcaaca cccagttggg acaggagacc
1081 acagggatgc agcacagctg ggatttcagc ctctgatgtc agctactggg tccactggtt
1141 ccactgaggg cgcctagact ctacagccag gcggccagga ttcaactccc tgcctggatc
1201 tcaccagcac tttccctctg tttcctgacc tatgaaacag aaaataacat cacttattta
1261 ttgttgttgg atgctgcaaa gtgttagtag gtatgaggtg tttgctgctc tgccacgtag
1321 agagccagca aagggatcat gaccaactca acattccatt ggaggctata tgatcaaaca
1381 gcaaattgtt tatcatgaat gcaggatgtg ggcaaactca cgactgctcc tgccaacaga
1441 aggtttgctg agggcattca ctccatggtg ctcattggag ttatctactg ggtcatctag
1501 agcctattgt ttgaggaatg cagtcttaca agcctactct ggacccagca gctgactcct
1561 tcttccaccc ctcttcttgc tatctcctat accaataaat acgaagggct gtggaagatc
1621 agagcccttg ttcacgagaa gcaagaagcc ccctgacccc ttgttccaaa tatactcttt
1681 tgtctttctc tttattccca cgttcgccct tgttcagtc caatacaggg ttgtggggcc
1741 cttaacagtg ccatattaat tggtatcatt atttctgttg ttttgtttt tgttttgtt
1801 tttgttttg agacagagtc tcactcgtca cccaggctgc agttcactgg tgtgatctca
1861 gctcactgca acctctgcct cccaggttca agcacttctc gtacctcaga ctcccgatag
1921 ctgggattac agacaggcac caccacaccc agctaatttt tgtatttttt gtagagacgg
1981 ggtttcgcca agttgaccag cccagtttca aactcctgac ctcaggtgat ctgcctgcct
2041 tggcatccca aagtgctggg attacaagaa tgagccaccg tgcctggcct attttattat
2101 attgtaatat attttattat attagccacc atgcctgtcc tattttctta tgttttaata
```

FIG._3

```
2161 tattttaata tattacatgt gcagtaatta gattatcatg ggtgaacttt atgagtgagt
2221 atcttggtga tgactcctcc tgaccagccc aggaccagct ttcttgtcac cttgaggtcc
2281 cctcgccccg tcacaccgtt atcgattact ctgtgtctac tattatgtgt gcataattta
2341 taccgtaaat gtttactctt taaataaaaa aaaaaaaaaa (SEQ ID NO:6)
```

```
  1  EPHSLRYNLT VLSWDGSVQS GFLTEVHLDG QPFLRCDRQK CRAKPQGQWA EDVLGNKTWD
 61  RETRDLTGNG KDLRMTLAHI KDQKEGLHSL QEIRVCEIHE DNSTRSSQHF YYDGELFLSQ
121  NLETKEWTMP QSSRAQTLAM NVRNFLKEDA MKTKTHYHAM HADCLQELRR YLKSGVVLRR
181  TVPPMVNVTR SEASEGNITV TCRASGFYPW NITLSWRQDG VSLSHDTQQW GDVLPDGNGT
241  YQTWVATRIC QGEEQRFTCY MEHSGNHSTH PVPS (SEQ ID NO:7)
```

B.

```
  1  EPHSLRYNLT VLSWDGSVQS GFLTEVHLDG QPFLRCDRQK CRAKPQGQWA EDVLGNKTWD
 61  RETRDLTGNG KDLRMTLAHI KDQKEGLHSL QEIRVCEIHE DNSTRSSQHF YYDGELFLSQ
121  NLETEEWTMP QSSRAQTLAM NVRNFLKEDA MKTKTLYHAM HADCLQELRR YLKSGVVLRR
181  TVPPMVNVTR SEASEGNITV TCRASGFYPW NITLSWRQDG VSLSHDTQQW GDVLPDGNGT
241  YQTWVATRIC QGEEQRFTCY MEHSGNHSTH PVPS (SEQ ID NO:8)
```

C.

```
  1  EPHSLRYNLT VLSWDGSVQS GFLAEVHLDG QPFLRCDRQK CRAKPQGQWA EDVLGNKTWD
061  RETRDLTGNG KDLRMTLAHI KDQKEGLHSL QEIRVCEIHE DNSTRSSQHF YYDGELFLSQ
121  NLETEEWTMP QSSRAQTLAM NIRNFLKEDA MKTKTHYHAM HADCLQELRR YLKSGVVLRR
161  TVPPMVNVTR SEASEGNITV TCRASGFYPW NITLSWRQDG VSLSHDTQQW GDVLPDGNGT
241  YQTWVATRIC QGEEQRFTCY MEHSGNHSTH PVPS (SEQ ID NO:9)
```

D.

```
  1  EPHSLPYNLT VLSWDGSVQS GFLAEVHLDG QPFLRYDRQK CRAKPQGQWA EDVLGNKTWD
 61  RETRDLTGNG KDLRMTLAHI KDQKEGLHSL QEIRVCEIHE DNSTRSSQHF YYDGELFLSQ
121  NLETEEWTMP QSSRAQTLAM NVRNFLKEDA MKTKTHYHAM HADCLQELRR YLKSGVVLRR
181  TVPPMVNVTR SEASEGNITV TCRASGFYPW NITLSWRQDG VSLSHDTQQW GDVLPDGNGT
241  YQTWVATRIC QGEEQRFTCY MEHSGNHSTH PVPS (SEQ ID NO:10)
```

E.

```
  1  EPHSLRYNLT VLSWDGSVQS GFLAEVHLDG QPFLRYDRQK CRAKPQGQWA EDVLGNKTWD
 61  RETRDLTGNG KDLRMTLAHI KDQKEGLHSL QEIRVCEIHE DNSTRSSQHF YYDGELFLSQ
121  NLETEEWTVP QSSRAQTLAM NVRNFLKEDA MKTKTHYHAM HADCLQELRR YLESGVVLRR
181  TVPPMVNVTR SEASEGNITV TCRASSFYPR NITLTWRQDG VSLSHDTQQW GDVLPDGNGT
241  YQTWVATRIC QGEEQRFTCY MEHSGNHSTH PVPS (SEQ ID NO:11)
```

F.

```
  1  EPHSLRYNLT VLSWDGSVQS GFLTEVHLDG QPFLRCDRQK CRAKPQGQWA EDVLGNKTWD
 61  RETRDLTGNG KDLRMTLAHI KDQKEGLHSL QEIRVCEIHE DNSTRSSQHF YYDGELFLSQ
121  NLETEEWTMP QSSRAQTLAM NVRNFLKEDA MKTKTHYHAM HADCLQELRR YLKSGVVLRR
181  TVPPMVNVTR SEASEGNITV TCRASGFYPW NITLSWRQDG VSLSHDTQQW GDVLPDGNGT
241  YQTWVATRIC QGEEQRFTCY MEHSGNHSTH PVPS (SEQ ID NO:12)
```

```
  1  EPHSLRYNLT VLSWDGSVQS GFLAEVHLDG QPFLRCDRQK CRAKPQGQWA EDVLGNKTWD
 61  RETRDLTGNG KDLRMTLAHI KDQKEGLHSL QEIRVCEIHE DNSTRSSQHF YYDGELFLSQ
121  NLETEEWTMP QSSRAQTLAM NVRNFLKEDA MKTKTHYHAM HADCLQELRR YLKSGVVLRR
181  TVPPMVNVTR SEASEGNITV TCRASGFYPW NITLSWRQDG VSLSHDTQQW GDVLPDGNGT
241  YQTWVATRIC QGEEQRFTCY MEHSGNHSTH PVPS (SEQ ID NO:13)
```

H.

```
  1  EPHSLRYNLT VLSWDGSVQS GFLTEVHLDG QPFLRCDRQK CRAKPQGQWA EDVLGNKTWD
 61  RETRDLTGNG KDLRMTLAHI KDQKEGLHSL QEIRVCEIHE DNSTRSSQHF YYDGELFLSQ
121  NLETKEWTMP QSSRAQTLAM NVRNFLKEDA MKTKTHYHAM HADCLQELRR YLKSGVVLRR
181  TVPPMVNVTR SEASEGNITV TCRASGFYPW NITLSWRQDG VSLSHDTQQW GDVLPDGNGT
241  YQTWVATRIC QGEEQRFTCY MEHSGNHSTH PVPSGK (SEQ ID NO:14)
```

*FIG_4 (cont'd)*

A.

```
  1  EPHSLRYNLM VLSQDESVQS GFLAEGHLDG QPFLRYDRQK RRAKPQGQWA EDVLGAKTWD
 61  TETEDLTENG QDLRRTLTHI KDQKGGLHSL QEIRVCEIHE DSSTRGSRHF YYDGELFLSQ
121  NLETQESTVP QSSRAQTLAM NVTNFWKEDA MKTKTHYRAM QADCLQKLQR YLKSGVAIRR
181  TVPPMVNVTC SEVSEGNITV TCRASSFYPR NITLTWRQDG VSLSHNTQQW GDVLPDGNGT
241  YQTWVATRIR QGEEQRFTCY MEHSGNHGTH PVPS  (SEQ ID NO:15)
```

B.

```
  1  PHSLRYNLMV LSQDGSVQSG FLAEGHLDGQ PFLRYDRQKR RAKPQGQWAE DVLGAKTWDT
 61  ETEDLTENGQ DLRRTLTHIK DQKGGLHSLQ EIRVCEIHED SSTRGSRHFY YDGELFLSQN
121  LETQESTVPQ SSRAQTLAMN VTNFWKEDAM KTKTHYRAMQ ADCLQKLQLP PMVNVICSEV
181  SEGNITVTCR ASSFYPRNIT LTWRQDGVSL SHNTQQWGDV LPDGNGTYQT WVATRIRQGE
241  EQRFTCYMEH SGNHGTHPVP SGKALVLQSQ RTDFP  (SEQ ID NO:16)
```

C.

```
  1  PHSLRYNLMV LSQDGSVQSG FLAEGHLDGQ PFLRYDRQKR RAKPQGQWAE DVLGAETWDT
 61  ETEDLTENGQ DLRRTLTHIK DQKGGLHSLQ EIRVCEMHED SSTRGSRHFY YNGELFLSQN
121  LETQESTVPQ SSRAQTLAMN VTNFWKEDAM KTKTHYRAMQ ADCLQKLQRY LKSGVAIRRT
181  VPPMVNVTCS EVSEGNITVT CRASSFYPRN ITLTWRQDGV SLSHNTQQWG DVLPDGNGTY
241  QTWVATRIRQ GEEQRFTCYM EHSGNHGTHP VPS  (SEQ ID NO:17)
```

D.

```
  1  PHSLRYNLMV LSQDGSVQSG FLAEGHLDGQ PFLRYDRQKR RAKPQGQWAE DVLGAKTWDT
 61  ETEDLTENGQ DLRRTLTHIK DQKGGLHSLQ EIRVCEIHED SSTRGSRHFY YDGELFLSQN
121  LETQESTVPQ SSRAQTLAMN VTNFWKEDAM KTKTHYRAMQ ADCLQKLQRY LKSGVAIRRT
181  VPPMVNVICS EVSEGNITVT CRASSFYPRN ITLTWRQDGV SLSHNTQQWG DVLPDGNGTY
241  QTWVATRIRQ GEEQRFTCYM EHSGNHGTHP VPS  (SEQ ID NO:18)
```

E.

```
  1  PHSLRYNLMV LSQDGSVQSG FLAEGHLDGQ PFLRYDRQKR RAKPQGQWAE NVLGAKTWDT
 61  ETEDLTENGQ DLRRTLTHIK DQKGGLHSLQ EIRVCEIHED SSTRGSRHFY YDGELFLSQN
121  LETQESTVPQ SSRAQTLAMN VTNFWKEDAM KTKTHYRAMQ ADCLQKLQRY LKSGVAIRRT
181  VPPMVNVTCS EVSEGNITVT CRASSFYPRN ITLTWRQDGV SLSHNTQQWG DVLPDGNGTY
241  QTWVATRIRQ GEEQRFTCYM EHSGNHGTHP VPS  (SEQ ID NO:19)
```

FIG_5

F.

```
  1  PHSLRYNLMV LSQDGSVQSG FLAEGHLDGQ PFLRYDRQKR RAKPQGQWAE DVLGAETWDT
 61  ETEDLTENGQ DLRRTLTHIK DQKGGLHSLQ EIRVCEIHED SSTRGSRHFY YNGELFLSQN
121  LETQESTVPQ SSRAQTLAMN VTNFWKEDAM KTKTHYRAMQ ADCLQKLQRY LKSGVAIRRT
181  VPPMVNVTCS EVSEGNITVT CRASSFYPRN ITLTWRQDGV SLSHNTQQWG DVLPDGNGTY
241  QTWVATRIRQ GEEQKFTCYM EHSGNHGTHP VPS (SEQ ID NO:20)
```

G.

```
  1  PHSLRYNLMV LSQDGSVQSG FLAEGHLDGQ PFLRYDRQKR RAKPQGQWAE DVLGAETWDT
 61  ETEDLTENGQ DLRRTLTHIK DQKGGLHSLQ EIRVCEIHED SSTRGSRHFY YNGELFLSQN
121  LETQESTVPQ SSRAQTLAMN VTNFWKEDAM KTKTHYRAMQ ADCLQKLQRY LKSGVAIRRT
181  VPPMVNVTCS EVSEGNITVT CRASSFYPRN ITLTWRQDGV SLSHNTQQWG DVLPDGNGTY
241  QTWVATRIRQ GEEQRFTCYM EHSGNHGTHP VPS (SEQ ID NO:21)
```

*FIG_5 (cont'd)*

A.

*METDTLLLWVLLLWVPGSAG*DIVLTQSPASLAVSLGQRATISCRASKSVSTSGYSYMHWYQQKPGQ
PPKLLIYRASNLESGVPARFSGSGSGTDFTLNIHPVEEEDAATYYCQHSRELPLTFGAGTKLELKR
ADAAPTVSIFPPSSEQLTSGG
(SEQ ID NO:22)

B.

```
                        CDR L1                         CDR L2
DIVLTQSPASLAVSLGQRATISCRASKSVSTSGYSYMHWYQQKPGQPPKLLIYRASNLESGV
                                CDR L3
PARFSGSGSGTDFTLNIHPVEEEDAATYYCQHSRELPLTFGAGTKLELKR
```
(SEQ ID NO:23)

C.

```
ATGGAGACAG ACACACTCCT GTTATGGGTA CTGCTGCTCT GGGTTCCAGG TTCCGCTGGT
GACATTGTGC TGACACAGTC TCCTGCTTCC TTAGCTGTAT CTCTGGGGCA GAGGGCCACC
ATCTCATGCA GGGCCAGCAA GAGTGTCAGT ACATCTGGCT ATAGTTATAT GCATTGGTAC
CAACAGAAAC CAGGACAGCC ACCCAAACTC CTCATCTATC GTGCATCCAA CCTAGAATCT
GGGGTCCCTG CCAGGTTCAG TGGCAGTGGG TCTGGGACAG ACTTCACCCT CAACATCCAT
CCTGTGGAGG AGGAGGATGC TGCAACCTAT TACTGTCAGC ACAGTAGGGA GCTTCCGCTC
ACGTTCGGTG CTGGGACCAA GCTGGAGCTG AAACGG
```
(SEQ ID NO:24)

D.

```
GACATTGTGC TGACACAGTC TCCTGCTTCC TTAGCTGTAT CTCTGGGGCA GAGGGCCACC
ATCTCATGCA GGGCCAGCAA GAGTGTCAGT ACATCTGGCT ATAGTTATAT GCATTGGTAC
CAACAGAAAC CAGGACAGCC ACCCAAACTC CTCATCTATC GTGCATCCAA CCTAGAATCT
GGGGTCCCTG CCAGGTTCAG TGGCAGTGGG TCTGGGACAG ACTTCACCCT CAACATCCAT
CCTGTGGAGG AGGAGGATGC TGCAACCTAT TACTGTCAGC ACAGTAGGGA GCTTCCGCTC
ACGTTCGGTG CTGGGACCAA GCTGGAGCTG AAACGG
```
(SEQ ID NO:25)

*FIG_6*

E.

*MAWVWTLLFLMAAAQSIQA***QIQLVQSGPELKKPGETVKISCKASGYTFTDYSVHWVKQAPGKGLKW
MGWINTETGEPTYADDFKGRFAFSLETSASTAYLQINNLKNEDTATYFCARAGGNAFAYWGQGTLV
TVSA**AKTTPPSVYPLAPGSAAQTNSMVT
(SEQ ID NO:26)

F.

```
                                          CDR H1                    CDR H2
QIQLVQSGPELKKPGETVKISCKASGYTFTDYSVHWVKQAPGKGLKWMGWINTETGEPTYAD
                           CDR H3
DFKGRFAFSLETSASTAYLQINNLKNEDTATYFCARAGGNAFAYWGQGTLVTVSA
```
(SEQ ID NO:27)

G.

ATGGCTTGGG TGTGGACCTT GCTATTCCTG ATGGCAGCTG CCCAAAGTAT CCAAGCACAG
ATCCAGTTGG TGCAGTCTGG ACCTGAGCTG AAGAAGCCTG GAGAGACAGT CAAGATCTCC
TGCAAGGCTT CTGGTTATAC CTTCACAGAC TATTCAGTGC ACTGGGTGAA GCAGGCTCCA
GGAAAGGGTT TAAAGTGGAT GGGCTGGATA AACACTGAGA CTGGTGAGCC AACATATGCA
GATGACTTCA AGGGACGGTT TGCCTTCTCT TTGGAAACCT CTGCCAGCAC TGCCTATTTG
CAGATCAACA ACCTCAAAAA TGAGGACACG GCTACATATT TCTGTGCTAG AGCGGGAGGT
AACGCCTTTG CTTACTGGGG CCAAGGGACT CTGGTCACTG TCTCTGCA
(SEQ ID NO:28)

H.

CAGATCCAGT TGGTGCAGTC TGGACCTGAG CTGAAGAAGC TGGAGAGAC AGTCAAGATC
TCCTGCAAGG CTTCTGGTTA TACCTTCACA GACTATTCAG TGCACTGGGT GAAGCAGGCT
CCAGGAAAGG GTTTAAAGTG GATGGGCTGG ATAAACACTG AGACTGGTGA GCCAACATAT
GCAGATGACT TCAAGGGACG GTTTGCCTTC TCTTTGGAAA CCTCTGCCAG CACTGCCTAT
TTGCAGATCA ACAACCTCAA AAATGAGGAC ACGGCTACAT ATTTCTGTGC TAGAGCGGGA
GGTAACGCCT TTGCTTACTG GGGCCAAGGG ACTCTGGTCA CTGTCTCTGC A
(SEQ ID NO:29)

*FIG_6 (cont'd)*

A.

*MRCLAEFLGLLVLWIPGAIG*<u>DIVMTQAAPSVPVTPGESVSISCRSSKSLLQSNGNTFLYWFMQRPG
QSPQLLIYRMSNLASGVPDRFSGSGSGTAFTLRISRVEAEDVGVYYCMQHLEYPFTFGGGTKLEIK
R</u>ADAAPTVSIFPPSSEQLT
(SEQ ID NO:30)

B.

```
                              CDR L1                           CDR L2
DIVMTQAAPSVPVTPGESVSISCRSSKSLLQSNGNTFLYWFMQRPGQSPQLLIYRMSNLASG
                      CDR L3
VPDRFSGSGSGTAFTLRISRVEAEDVGVYYCMQHLEYPFTFGGGTKLEIKR
```
(SEQ ID NO:31)

C.

<u>ATGAGGTGCC</u> TAGCTGAGTT CCTGGGGCTG CTTGTGCTCT GGATCCCTGG AGCCATTGGG
GATATTGTGA TGACTCAGGC TGCACCCTCT GTACCTGTCA CTCCTGGAGA GTCAGTATCC
ATCTCCTGCA GGTCTAGTAA GAGTCTCCTG CAAAGTAATG GCAACACTTT CTTGTATTGG
TTCATGCAGA GGCCAGGCCA GTCTCCTCAG CTCCTGATAT ATCGGATGTC CAACCTTGCC
TCAGGAGTCC CAGACAGGTT CAGTGGCAGT GGGTCAGGAA CTGCTTTCAC ACTGAGAATC
AGTAGAGTGG AGGCTGAGGA TGTGGGTGTT TATTACTGTA TGCAACATCT AGAATATCCT
TTCACGTTCG GAGGGGGGAC CAAGCTGGAA ATAAAACGG
(SEQ ID NO:32)

D.

GATATTGTGA TGACTCAGGC TGCACCCTCT GTACCTGTCA CTCCTGGAGA GTCAGTATCC
ATCTCCTGCA GGTCTAGTAA GAGTCTCCTG CAAAGTAATG GCAACACTTT CTTGTATTGG
TTCATGCAGA GGCCAGGCCA GTCTCCTCAG CTCCTGATAT ATCGGATGTC CAACCTTGCC
TCAGGAGTCC CAGACAGGTT CAGTGGCAGT GGGTCAGGAA CTGCTTTCAC ACTGAGAATC
AGTAGAGTGG AGGCTGAGGA TGTGGGTGTT TATTACTGTA TGCAACATCT AGAATATCCT
TTCACGTTCG GAGGGGGGAC CAAGCTGGAA ATAAAACGG
(SEQ ID NO:33)

*FIG_7*

E.

*MDWLWNLLFLMAAAQSIQA***QIQLVQSGPELKKPGETVKISCKASGYTFTNYGMNWVKQAPGKGLKW
MGWINTNTGEPTYAEEFKGRFAFSLETSASTAYLQINNLKNEDTATYFCARSGGSSPFAYWGQGTL
VTVSA**AKTTPPSVYPLAPGSAAQ
(SEQ ID NO:34)

F.

```
                                  CDR H1                    CDR H2
QIQLVQSGPELKKPGETVKISCKASGYTFTNYGMNWVKQAPGKGLKWMGWINTNTGEPTYAEEFKG
RF
                                  CDR H3
AFSLETSASTAYLQINNLKNEDTATYFCARSGGSSPFAYWGQGTLVTVSA
```
(SEQ ID NO:35)

G

ATGGATTGGC TGTGGAACTT GCTATTCCTG ATGGCAGCTG CCCAAAGTAT CCAAGCACAG
ATCCAGTTGG TGCAGTCTGG ACCTGAGCTG AAGAAGCCTG AGAGACAGT CAAGATCTCC
TGCAAGGCTT CTGGGTATAC CTTCACAAAC TATGGAATGA ACTGGGTGAA GCAGGCTCCA
GGAAAGGGTT TAAAGTGGAT GGGCTGGATA AACACCAACA CTGGAGAGCC AACATATGCT
GAAGAGTTCA AGGGACGGTT TGCCTTCTCT TTGGAAACCT CTGCCAGCAC TGCCTATTTG
CAGATCAACA ACCTCAAAAA TGAGGACACG GCTACATATT TCTGTGCAAG ATCGGGCGGT
AGTAGCCCTT TTGCTTACTG GGGCCAAGGG ACTCTGGTCA CTGTCTCTGC A
(SEQ ID NO:36)

H

CAGATCCAGT TGGTGCAGTC TGGACCTGAG CTGAAGAAGC TGGAGAGAC AGTCAAGATC
TCCTGCAAGG CTTCTGGGTA TACCTTCACA AACTATGGAA TGAACTGGGT GAAGCAGGCT
CCAGGAAAGG GTTTAAAGTG GATGGGCTGG ATAAACACCA ACACTGGAGA GCCAACATAT
GCTGAAGAGT TCAAGGGACG GTTTGCCTTC TCTTTGGAAA CCTCTGCCAG CACTGCCTAT
TTGCAGATCA ACAACCTCAA AAATGAGGAC ACGGCTACAT ATTTCTGTGC AAGATCGGGC
GGTAGTAGCC CTTTTGCTTA CTGGGGCCAA GGGACTCTGG TCACTGTCTC TGCA
(SEQ ID NO:37)

*FIG_7 (cont'd)*

QVQLVQSGAEVKKPGASVKVSCKASGYTFT CDR H1 WVRQAPGQGLEWMG CDR H2 RVTITADTSTSTAYMELSSLRSEDTAVYYCAR CDR H3
WGQGTLVTVSS (SEQ ID NO: 103)

QVQLQESGPGLVKPSQTLSLTCTVSGGSVS CDR H1 WIRQPPGKGLEWIG CDR H2 RVTISVDTSKNQFSLKLSSVTAADTAVYYCAR CDR H3
WGQGTLVTVSS (SEQ ID NO: 104)

EVQLVESGGGLVQPGGSLRLSCAASGFTFS CDR H1 WVRQAPGKGLEWVS CDR H2 RFTISRDNSKNTLYLQMNSLRAEDTAVYYCAR CDR H3
WGQGTLVTVSS (SEQ ID NO: 105)

QVQLVQSGSELKKPGASVKVSCKASGYTFT CDR H1 WVRQAPGQGLEWMG CDR H2 RFVFSLDTSVSTAYLQISSLKAEDTAVYYCAR CDR H3
WGQGTSLTVSS (SEQ ID NO: 106)

DIQMTQSPSSLSASVGDRVTITC CDR L1 WYQQKPGKAPKLLIY CDR L2 GVPSRFSGSGSGTDFTLTISSLQPEDFATYYC CDR L3 FGQGTKVEIK
(SEQ ID NO: 107)

DIVMTQSPLSLPVTPGEPASISC CDR L1 WYLQKPGQSPQLLIY CDR L2 GVPDRFSGSGSGTDFTLKISRVEAEDVGVYYC CDR L3 FGQGTKVEIK
(SEQ ID NO: 108)

EIVLTQSPGTLSLSPGERATLSC CDR L1 WYQQKPGQAPRLLIY CDR L2 GIPDRFSGSGSGTDFTLTISRLEPEDFAVYYC CDR L3 FGQGTKVEIK
(SEQ ID NO: 109)

DIVMTQSPDSLAVSLGERATINC CDR L1 WYQQKPGQPPKLLIY CDR L2 GVPDRFSGSGSGTDFTLTISSLQAEDVAVYYC CDR L3 FGQGTKVEI
(SEQ ID NO: 110)

FIG_8

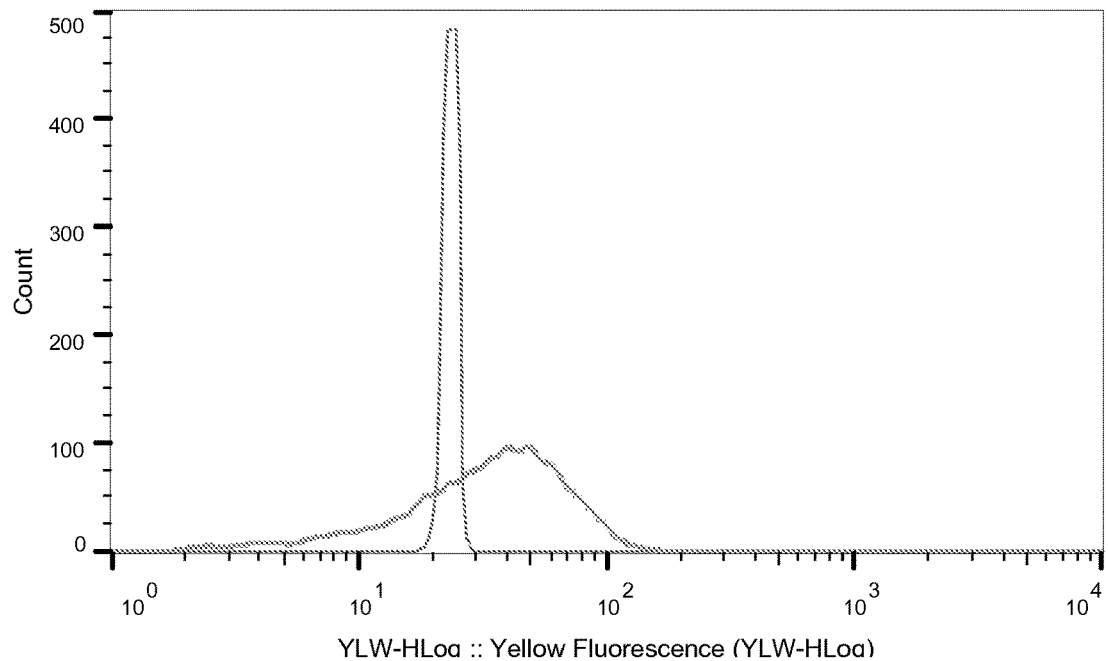
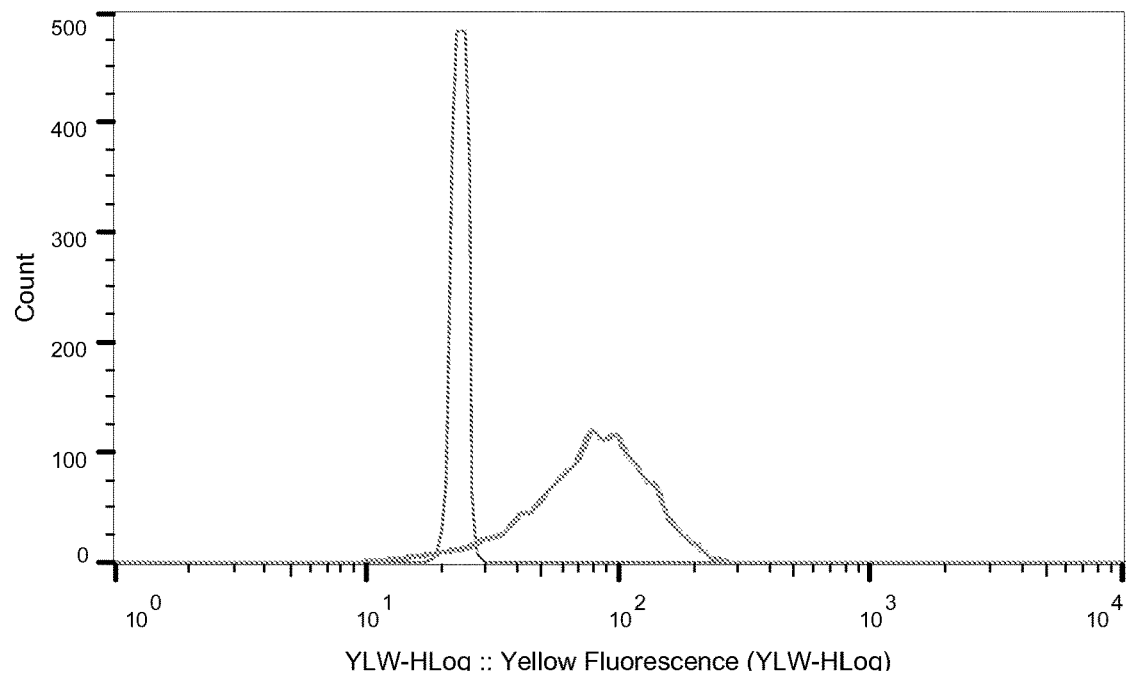
FIG_9

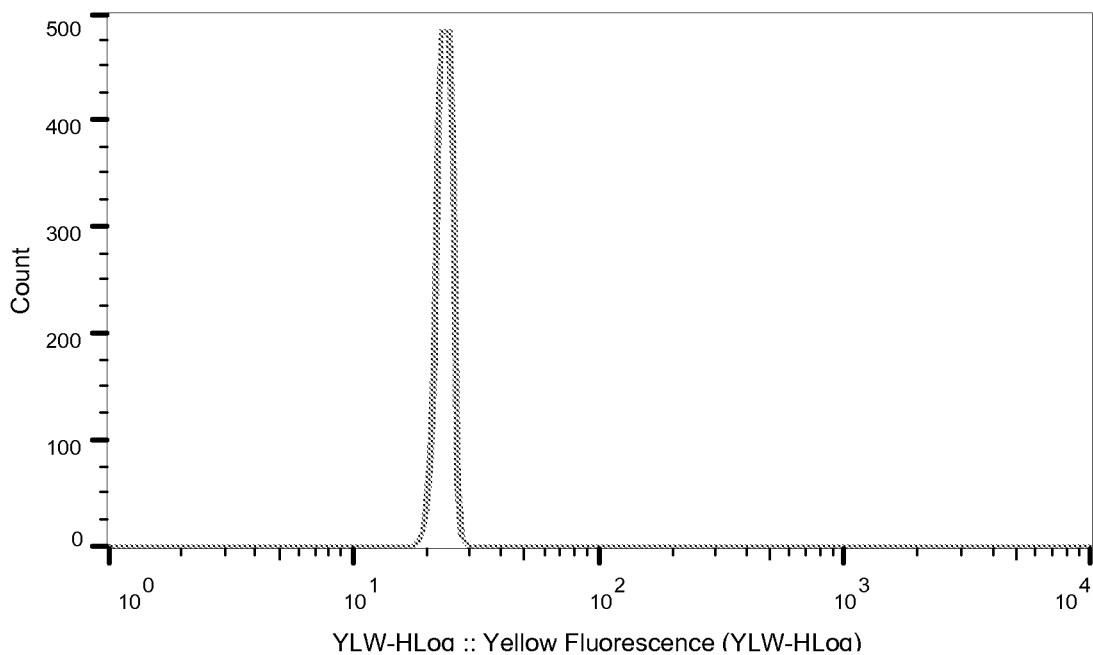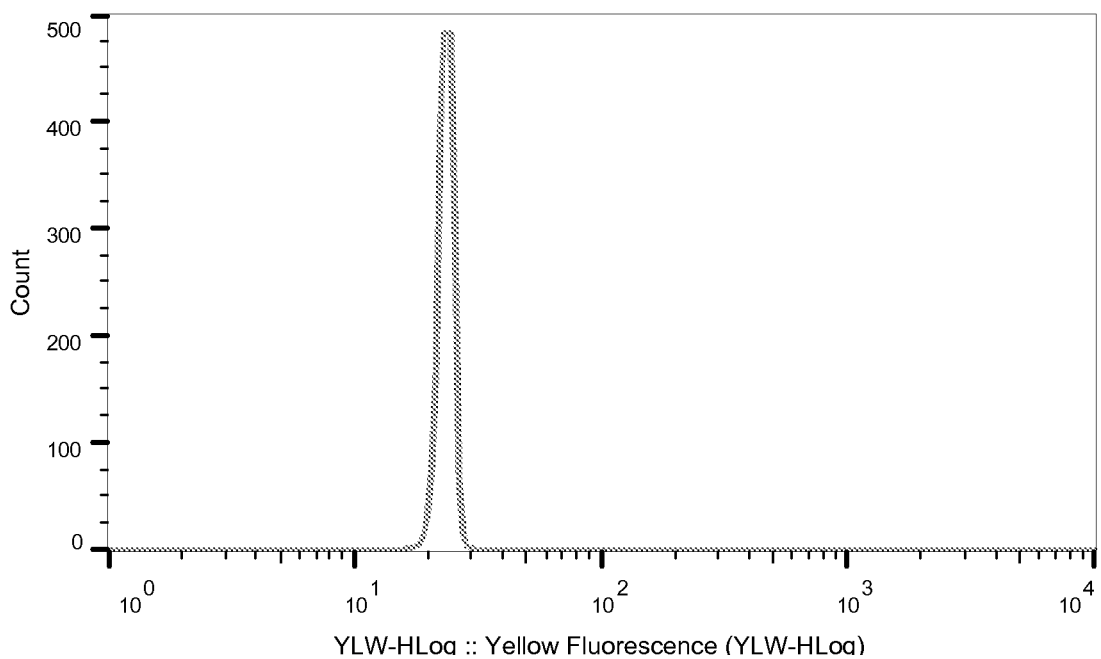
FIG_9 (cont'd)

ured MICA protein of the

SEQUENCE LISTING

```
<160> NUMBER OF SEQ ID NOS: 110

<210> SEQ ID NO 1
<211> LENGTH: 383
<212> TYPE: PRT
<213> ORGANISM: Homo sapiens

<400> SEQUENCE: 1

Met Gly Leu Gly Pro Val Phe Leu Leu Ala Gly Ile Phe Pro Phe
1               5                   10                  15

Ala Pro Pro Gly Ala Ala Ala Glu Pro His Ser Leu Arg Tyr Asn Leu
                20                  25                  30

Thr Val Leu Ser Trp Asp Gly Ser Val Gln Ser Gly Phe Leu Thr Glu
            35                  40                  45

Val His Leu Asp Gly Gln Pro Phe Leu Arg Cys Asp Arg Gln Lys Cys
        50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
                100                 105                 110

Leu Gln Glu Ile Arg Val Cys Glu Ile His Glu Asp Asn Ser Thr Arg
            115                 120                 125

Ser Ser Gln His Phe Tyr Tyr Asp Gly Glu Leu Phe Leu Ser Gln Asn
        130                 135                 140

Leu Glu Thr Lys Glu Trp Thr Met Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
                180                 185                 190
```

Arg Tyr Leu Lys Ser Gly Val Val Leu Arg Thr Val Pro Pro Met
        195                 200                 205

Val Asn Val Thr Arg Ser Glu Ala Ser Glu Gly Asn Ile Thr Val Thr
210                 215                 220

Cys Arg Ala Ser Gly Phe Tyr Pro Trp Asn Ile Thr Leu Ser Trp Arg
225                 230                 235                 240

Gln Asp Gly Val Ser Leu Ser His Asp Thr Gln Gln Trp Gly Asp Val
                245                 250                 255

Leu Pro Asp Gly Asn Gly Thr Tyr Gln Thr Trp Val Ala Thr Arg Ile
            260                 265                 270

Cys Gln Gly Glu Glu Gln Arg Phe Thr Cys Tyr Met Glu His Ser Gly
        275                 280                 285

Asn His Ser Thr His Pro Val Pro Ser Gly Lys Val Leu Val Leu Gln
290                 295                 300

Ser His Trp Gln Thr Phe His Val Ser Ala Val Ala Ala Ala Ala Ile
305                 310                 315                 320

Phe Val Ile Ile Ile Phe Tyr Val Arg Cys Cys Lys Lys Lys Thr Ser
                325                 330                 335

Ala Ala Glu Gly Pro Glu Leu Val Ser Leu Gln Val Leu Asp Gln His
            340                 345                 350

Pro Val Gly Thr Ser Asp His Arg Asp Ala Thr Gln Leu Gly Phe Gln
        355                 360                 365

Pro Leu Met Ser Asp Leu Gly Ser Thr Gly Ser Thr Glu Gly Ala
    370                 375                 380

<210> SEQ ID NO 2
<211> LENGTH: 383
<212> TYPE: PRT
<213> ORGANISM: Homo sapiens

<400> SEQUENCE: 2

Met Gly Leu Gly Arg Val Leu Leu Phe Leu Ala Val Ala Phe Pro Phe
1               5                   10                  15

Ala Pro Pro Ala Ala Ala Ala Glu Pro His Ser Leu Arg Tyr Asn Leu
            20                  25                  30

Met Val Leu Ser Gln Asp Glu Ser Val Gln Ser Gly Phe Leu Ala Glu
        35                  40                  45

Gly His Leu Asp Gly Gln Pro Phe Leu Arg Tyr Asp Arg Gln Lys Arg
    50                  55                  60

Arg Ala Lys Pro Gln Gly Gln Trp Ala Glu Asp Val Leu Gly Ala Lys
65                  70                  75                  80

Thr Trp Asp Thr Glu Thr Glu Asp Leu Thr Glu Asn Gly Gln Asp Leu
                85                  90                  95

Arg Arg Thr Leu Thr His Ile Lys Asp Gln Lys Gly Gly Leu His Ser
            100                 105                 110

Leu Gln Glu Ile Arg Val Cys Glu Ile His Glu Asp Ser Ser Thr Arg
        115                 120                 125

Gly Ser Arg His Phe Tyr Tyr Asp Gly Glu Leu Phe Leu Ser Gln Asn
    130                 135                 140

Leu Glu Thr Gln Glu Ser Thr Val Pro Gln Ser Ser Arg Ala Gln Thr
145                 150                 155                 160

Leu Ala Met Asn Val Thr Asn Phe Trp Lys Glu Asp Ala Met Lys Thr
                165                 170                 175

Lys Thr His Tyr Arg Ala Met Gln Ala Asp Cys Leu Gln Lys Leu Gln

```
                    180               185               190
Arg Tyr Leu Lys Ser Gly Val Ala Ile Arg Arg Thr Val Pro Pro Met
            195                 200                 205

Val Asn Val Thr Cys Ser Glu Val Ser Glu Gly Asn Ile Thr Val Thr
        210                 215                 220

Cys Arg Ala Ser Ser Phe Tyr Pro Arg Asn Ile Thr Leu Thr Trp Arg
225                 230                 235                 240

Gln Asp Gly Val Ser Leu Ser His Asn Thr Gln Gln Trp Gly Asp Val
                245                 250                 255

Leu Pro Asp Gly Asn Gly Thr Tyr Gln Thr Trp Val Ala Thr Arg Ile
            260                 265                 270

Arg Gln Gly Glu Glu Gln Arg Phe Thr Cys Tyr Met Glu His Ser Gly
        275                 280                 285

Asn His Gly Thr His Pro Val Pro Ser Gly Lys Val Leu Val Leu Gln
        290                 295                 300

Ser Gln Arg Thr Asp Phe Pro Tyr Val Ser Ala Ala Met Pro Cys Phe
305                 310                 315                 320

Val Ile Ile Ile Ile Leu Cys Val Pro Cys Cys Lys Lys Lys Thr Ser
                325                 330                 335

Ala Ala Glu Gly Pro Glu Leu Val Ser Leu Gln Val Leu Asp Gln His
                340                 345                 350

Pro Val Gly Thr Gly Asp His Arg Asp Ala Ala Gln Leu Gly Phe Gln
            355                 360                 365

Pro Leu Met Ser Ala Thr Gly Ser Thr Gly Ser Thr Glu Gly Ala
370                 375                 380

<210> SEQ ID NO 3
<211> LENGTH: 93
<212> TYPE: PRT
<213> ORGANISM: Homo sapiens

<400> SEQUENCE: 3

Val Pro Pro Met Val Asn Val Thr Arg Ser Glu Ala Ser Glu Gly Asn
1               5                   10                  15

Ile Thr Val Thr Cys Arg Ala Ser Gly Phe Tyr Pro Trp Asn Ile Thr
            20                  25                  30

Leu Ser Trp Arg Gln Asp Gly Val Ser Leu Ser His Asp Thr Gln Gln
        35                  40                  45

Trp Gly Asp Val Leu Pro Asp Gly Asn Gly Thr Tyr Gln Thr Trp Val
    50                  55                  60

Ala Thr Arg Ile Cys Gln Gly Glu Glu Gln Arg Phe Thr Cys Tyr Met
65                  70                  75                  80

Glu His Ser Gly Asn His Ser Thr His Pro Val Pro Ser
                85                  90

<210> SEQ ID NO 4
<211> LENGTH: 93
<212> TYPE: PRT
<213> ORGANISM: Homo sapiens

<400> SEQUENCE: 4

Val Pro Pro Met Val Asn Val Thr Cys Ser Glu Val Ser Glu Gly Asn
1               5                   10                  15

Ile Thr Val Thr Cys Arg Ala Ser Ser Phe Tyr Pro Arg Asn Ile Thr
            20                  25                  30

Leu Thr Trp Arg Gln Asp Gly Val Ser Leu Ser His Asn Thr Gln Gln
```

| | 35 | | | 40 | | | | 45 | | | |
|---|---|---|---|---|---|---|---|---|---|---|---|
Trp Gly Asp Val Leu Pro Asp Gly Asn Gly Thr Tyr Gln Thr Trp Val
        50                          55                      60

Ala Thr Arg Ile Arg Gln Gly Glu Glu Gln Arg Phe Thr Cys Tyr Met
65                      70                      75                      80

Glu His Ser Gly Asn His Gly Thr His Pro Val Pro Ser
                    85                      90

<210> SEQ ID NO 5
<211> LENGTH: 1365
<212> TYPE: DNA
<213> ORGANISM: Homo sapiens

<400> SEQUENCE: 5

```
cactgcttga gccgctgaga gggtggcgac gtcggggcca tggggctggg cccggtcttc      60
ctgcttctgg ctggcatctt ccctttttgca cctccgggag ctgctgctga gccccacagt    120
cttcgtttata acctcacggt gctgtcctgg gatggatctg tgcagtcagg gtttctcact    180
gaggtacatc tggatggtca gcccttcctg cgctgtgaca ggcagaaatg cagggcaaag    240
ccccagggac agtgggcaga agatgtcctg ggaaataaga catgggacag agagaccaga    300
gacttgacag ggaacggaaa ggacctcagg atgaccctgg ctcatatcaa ggaccagaaa    360
gaaggcttgc attccctcca ggagattagg gtctgtgaga tccatgaaga caacagcacc    420
aggagctccc agcatttcta ctacgatggg gagctcttcc tctcccaaaa cctggagact    480
aaggaatgga caatgcccca gtcctccaga gctcagacct ggccatgaa cgtcaggaat    540
ttcttgaagg aagatgccat gaagaccaag acacactatc acgctatgca tgcagactgc    600
ctgcaggaac tacggcgata tctaaaatcc ggcgtagtcc tgaggagaac agtgcccccc    660
atggtgaatg tcacccgcag cgaggcctca gagggcaaca ttaccgtgac atgcagggct    720
tctggcttct atccctggaa tatcacactg agctggcgtc aggatggggt atctttgagc    780
cacgacaccc agcagtgggg ggatgtcctg cctgatggga atgaaccta ccagacctgg    840
gtggccacca ggatttgcca aggagaggag cagaggttca cctgctacat ggaacacagc    900
gggaatcaca gcactcaccc tgtgccctct gggaaagtgc tggtgcttca gagtcattgg    960
cagacattcc atgtttctgc tgttgctgct gctgctattt ttgttattat tattttctat   1020
gtccgttgtt gtaagaagaa acatcagct gcagagggtc cagagctcgt gagcctgcag   1080
gtcctggatc aacacccagt tgggacgagt gaccacaggg atgccacaca gctcggattt   1140
cagcctctga tgtcagatct tgggtccact ggctccactg agggcgccta gactctacag   1200
ccaggcagct gggattcaat tccctgcctg gatctcacga gcactttccc tcttggtgcc   1260
tcagtttcct gacctatgaa acagagaaaa taaaagcact tatttattgt tgttggaggc   1320
tgcaaaatgt tagtagatat gaggcgtttg cagctgtacc atatt                   1365
```

<210> SEQ ID NO 6
<211> LENGTH: 2380
<212> TYPE: DNA
<213> ORGANISM: Homo sapiens

<400> SEQUENCE: 6

```
gggccatggg gctgggccgg tcctgctgt ttctggccgt cgccttccct tttgcacccc       60
cggcagccgc cgctgagccc cacagtcttc gttacaacct catggtgctg tcccaggatg     120
aatctgtgca gtcagggttt ctcgctgagg gacatctgga tggtcagccc ttcctgcgct    180
```

| | |
|---|---|
| atgacaggca gaaacgcagg gcaaagcccc agggacagtg ggcagaagat gtcctgggag | 240 |
| ctaagacctg ggacacagag accgaggact tgacagagaa tgggcaagac ctcaggagga | 300 |
| ccctgactca tatcaaggac cagaaaggag gcttgcattc cctccaggag attagggtct | 360 |
| gtgagatcca tgaagacagc agcaccaggg gctcccggca tttctactac gatggggagc | 420 |
| tcttcctctc ccaaaacctg gagactcaag aatcgacagt gccccagtcc tccagagctc | 480 |
| agaccttggc tatgaacgtc acaaatttct ggaaggaaga tgccatgaag accaagacac | 540 |
| actatcgcgc tatgcaggca gactgcctgc agaaactaca gcgatatctg aaatccgggg | 600 |
| tggccatcag gagaacagtg cccccatgg tgaatgtcac ctgcagcgag gtctcagagg | 660 |
| gcaacatcac cgtgacatgc agggcttcca gcttctatcc ccggaatatc acactgacct | 720 |
| ggcgtcagga tggggtatct ttgagccaca cacccagca gtgggggat gtcctgcctg | 780 |
| atgggaatgg aacctaccag acctgggtgg ccaccaggat tcgccaagga gaggagcaga | 840 |
| ggttcacctg ctacatggaa cacagcggga atcacggcac tcaccctgtg ccctctggga | 900 |
| aggtgctggt gcttcagagt caacggacag actttccata tgtttctgct gctatgccat | 960 |
| gttttgttat tattattatt ctctgtgtcc cttgttgcaa gaagaaaaca tcagcggcag | 1020 |
| agggtccaga gcttgtgagc ctgcaggtcc tggatcaaca cccagttggg acaggagacc | 1080 |
| acagggatgc agcacagctg ggatttcagc ctctgatgtc agctactggg tccactggtt | 1140 |
| ccactgaggg cgcctagact ctacagccag gcggccagga ttcaactccc tgcctggatc | 1200 |
| tcaccagcac tttccctctg tttcctgacc tatgaaacag aaaataacat cacttattta | 1260 |
| ttgttgttgg atgctgcaaa gtgttagtag gtatgaggtg tttgctgctc tgccacgtag | 1320 |
| agagccagca aagggatcat gaccaactca acattccatt ggaggctata tgatcaaaca | 1380 |
| gcaaattgtt tatcatgaat gcaggatgtg ggcaaactca cgactgctcc tgccaacaga | 1440 |
| aggtttgctg agggcattca ctccatggtg ctcattggag ttatctactg ggtcatctag | 1500 |
| agcctattgt ttgaggaatg cagtcttaca agcctactct ggacccagca gctgactcct | 1560 |
| tcttccaccc ctcttcttgc tatctcctat accaataaat acgaagggct gtggaagatc | 1620 |
| agagcccttg ttcacgagaa gcaagaagcc ccctgacccc ttgttccaaa tatactcttt | 1680 |
| tgtctttctc tttattccca cgttcgccct tgttcagtc caatacaggg ttgtggggcc | 1740 |
| cttaacagtg ccatattaat tggtatcatt atttctgttg ttttttgtttt tgttttttgtt | 1800 |
| tttgttttg agacagagtc tcactcgtca cccaggctgc agttcactgg tgtgatctca | 1860 |
| gctcactgca acctctgcct cccaggttca agcacttctc gtacctcaga ctcccgatag | 1920 |
| ctgggattac agacaggcac caccacaccc agctaatttt tgtatttttt gtagagacgg | 1980 |
| ggtttcgcca agttgaccag cccagtttca aactcctgac ctcaggtgat ctgcctgcct | 2040 |
| tggcatccca aagtgctggg attacaagaa tgagccaccg tgcctggcct atttttattat | 2100 |
| attgtaatat atttttattat attagccacc atgcctgtcc tatttttctta tgttttaata | 2160 |
| tattttaata tattacatgt gcagtaatta gattatcatg ggtgaacttt atgagtgagt | 2220 |
| atcttggtga tgactcctcc tgaccagccc aggaccagct tcttgtcac cttgaggtcc | 2280 |
| cctcgccccg tcacaccgtt atcgattact ctgtgtctac tattatgtgt gcataattta | 2340 |
| taccgtaaat gtttactctt taaataaaaa aaaaaaaaa | 2380 |

<210> SEQ ID NO 7
<211> LENGTH: 274
<212> TYPE: PRT
<213> ORGANISM: Homo sapiens

<400> SEQUENCE: 7

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser
```

<210> SEQ ID NO 8
<211> LENGTH: 274
<212> TYPE: PRT
<213> ORGANISM: Homo sapiens

<400> SEQUENCE: 8

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80
```

```
Lys Asp Gln Lys Glu Gly Leu His Ser Leu Gln Glu Ile Arg Val Cys
                85                  90                  95
Glu Ile His Glu Asp Asn Ser Thr Arg Ser Ser Gln His Phe Tyr Tyr
            100                 105                 110
Asp Gly Glu Leu Phe Leu Ser Gln Asn Leu Glu Thr Glu Trp Thr
            115                 120                 125
Met Pro Gln Ser Ser Arg Ala Gln Thr Leu Ala Met Asn Val Arg Asn
            130                 135                 140
Phe Leu Lys Glu Asp Ala Met Lys Thr Lys Thr Leu Tyr His Ala Met
145                 150                 155                 160
His Ala Asp Cys Leu Gln Glu Leu Arg Arg Tyr Leu Lys Ser Gly Val
                165                 170                 175
Val Leu Arg Arg Thr Val Pro Pro Met Val Asn Val Thr Arg Ser Glu
            180                 185                 190
Ala Ser Glu Gly Asn Ile Thr Val Thr Cys Arg Ala Ser Gly Phe Tyr
            195                 200                 205
Pro Trp Asn Ile Thr Leu Ser Trp Arg Gln Asp Gly Val Ser Leu Ser
            210                 215                 220
His Asp Thr Gln Gln Trp Gly Asp Val Leu Pro Asp Gly Asn Gly Thr
225                 230                 235                 240
Tyr Gln Thr Trp Val Ala Thr Arg Ile Cys Gln Gly Glu Glu Gln Arg
                245                 250                 255
Phe Thr Cys Tyr Met Glu His Ser Gly Asn His Ser Thr His Pro Val
                260                 265                 270
Pro Ser

<210> SEQ ID NO 9
<211> LENGTH: 274
<212> TYPE: PRT
<213> ORGANISM: Homo sapiens

<400> SEQUENCE: 9

Glu Pro His Ser Leu Arg Tyr Asn Leu Thr Val Leu Ser Trp Asp Gly
1               5                   10                  15
Ser Val Gln Ser Gly Phe Leu Ala Glu Val His Leu Asp Gly Gln Pro
            20                  25                  30
Phe Leu Arg Cys Asp Arg Gln Lys Cys Arg Ala Lys Pro Gln Gly Gln
            35                  40                  45
Trp Ala Glu Asp Val Leu Gly Asn Lys Thr Trp Asp Arg Glu Thr Arg
50                  55                  60
Asp Leu Thr Gly Asn Gly Lys Asp Leu Arg Met Thr Leu Ala His Ile
65                  70                  75                  80
Lys Asp Gln Lys Glu Gly Leu His Ser Leu Gln Glu Ile Arg Val Cys
                85                  90                  95
Glu Ile His Glu Asp Asn Ser Thr Arg Ser Ser Gln His Phe Tyr Tyr
            100                 105                 110
Asp Gly Glu Leu Phe Leu Ser Gln Asn Leu Glu Thr Glu Trp Thr
            115                 120                 125
Met Pro Gln Ser Ser Arg Ala Gln Thr Leu Ala Met Asn Ile Arg Asn
            130                 135                 140
Phe Leu Lys Glu Asp Ala Met Lys Thr Lys Thr His Tyr His Ala Met
145                 150                 155                 160
His Ala Asp Cys Leu Gln Glu Leu Arg Arg Tyr Leu Lys Ser Gly Val
                165                 170                 175
```

Val Leu Arg Arg Thr Val Pro Pro Met Val Asn Val Thr Arg Ser Glu
          180                 185                 190

Ala Ser Glu Gly Asn Ile Thr Val Thr Cys Arg Ala Ser Gly Phe Tyr
      195                 200                 205

Pro Trp Asn Ile Thr Leu Ser Trp Arg Gln Asp Gly Val Ser Leu Ser
      210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
              245                 250                 255

Phe Thr Cys Tyr Met Glu His Ser Gly Asn His Ser Thr His Pro Val
          260                 265                 270

Pro Ser

<210> SEQ ID NO 10
<211> LENGTH: 274
<212> TYPE: PRT
<213> ORGANISM: Homo sapiens

<400> SEQUENCE: 10

Glu Pro His Ser Leu Pro Tyr Asn Leu Thr Val Leu Ser Trp Asp Gly
1               5                   10                  15

Ser Val Gln Ser Gly Phe Leu Ala Glu Val His Leu Asp Gly Gln Pro
              20                  25                  30

Phe Leu Arg Tyr Asp Arg Gln Lys Cys Arg Ala Lys Pro Gln Gly Gln
          35                  40                  45

Trp Ala Glu Asp Val Leu Gly Asn Lys Thr Trp Asp Arg Glu Thr Arg
 50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
              85                  90                  95

Glu Ile His Glu Asp Asn Ser Thr Arg Ser Ser Gln His Phe Tyr Tyr
          100                 105                 110

Asp Gly Glu Leu Phe Leu Ser Gln Asn Leu Glu Thr Glu Glu Trp Thr
      115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
              165                 170                 175

Val Leu Arg Arg Thr Val Pro Pro Met Val Asn Val Thr Arg Ser Glu
          180                 185                 190

Ala Ser Glu Gly Asn Ile Thr Val Thr Cys Arg Ala Ser Gly Phe Tyr
      195                 200                 205

Pro Trp Asn Ile Thr Leu Ser Trp Arg Gln Asp Gly Val Ser Leu Ser
      210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
              245                 250                 255

Phe Thr Cys Tyr Met Glu His Ser Gly Asn His Ser Thr His Pro Val
          260                 265                 270

Pro Ser

<210> SEQ ID NO 11
<211> LENGTH: 274
<212> TYPE: PRT
<213> ORGANISM: Homo sapiens

<400> SEQUENCE: 11

Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Tyr Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Trp Thr
        115                 120                 125

Val Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Glu Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 12
<211> LENGTH: 274
<212> TYPE: PRT
<213> ORGANISM: Homo sapiens

<400> SEQUENCE: 12

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

```
Trp Ala Glu Asp Val Leu Gly Asn Lys Thr Trp Asp Arg Glu Thr Arg
         50                  55                  60

Asp Leu Thr Gly Asn Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
            115                 120                 125

Met Pro Gln Ser Ser Arg Ala Gln Thr Leu Ala Met Asn Val Arg Asn
        130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
            195                 200                 205

Pro Trp Asn Ile Thr Leu Ser Trp Arg Gln Asp Gly Val Ser Leu Ser
        210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 13
<211> LENGTH: 274
<212> TYPE: PRT
<213> ORGANISM: Homo sapiens

<400> SEQUENCE: 13

Glu Pro His Ser Leu Arg Tyr Asn Leu Thr Val Leu Ser Trp Asp Gly
  1               5                  10                  15

Ser Val Gln Ser Gly Phe Leu Ala Glu Val His Leu Asp Gly Gln Pro
             20                  25                  30

Phe Leu Arg Cys Asp Arg Gln Lys Cys Arg Ala Lys Pro Gln Gly Gln
         35                  40                  45

Trp Ala Glu Asp Val Leu Gly Asn Lys Thr Trp Asp Arg Glu Thr Arg
     50                  55                  60

Asp Leu Thr Gly Asn Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
            115                 120                 125

Met Pro Gln Ser Ser Arg Ala Gln Thr Leu Ala Met Asn Val Arg Asn
        130                 135                 140
```

```
Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
                260                 265                 270

Pro Ser

<210> SEQ ID NO 14
<211> LENGTH: 276
<212> TYPE: PRT
<213> ORGANISM: Homo sapiens

<400> SEQUENCE: 14

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240
```

```
Tyr Gln Thr Trp Val Ala Thr Arg Ile Cys Gln Gly Glu Glu Gln Arg
                    245                 250                 255

Phe Thr Cys Tyr Met Glu His Ser Gly Asn His Ser Thr His Pro Val
            260                 265                 270

Pro Ser Gly Lys
        275

<210> SEQ ID NO 15
<211> LENGTH: 274
<212> TYPE: PRT
<213> ORGANISM: Homo sapiens

<400> SEQUENCE: 15

Glu Pro His Ser Leu Arg Tyr Asn Leu Met Val Leu Ser Gln Asp Glu
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Ala Lys Pro Gln Gly Gln
        35                  40                  45

Trp Ala Glu Asp Val Leu Gly Ala Lys Thr Trp Asp Thr Glu Thr Glu
50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
            100                 105                 110

Asp Gly Glu Leu Phe Leu Ser Gln Asn Leu Glu Thr Gln Glu Ser Thr
        115                 120                 125

Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Thr Cys Ser Glu
            180                 185                 190

Val Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Arg
                245                 250                 255

Phe Thr Cys Tyr Met Glu His Ser Gly Asn His Gly Thr His Pro Val
            260                 265                 270

Pro Ser

<210> SEQ ID NO 16
<211> LENGTH: 275
<212> TYPE: PRT
<213> ORGANISM: Homo sapiens

<400> SEQUENCE: 16
```

```
Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Lys Thr Trp Asp Thr Glu Thr Glu Asp
    50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asp
            100                 105                 110

Gly Glu Leu Phe Leu Ser Gln Asn Leu Glu Thr Gln Glu Ser Thr Val
            115                 120                 125

Pro Gln Ser Ser Arg Ala Gln Thr Leu Ala Met Asn Val Thr Asn Phe
        130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Leu Pro Pro Met Val Asn Val Ile
                165                 170                 175

Cys Ser Glu Val Ser Glu Gly Asn Ile Thr Val Thr Cys Arg Ala Ser
            180                 185                 190

Ser Phe Tyr Pro Arg Asn Ile Thr Leu Thr Trp Arg Gln Asp Gly Val
        195                 200                 205

Ser Leu Ser His Asn Thr Gln Gln Trp Gly Asp Val Leu Pro Asp Gly
        210                 215                 220

Asn Gly Thr Tyr Gln Thr Trp Val Ala Thr Arg Ile Arg Gln Gly Glu
225                 230                 235                 240

Glu Gln Arg Phe Thr Cys Tyr Met Glu His Ser Gly Asn His Gly Thr
                245                 250                 255

His Pro Val Pro Ser Gly Lys Ala Leu Val Leu Gln Ser Gln Arg Thr
            260                 265                 270

Asp Phe Pro
        275

<210> SEQ ID NO 17
<211> LENGTH: 273
<212> TYPE: PRT
<213> ORGANISM: Homo sapiens

<400> SEQUENCE: 17

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Glu Thr Trp Asp Thr Glu Thr Glu Asp
    50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95
```

Met His Glu Asp Ser Ser Thr Arg Gly Ser Arg His Phe Tyr Tyr Asn
                100                 105                 110

Gly Glu Leu Phe Leu Ser Gln Asn Leu Glu Thr Gln Glu Ser Thr Val
                115                 120                 125

Pro Gln Ser Ser Arg Ala Gln Thr Leu Ala Met Asn Val Thr Asn Phe
                130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Thr Cys Ser Glu Val
                180                 185                 190

Ser Glu Gly Asn Ile Thr Val Thr Cys Arg Ala Ser Ser Phe Tyr Pro
                195                 200                 205

Arg Asn Ile Thr Leu Thr Trp Arg Gln Asp Gly Val Ser Leu Ser His
                210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Arg Phe
                245                 250                 255

Thr Cys Tyr Met Glu His Ser Gly Asn His Gly Thr His Pro Val Pro
                260                 265                 270

Ser

<210> SEQ ID NO 18
<211> LENGTH: 273
<212> TYPE: PRT
<213> ORGANISM: Homo sapiens

<400> SEQUENCE: 18

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
                20                  25                  30

Leu Arg Tyr Asp Arg Gln Lys Arg Arg Ala Lys Pro Gln Gly Gln Trp
                35                  40                  45

Ala Glu Asp Val Leu Gly Ala Lys Thr Trp Asp Thr Glu Thr Glu Asp
                50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asp
                100                 105                 110

Gly Glu Leu Phe Leu Ser Gln Asn Leu Glu Thr Gln Glu Ser Thr Val
                115                 120                 125

Pro Gln Ser Ser Arg Ala Gln Thr Leu Ala Met Asn Val Thr Asn Phe
                130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Ile Cys Ser Glu Val
                180                 185                 190

```
Ser Glu Gly Asn Ile Thr Val Thr Cys Arg Ala Ser Ser Phe Tyr Pro
            195                 200                 205

Arg Asn Ile Thr Leu Thr Trp Arg Gln Asp Gly Val Ser Leu Ser His
210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Arg Phe
            245                 250                 255

Thr Cys Tyr Met Glu His Ser Gly Asn His Gly Thr His Pro Val Pro
            260                 265                 270

Ser
```

<210> SEQ ID NO 19
<211> LENGTH: 273
<212> TYPE: PRT
<213> ORGANISM: Homo sapiens

<400> SEQUENCE: 19

```
Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asn Val Leu Gly Ala Lys Thr Trp Asp Thr Glu Thr Glu Asp
50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asp
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
            195                 200                 205

Arg Asn Ile Thr Leu Thr Trp Arg Gln Asp Gly Val Ser Leu Ser His
210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Arg Phe
            245                 250                 255

Thr Cys Tyr Met Glu His Ser Gly Asn His Gly Thr His Pro Val Pro
            260                 265                 270

Ser
```

```
<210> SEQ ID NO 20
<211> LENGTH: 273
<212> TYPE: PRT
<213> ORGANISM: Homo sapiens

<400> SEQUENCE: 20

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Glu Thr Trp Asp Thr Glu Thr Glu Asp
    50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asn
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
    130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
        195                 200                 205

Arg Asn Ile Thr Leu Thr Trp Arg Gln Asp Gly Val Ser Leu Ser His
    210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Lys Phe
                245                 250                 255

Thr Cys Tyr Met Glu His Ser Gly Asn His Gly Thr His Pro Val Pro
                260                 265                 270

Ser

<210> SEQ ID NO 21
<211> LENGTH: 273
<212> TYPE: PRT
<213> ORGANISM: Homo sapiens

<400> SEQUENCE: 21

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Glu Thr Trp Asp Thr Glu Thr Glu Asp
```

```
            50                  55                  60
Leu Thr Glu Asn Gly Gln Asp Leu Arg Arg Thr Leu Thr His Ile Lys
 65                  70                  75                  80

Asp Gln Lys Gly Gly Leu His Ser Leu Gln Glu Ile Arg Val Cys Glu
                 85                  90                  95

Ile His Glu Asp Ser Ser Thr Arg Gly Ser Arg His Phe Tyr Tyr Asn
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
        195                 200                 205

Arg Asn Ile Thr Leu Thr Trp Arg Gln Asp Gly Val Ser Leu Ser His
210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Arg Phe
                245                 250                 255

Thr Cys Tyr Met Glu His Ser Gly Asn His Gly Thr His Pro Val Pro
            260                 265                 270

Ser

<210> SEQ ID NO 22
<211> LENGTH: 153
<212> TYPE: PRT
<213> ORGANISM: Artificial Sequence
<220> FEATURE:
<223> OTHER INFORMATION: light chain of antibody 1F5

<400> SEQUENCE: 22

Met Glu Thr Asp Thr Leu Leu Leu Trp Val Leu Leu Leu Trp Val Pro
  1               5                  10                  15

Gly Ser Ala Gly Asp Ile Val Leu Thr Gln Ser Pro Ala Ser Leu Ala
                 20                  25                  30

Val Ser Leu Gly Gln Arg Ala Thr Ile Ser Cys Arg Ala Ser Lys Ser
             35                  40                  45

Val Ser Thr Ser Gly Tyr Ser Tyr Met His Trp Tyr Gln Gln Lys Pro
 50                  55                  60

Gly Gln Pro Pro Lys Leu Leu Ile Tyr Arg Ala Ser Asn Leu Glu Ser
 65                  70                  75                  80

Gly Val Pro Ala Arg Phe Ser Gly Ser Gly Ser Gly Thr Asp Phe Thr
                 85                  90                  95

Leu Asn Ile His Pro Val Glu Glu Asp Ala Ala Thr Tyr Tyr Cys
            100                 105                 110

Gln His Ser Arg Glu Leu Pro Leu Thr Phe Gly Ala Gly Thr Lys Leu
        115                 120                 125

Glu Leu Lys Arg Ala Asp Ala Ala Pro Thr Val Ser Ile Phe Pro Pro
130                 135                 140
```

Ser Ser Glu Gln Leu Thr Ser Gly Gly
145                 150

<210> SEQ ID NO 23
<211> LENGTH: 112
<212> TYPE: PRT
<213> ORGANISM: Artificial Sequence
<220> FEATURE:
<223> OTHER INFORMATION: light chain variable region of antibody 1F5

<400> SEQUENCE: 23

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Lys Arg
            100                 105                 110

<210> SEQ ID NO 24
<211> LENGTH: 396
<212> TYPE: DNA
<213> ORGANISM: Artificial Sequence
<220> FEATURE:
<223> OTHER INFORMATION: light chain of antibody 1F5

<400> SEQUENCE: 24
atggagacag acacactcct gttatgggta ctgctgctct gggttccagg ttccgctggt    60
gacattgtgc tgacacagtc tcctgcttcc ttagctgtat ctctggggca gagggccacc    120
atctcatgca gggccagcaa gagtgtcagt acatctggct atagttatat gcattggtac    180
caacagaaac caggacagcc acccaaactc ctcatctatc gtgcatccaa cctagaatct    240
ggggtccctg ccaggttcag tggcagtggg tctgggacag acttcaccct caacatccat    300
cctgtggagg aggaggatgc tgcaacctat tactgtcagc acagtaggga gcttccgctc    360
acgttcggtg ctgggaccaa gctggagctg aaacgg    396

<210> SEQ ID NO 25
<211> LENGTH: 336
<212> TYPE: DNA
<213> ORGANISM: Artificial Sequence
<220> FEATURE:
<223> OTHER INFORMATION: light chain variable region of antibody 1F5

<400> SEQUENCE: 25
gacattgtgc tgacacagtc tcctgcttcc ttagctgtat ctctggggca gagggccacc    60
atctcatgca gggccagcaa gagtgtcagt acatctggct atagttatat gcattggtac    120
caacagaaac caggacagcc acccaaactc ctcatctatc gtgcatccaa cctagaatct    180
ggggtccctg ccaggttcag tggcagtggg tctgggacag acttcaccct caacatccat    240
cctgtggagg aggaggatgc tgcaacctat tactgtcagc acagtaggga gcttccgctc    300
acgttcggtg ctgggaccaa gctggagctg aaacgg        336

<210> SEQ ID NO 26
<211> LENGTH: 160
<212> TYPE: PRT
<213> ORGANISM: Artificial Sequence
<220> FEATURE:
<223> OTHER INFORMATION: heavy chain of antibody 1F5

<400> SEQUENCE: 26

```
Met Ala Trp Val Trp Thr Leu Leu Phe Leu Met Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asp Tyr Ser Val His Trp Val Lys Gln Ala Pro Gly Lys Gly Leu
    50                  55                  60

Lys Trp Met Gly Trp Ile Asn Thr Glu Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Ala Gly Gly Asn Ala Phe Ala Tyr Trp Gly Gln
        115                 120                 125

Gly Thr Leu Val Thr Val Ser Ala Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160
```

<210> SEQ ID NO 27
<211> LENGTH: 117
<212> TYPE: PRT
<213> ORGANISM: Artificial Sequence
<220> FEATURE:
<223> OTHER INFORMATION: heavy chain variable region of antibody 1F5

<400> SEQUENCE: 27

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Val His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Ala Gly Gly Asn Ala Phe Ala Tyr Trp Gly Gln Gly Thr Leu
            100                 105                 110

Val Thr Val Ser Ala
        115
```

<210> SEQ ID NO 28
<211> LENGTH: 408

```
<212> TYPE: DNA
<213> ORGANISM: Artificial Sequence
<220> FEATURE:
<223> OTHER INFORMATION: heavy chain of antibody 1F5

<400> SEQUENCE: 28
atggcttggg tgtggacctt gctattcctg atggcagctg cccaaagtat ccaagcacag      60
atccagttgg tgcagtctgg acctgagctg aagaagcctg agagacagt caagatctcc     120 tgcaaggctt ctggttatac cttcacagac tattcagtgc actgggtgaa gcaggctcca    180
ggaaagggtt taaagtggat gggctggata acactgaga ctggtgagcc aacatatgca     240
gatgacttca agggacggtt tgccttctct ttggaaacct ctgccagcac tgcctatttg    300
cagatcaaca acctcaaaaa tgaggacacg gctacatatt tctgtgctag agcgggaggt    360
aacgcctttg cttactgggg ccaagggact ctggtcactg tctctgca                 408

<210> SEQ ID NO 29
<211> LENGTH: 351
<212> TYPE: DNA
<213> ORGANISM: Artificial Sequence
<220> FEATURE:
<223> OTHER INFORMATION: heavy chain variable region of antibody 1F5

<400> SEQUENCE: 29
cagatccagt tggtgcagtc tggacctgag ctgaagaagc tggagagac agtcaagatc      60 tcctgcaagg cttctggtta taccttcaca gactattcag tgcactgggt gaagcaggct    120
ccaggaaagg gtttaaagtg gatgggctgg ataaacactg agactggtga gccaacatat    180
gcagatgact tcaagggacg gtttgccttc tctttggaaa cctctgccag cactgcctat    240
ttgcagatca acaacctcaa aaatgaggac acggctacat atttctgtgc tagagcggga    300
ggtaacgcct ttgcttactg gggccaaggg actctggtca ctgtctctgc a              351

<210> SEQ ID NO 30
<211> LENGTH: 151
<212> TYPE: PRT
<213> ORGANISM: Artificial Sequence
<220> FEATURE:
<223> OTHER INFORMATION: light chain of antibody 8C7

<400> SEQUENCE: 30

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Pro
            20                  25                  30

Val Thr Pro Gly Glu Ser Val Ser Ile Ser Cys Arg Ser Ser Lys Ser
        35                  40                  45

Leu Leu Gln Ser Asn Gly Asn Thr Phe Leu Tyr Trp Phe Met Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Phe Thr Phe Gly Gly Gly Thr Lys
        115                 120                 125

Leu Glu Ile Lys Arg Ala Asp Ala Ala Pro Thr Val Ser Ile Phe Pro
    130                 135                 140
```

-continued

Pro Ser Ser Glu Gln Leu Thr
145                 150

<210> SEQ ID NO 31
<211> LENGTH: 113
<212> TYPE: PRT
<213> ORGANISM: Artificial Sequence
<220> FEATURE:
<223> OTHER INFORMATION: light chain variable region of antibody 8C7

<400> SEQUENCE: 31

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu Gln Ser
            20                  25                  30

Asn Gly Asn Thr Phe Leu Tyr Trp Phe Met Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

Arg

<210> SEQ ID NO 32
<211> LENGTH: 399
<212> TYPE: DNA
<213> ORGANISM: Artificial Sequence
<220> FEATURE:
<223> OTHER INFORMATION: light chain of antibody 8C7

<400> SEQUENCE: 32
atgaggtgcc tagctgagtt cctggggctg cttgtgctct ggatccctgg agccattggg        60
gatattgtga tgactcaggc tgcaccctct gtacctgtca ctcctggaga gtcagtatcc       120
atctcctgca ggtctagtaa gagtctcctg caaagtaatg gcaacacttt cttgtattgg       180
ttcatgcaga ggccaggcca gtctcctcag ctcctgatat atcggatgtc caaccttgcc       240
tcaggagtcc cagacaggtt cagtggcagt gggtcaggaa ctgctttcac actgagaatc       300
agtagagtgg aggctgagga tgtgggtgtt tattactgta tgcaacatct agaatatcct       360
ttcacgttcg gagggggac caagctggaa ataaaacgg                              399

<210> SEQ ID NO 33
<211> LENGTH: 339
<212> TYPE: DNA
<213> ORGANISM: Artificial Sequence
<220> FEATURE:
<223> OTHER INFORMATION: light chain variable region of antibody 8C7

<400> SEQUENCE: 33
gatattgtga tgactcaggc tgcaccctct gtacctgtca ctcctggaga gtcagtatcc        60
atctcctgca ggtctagtaa gagtctcctg caaagtaatg gcaacacttt cttgtattgg       120
ttcatgcaga ggccaggcca gtctcctcag ctcctgatat atcggatgtc caaccttgcc       180
tcaggagtcc cagacaggtt cagtggcagt gggtcaggaa ctgctttcac actgagaatc       240

```
agtagagtgg aggctgagga tgtgggtgtt tattactgta tgcaacatct agaatatcct    300
ttcacgttcg gagggggggac caagctggaa ataaaacgg                          339
```

<210> SEQ ID NO 34
<211> LENGTH: 155
<212> TYPE: PRT
<213> ORGANISM: Artificial Sequence
<220> FEATURE:
<223> OTHER INFORMATION: heavy chain of antibody 8C7

<400> SEQUENCE: 34

```
Met Asp Trp Leu Trp Asn Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asn Thr Gly Glu Pro Thr Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Ser Gly Gly Ser Ser Pro Phe Ala Tyr Trp Gly
        115                 120                 125

Gln Gly Thr Leu Val Thr Val Ser Ala Ala Lys Thr Thr Pro Pro Ser
    130                 135                 140

Val Tyr Pro Leu Ala Pro Gly Ser Ala Ala Gln
145                 150                 155
```

<210> SEQ ID NO 35
<211> LENGTH: 118
<212> TYPE: PRT
<213> ORGANISM: Artificial Sequence
<220> FEATURE:
<223> OTHER INFORMATION: heavy chain variable region of antibody 8C7

<400> SEQUENCE: 35

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Ser Gly Gly Ser Ser Pro Phe Ala Tyr Trp Gly Gln Gly Thr
            100                 105                 110

Leu Val Thr Val Ser Ala
        115
```

-continued

```
<210> SEQ ID NO 36
<211> LENGTH: 411
<212> TYPE: DNA
<213> ORGANISM: Artificial Sequence
<220> FEATURE:
<223> OTHER INFORMATION: heavy chain of antibody 8C7

<400> SEQUENCE: 36
atggattggc tgtggaactt gctattcctg atggcagctg cccaaagtat ccaagcacag      60
atccagttgg tgcagtctgg acctgagctg aagaagcctg agagacagt caagatctcc     120 tgcaaggctt ctgggtatac cttcacaaac tatggaatga actgggtgaa gcaggctcca    180
ggaaagggtt taaagtggat gggctggata acaccaaca ctggagagcc aacatatgct     240
gaagagttca agggacggtt tgccttctct ttggaaacct gccagcac tgcctatttg      300 cagatcaaca acctcaaaaa tgaggacacg gctacatatt tctgtgcaag atcgggcggt    360
agtagccctt ttgcttactg gggccaaggg actctggtca ctgtctctgc a             411

<210> SEQ ID NO 37
<211> LENGTH: 354
<212> TYPE: DNA
<213> ORGANISM: Artificial Sequence
<220> FEATURE:
<223> OTHER INFORMATION: heavy chain variable region of antibody 8C7

<400> SEQUENCE: 37
cagatccagt tggtgcagtc tggacctgag ctgaagaagc ctggagagac agtcaagatc      60
tcctgcaagg cttctgggta ccttcaca aactatggaa tgaactgggt gaagcaggct      120
ccaggaaagg gtttaaagtg gatgggctgg ataaacacca cactggaga gccaacatat     180 gctgaagagt tcaagggacg gtttgccttc tctttggaaa cctctgccag cactgcctat    240
ttgcagatca acaacctcaa aaatgaggac acggctacat atttctgtgc aagatcgggc    300
ggtagtagcc ttttgctta ctggggccaa gggactctgg tcactgtctc tgca           354

<210> SEQ ID NO 38
<211> LENGTH: 7
<212> TYPE: PRT
<213> ORGANISM: Homo sapiens

<400> SEQUENCE: 38

Arg Ser Glu Ala Ser Glu Gly
 1               5

<210> SEQ ID NO 39
<211> LENGTH: 5
<212> TYPE: PRT
<213> ORGANISM: Homo sapiens

<400> SEQUENCE: 39

Arg Gln Asp Gly Val
 1               5

<210> SEQ ID NO 40
<211> LENGTH: 5
<212> TYPE: PRT
<213> ORGANISM: Homo sapiens

<400> SEQUENCE: 40

Leu Pro Asp Gly Asn
 1               5
```

```
<210> SEQ ID NO 41
<211> LENGTH: 6
<212> TYPE: PRT
<213> ORGANISM: Homo sapiens

<400> SEQUENCE: 41

Gln Gly Glu Glu Gln Arg
1               5

<210> SEQ ID NO 42
<211> LENGTH: 6
<212> TYPE: PRT
<213> ORGANISM: Homo sapiens

<400> SEQUENCE: 42

Arg Gly Glu Glu Gln Arg
1               5

<210> SEQ ID NO 43
<211> LENGTH: 7
<212> TYPE: PRT
<213> ORGANISM: Homo sapiens

<400> SEQUENCE: 43

Cys Ser Glu Val Ser Glu Gly
1               5

<210> SEQ ID NO 44
<211> LENGTH: 5
<212> TYPE: PRT
<213> ORGANISM: Homo sapiens

<400> SEQUENCE: 44

Arg Gln Asp Gly Val
1               5

<210> SEQ ID NO 45
<211> LENGTH: 5
<212> TYPE: PRT
<213> ORGANISM: Homo sapiens

<400> SEQUENCE: 45

Leu Pro Asp Gly Asn
1               5

<210> SEQ ID NO 46
<211> LENGTH: 7
<212> TYPE: PRT
<213> ORGANISM: Homo sapiens

<400> SEQUENCE: 46

Arg Gln Gly Glu Glu Gln Arg
1               5

<210> SEQ ID NO 47
<211> LENGTH: 7
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa is Arg or Cys
<220> FEATURE:
<221> NAME/KEY: VARIANT
<222> LOCATION: (3)..(3)
<223> OTHER INFORMATION: Xaa is Glu or Lys
<220> FEATURE:
```

```
<221> NAME/KEY: VARIANT
<222> LOCATION: (4)..(4)
<223> OTHER INFORMATION: Xaa is Ala or Val

<400> SEQUENCE: 47

Xaa Ser Xaa Xaa Ser Glu Gly
1               5

<210> SEQ ID NO 48
<211> LENGTH: 5
<212> TYPE: PRT
<213> ORGANISM: Homo sapiens
<220> FEATURE:
<221> NAME/KEY: VARIANT
<222> LOCATION: (5)..(5)
<223> OTHER INFORMATION: Xaa is Val or Leu

<400> SEQUENCE: 48

Arg Gln Asp Gly Xaa
1               5

<210> SEQ ID NO 49
<211> LENGTH: 7
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa is Arg or Cys
<220> FEATURE:
<221> NAME/KEY: VARIANT
<222> LOCATION: (2)..(2)
<223> OTHER INFORMATION: Xaa is Gln, Arg, or Glu
<220> FEATURE:
<221> NAME/KEY: VARIANT
<222> LOCATION: (7)..(7)
<223> OTHER INFORMATION: Xaa is Arg, Ser, or Lys

<400> SEQUENCE: 49

Xaa Xaa Gly Glu Glu Gln Xaa
1               5

<210> SEQ ID NO 50
<211> LENGTH: 5
<212> TYPE: PRT
<213> ORGANISM: Homo sapiens

<400> SEQUENCE: 50

Leu Pro Asp Gly Asn
1               5

<210> SEQ ID NO 51
<211> LENGTH: 6
<212> TYPE: PRT
<213> ORGANISM: Homo sapiens

<400> SEQUENCE: 51

Asn Gly Thr Tyr Gln Thr
1               5

<210> SEQ ID NO 52
<211> LENGTH: 93
<212> TYPE: PRT
<213> ORGANISM: Homo sapiens

<400> SEQUENCE: 52

Val Pro Pro Met Val Asn Val Thr Arg Ser Glu Ala Ser Glu Gly Asn
1               5                   10                  15
```

Ile Thr Val Thr Cys Arg Ala Ser Gly Phe Tyr Pro Trp Asn Ile Thr
            20                  25                  30

Leu Ser Trp Arg Gln Asp Gly Val Ser Leu Ser His Asp Thr Gln Gln
            35                  40                  45

Trp Gly Asp Val Leu Pro Asp Gly Asn Gly Thr Tyr Gln Thr Trp Val
 50                  55                  60

Ala Thr Arg Ile Cys Gln Gly Glu Glu Gln Arg Phe Thr Cys Tyr Met
 65                  70                  75                  80

Glu His Ser Gly Asn His Ser Thr His Pro Val Pro Ser
                 85                  90

<210> SEQ ID NO 53
<211> LENGTH: 32
<212> TYPE: PRT
<213> ORGANISM: Homo sapiens

<400> SEQUENCE: 53

Thr Trp Val Ala Thr Arg Ile Cys Gln Gly Glu Glu Gln Arg Phe Thr
 1               5                  10                  15

Cys Tyr Met Glu His Ser Gly Asn His Ser Thr His Pro Val Pro Ser
            20                  25                  30

<210> SEQ ID NO 54
<211> LENGTH: 85
<212> TYPE: PRT
<213> ORGANISM: Homo sapiens

<400> SEQUENCE: 54

Arg Ser Glu Ala Ser Glu Gly Asn Ile Thr Val Thr Cys Arg Ala Ser
 1               5                  10                  15

Gly Phe Tyr Pro Trp Asn Ile Thr Leu Ser Trp Arg Gln Asp Gly Val
            20                  25                  30

Ser Leu Ser His Asp Thr Gln Gln Trp Gly Asp Val Leu Pro Asp Gly
            35                  40                  45

Asn Gly Thr Tyr Gln Thr Trp Val Ala Thr Arg Ile Cys Gln Gly Glu
 50                  55                  60

Glu Gln Arg Phe Thr Cys Tyr Met Glu His Ser Gly Asn His Ser Thr
 65                  70                  75                  80

His Pro Val Pro Ser
             85

<210> SEQ ID NO 55
<211> LENGTH: 81
<212> TYPE: PRT
<213> ORGANISM: Homo sapiens

<400> SEQUENCE: 55

Arg Ser Glu Ala Ser Glu Gly Asn Ile Thr Val Thr Cys Arg Ala Ser
 1               5                  10                  15

Gly Phe Tyr Pro Trp Asn Ile Thr Leu Ser Trp Arg Gln Asp Gly Val
            20                  25                  30

Ser Leu Ser His Asp Thr Gln Gln Trp Gly Asp Val Leu Pro Asp Gly
            35                  40                  45

Asn Gly Thr Tyr Gln Thr Trp Val Ala Thr Arg Ile Cys Gln Gly Glu
 50                  55                  60

Glu Gln Arg Phe Thr Cys Tyr Met Glu His Ser Gly Asn His Ser Thr
 65                  70                  75                  80

His

<210> SEQ ID NO 56
<211> LENGTH: 67
<212> TYPE: PRT
<213> ORGANISM: Homo sapiens

<400> SEQUENCE: 56

Arg Ser Glu Ala Ser Glu Gly Asn Ile Thr Val Thr Cys Arg Ala Ser
1               5                   10                  15

Gly Phe Tyr Pro Trp Asn Ile Thr Leu Ser Trp Arg Gln Asp Gly Val
            20                  25                  30

Ser Leu Ser His Asp Thr Gln Gln Trp Gly Asp Val Leu Pro Asp Gly
        35                  40                  45

Asn Gly Thr Tyr Gln Thr Trp Val Ala Thr Arg Ile Cys Gln Gly Glu
    50                  55                  60

Glu Gln Arg
65

<210> SEQ ID NO 57
<211> LENGTH: 93
<212> TYPE: PRT
<213> ORGANISM: Homo sapiens

<400> SEQUENCE: 57

Val Pro Pro Met Val Asn Val Thr Cys Ser Glu Val Ser Glu Gly Asn
1               5                   10                  15

Ile Thr Val Thr Cys Arg Ala Ser Ser Phe Tyr Pro Arg Asn Ile Thr
            20                  25                  30

Leu Thr Trp Arg Gln Asp Gly Val Ser Leu Ser His Asn Thr Gln Gln
        35                  40                  45

Trp Gly Asp Val Leu Pro Asp Gly Asn Gly Thr Tyr Gln Thr Trp Val
    50                  55                  60

Ala Thr Arg Ile Arg Gln Gly Glu Glu Gln Arg Phe Thr Cys Tyr Met
65                  70                  75                  80

Glu His Ser Gly Asn His Gly Thr His Pro Val Pro Ser
                85                  90

<210> SEQ ID NO 58
<211> LENGTH: 32
<212> TYPE: PRT
<213> ORGANISM: Homo sapiens

<400> SEQUENCE: 58

Thr Trp Val Ala Thr Arg Ile Arg Gln Gly Glu Glu Gln Arg Phe Thr
1               5                   10                  15

Cys Tyr Met Glu His Ser Gly Asn His Gly Thr His Pro Val Pro Ser
            20                  25                  30

<210> SEQ ID NO 59
<211> LENGTH: 85
<212> TYPE: PRT
<213> ORGANISM: Homo sapiens

<400> SEQUENCE: 59

Cys Ser Glu Val Ser Glu Gly Asn Ile Thr Val Thr Cys Arg Ala Ser
1               5                   10                  15

Ser Phe Tyr Pro Arg Asn Ile Thr Leu Thr Trp Arg Gln Asp Gly Val
            20                  25                  30

Ser Leu Ser His Asn Thr Gln Gln Trp Gly Asp Val Leu Pro Asp Gly
         35                  40                  45

Asn Gly Thr Tyr Gln Thr Trp Val Ala Thr Arg Ile Arg Gln Gly Glu
    50                  55                  60

Glu Gln Arg Phe Thr Cys Tyr Met Glu His Ser Gly Asn His Gly Thr
65                  70                  75                  80

His Pro Val Pro Ser
                85

<210> SEQ ID NO 60
<211> LENGTH: 81
<212> TYPE: PRT
<213> ORGANISM: Homo sapiens

<400> SEQUENCE: 60

Cys Ser Glu Val Ser Glu Gly Asn Ile Thr Val Thr Cys Arg Ala Ser
1               5                   10                  15

Ser Phe Tyr Pro Arg Asn Ile Thr Leu Thr Trp Arg Gln Asp Gly Val
            20                  25                  30

Ser Leu Ser His Asn Thr Gln Gln Trp Gly Asp Val Leu Pro Asp Gly
        35                  40                  45

Asn Gly Thr Tyr Gln Thr Trp Val Ala Thr Arg Ile Arg Gln Gly Glu
    50                  55                  60

Glu Gln Arg Phe Thr Cys Tyr Met Glu His Ser Gly Asn His Gly Thr
65                  70                  75                  80

His

<210> SEQ ID NO 61
<211> LENGTH: 67
<212> TYPE: PRT
<213> ORGANISM: Homo sapiens

<400> SEQUENCE: 61

Cys Ser Glu Val Ser Glu Gly Asn Ile Thr Val Thr Cys Arg Ala Ser
1               5                   10                  15

Ser Phe Tyr Pro Arg Asn Ile Thr Leu Thr Trp Arg Gln Asp Gly Val
            20                  25                  30

Ser Leu Ser His Asn Thr Gln Gln Trp Gly Asp Val Leu Pro Asp Gly
        35                  40                  45

Asn Gly Thr Tyr Gln Thr Trp Val Ala Thr Arg Ile Arg Gln Gly Glu
    50                  55                  60

Glu Gln Arg
65

<210> SEQ ID NO 62
<211> LENGTH: 15
<212> TYPE: PRT
<213> ORGANISM: Hepatitis B virus

<400> SEQUENCE: 62

Phe Phe Leu Leu Thr Arg Ile Leu Thr Ile Pro Gln Ser Leu Asp
1               5                   10                  15

<210> SEQ ID NO 63
<211> LENGTH: 27
<212> TYPE: PRT
<213> ORGANISM: Bordetella pertussis

<400> SEQUENCE: 63

Lys Lys Leu Arg Arg Leu Leu Tyr Met Ile Tyr Met Ser Gly Leu Ala
1               5                   10                  15

Val Arg Val His Val Ser Lys Glu Glu Gln Tyr
            20                  25

<210> SEQ ID NO 64
<211> LENGTH: 17
<212> TYPE: PRT
<213> ORGANISM: Clostridium tetani

<400> SEQUENCE: 64

Lys Lys Gln Tyr Ile Lys Ala Asn Ser Lys Phe Ile Gly Ile Thr Glu
1               5                   10                  15

Leu

<210> SEQ ID NO 65
<211> LENGTH: 22
<212> TYPE: PRT
<213> ORGANISM: Clostridium tetani

<400> SEQUENCE: 65

Lys Lys Phe Asn Asn Phe Thr Val Ser Phe Trp Leu Arg Val Pro Lys
1               5                   10                  15

Val Ser Ala Ser His Leu
            20

<210> SEQ ID NO 66
<211> LENGTH: 15
<212> TYPE: PRT
<213> ORGANISM: Bordetella pertussis

<400> SEQUENCE: 66

Tyr Met Ser Gly Leu Ala Val Arg Val His Val Ser Lys Glu Glu
1               5                   10                  15

<210> SEQ ID NO 67
<211> LENGTH: 27
<212> TYPE: PRT
<213> ORGANISM: Artificial Sequence
<220> FEATURE:
<223> OTHER INFORMATION: Synthetic construct

<400> SEQUENCE: 67

Tyr Asp Pro Asn Tyr Leu Arg Thr Asp Ser Asp Lys Asp Arg Phe Leu
1               5                   10                  15

Gln Thr Met Val Lys Leu Phe Asn Arg Ile Lys
            20                  25

<210> SEQ ID NO 68
<211> LENGTH: 24
<212> TYPE: PRT
<213> ORGANISM: Artificial Sequence
<220> FEATURE:
<223> OTHER INFORMATION: Synthetic construct

<400> SEQUENCE: 68

Gly Ala Tyr Ala Arg Cys Pro Asn Gly Thr Arg Ala Leu Thr Val Ala
1               5                   10                  15

Glu Leu Arg Gly Asn Ala Glu Leu
            20

<210> SEQ ID NO 69
<211> LENGTH: 15

```
<212> TYPE: PRT
<213> ORGANISM: Artificial Sequence
<220> FEATURE:
<223> OTHER INFORMATION: Synthetic construct

<400> SEQUENCE: 69

Leu Ser Glu Ile Lys Gly Val Ile Val His Arg Leu Glu Gly Val
1               5                   10                  15

<210> SEQ ID NO 70
<211> LENGTH: 20
<212> TYPE: PRT
<213> ORGANISM: Artificial Sequence
<220> FEATURE:
<223> OTHER INFORMATION: Synthetic construct

<400> SEQUENCE: 70

Gly Ile Leu Glu Ser Arg Gly Ile Lys Ala Arg Ile Thr His Val Asp
1               5                   10                  15

Thr Glu Ser Tyr
            20

<210> SEQ ID NO 71
<211> LENGTH: 17
<212> TYPE: PRT
<213> ORGANISM: Clostridium tetani

<400> SEQUENCE: 71

Trp Val Arg Asp Ile Ile Asp Asp Phe Thr Asn Glu Ser Ser Gln Lys
1               5                   10                  15

Thr

<210> SEQ ID NO 72
<211> LENGTH: 16
<212> TYPE: PRT
<213> ORGANISM: Clostridium tetani

<400> SEQUENCE: 72

Asp Val Ser Thr Ile Val Pro Tyr Ile Gly Pro Ala Leu Asn His Val
1               5                   10                  15

<210> SEQ ID NO 73
<211> LENGTH: 109
<212> TYPE: PRT
<213> ORGANISM: Artificial Sequence
<220> FEATURE:
<223> OTHER INFORMATION: Synthetic construct

<400> SEQUENCE: 73

Met Glu Phe Val Pro Pro Met Val Asn Val Thr Arg Ser Glu Ala Ser
1               5                   10                  15

Glu Gly Asn Ile Thr Val Thr Cys Arg Ala Ser Gly Phe Tyr Pro Trp
                20                  25                  30

Asn Ile Thr Leu Ser Trp Arg Gln Asp Gly Val Ser Leu Ser His Asp
            35                  40                  45

Thr Gln Gln Trp Gly Asp Val Leu Pro Asp Gly Asn Gly Thr Tyr Gln
        50                  55                  60

Thr Trp Val Ala Thr Arg Ile Cys Gln Gly Glu Gln Arg Phe Thr
65                  70                  75                  80

Cys Tyr Met Glu His Ser Gly Asn His Ser Thr His Pro Val Pro Ser
                85                  90                  95

Glu Asn Leu Tyr Phe Gln Gly His His His His His His
```

```
                    100                 105

<210> SEQ ID NO 74
<211> LENGTH: 48
<212> TYPE: PRT
<213> ORGANISM: Artificial Sequence
<220> FEATURE:
<223> OTHER INFORMATION: Synthetic construct

<400> SEQUENCE: 74

Met Glu Phe Thr Trp Val Ala Thr Arg Ile Cys Gln Gly Glu Glu Gln
1               5                   10                  15

Arg Phe Thr Cys Tyr Met Glu His Ser Gly Asn His Ser Thr His Pro
            20                  25                  30

Val Pro Ser Glu Asn Leu Tyr Phe Gln Gly His His His His His His
        35                  40                  45

<210> SEQ ID NO 75
<211> LENGTH: 101
<212> TYPE: PRT
<213> ORGANISM: Artificial Sequence
<220> FEATURE:
<223> OTHER INFORMATION: Synthetic construct

<400> SEQUENCE: 75

Met Glu Phe Arg Ser Glu Ala Ser Glu Gly Asn Ile Thr Val Thr Cys
1               5                   10                  15

Arg Ala Ser Gly Phe Tyr Pro Trp Asn Ile Thr Leu Ser Trp Arg Gln
            20                  25                  30

Asp Gly Val Ser Leu Ser His Asp Thr Gln Gln Trp Gly Asp Val Leu
        35                  40                  45

Pro Asp Gly Asn Gly Thr Tyr Gln Thr Trp Val Ala Thr Arg Ile Cys
    50                  55                  60

Gln Gly Glu Glu Gln Arg Phe Thr Cys Tyr Met Glu His Ser Gly Asn
65                  70                  75                  80

His Ser Thr His Pro Val Pro Ser Glu Asn Leu Tyr Phe Gln Gly His
                85                  90                  95

His His His His His
            100

<210> SEQ ID NO 76
<211> LENGTH: 97
<212> TYPE: PRT
<213> ORGANISM: Artificial Sequence
<220> FEATURE:
<223> OTHER INFORMATION: Synthetic construct

<400> SEQUENCE: 76

Met Glu Phe Arg Ser Glu Ala Ser Glu Gly Asn Ile Thr Val Thr Cys
1               5                   10                  15

Arg Ala Ser Gly Phe Tyr Pro Trp Asn Ile Thr Leu Ser Trp Arg Gln
            20                  25                  30

Asp Gly Val Ser Leu Ser His Asp Thr Gln Gln Trp Gly Asp Val Leu
        35                  40                  45

Pro Asp Gly Asn Gly Thr Tyr Gln Thr Trp Val Ala Thr Arg Ile Cys
    50                  55                  60

Gln Gly Glu Glu Gln Arg Phe Thr Cys Tyr Met Glu His Ser Gly Asn
65                  70                  75                  80

His Ser Thr His Glu Asn Leu Tyr Phe Gln Gly His His His His
                85                  90                  95
```

His

<210> SEQ ID NO 77
<211> LENGTH: 83
<212> TYPE: PRT
<213> ORGANISM: Artificial Sequence
<220> FEATURE:
<223> OTHER INFORMATION: Synthetic construct

<400> SEQUENCE: 77

```
Met Glu Phe Arg Ser Glu Ala Ser Glu Gly Asn Ile Thr Val Thr Cys
1               5                   10                  15

Arg Ala Ser Gly Phe Tyr Pro Trp Asn Ile Thr Leu Ser Trp Arg Gln
            20                  25                  30

Asp Gly Val Ser Leu Ser His Asp Thr Gln Gln Trp Gly Asp Val Leu
        35                  40                  45

Pro Asp Gly Asn Gly Thr Tyr Gln Thr Trp Val Ala Thr Arg Ile Cys
    50                  55                  60

Gln Gly Glu Glu Gln Arg Glu Asn Leu Tyr Phe Gln Gly His His His
65                  70                  75                  80

His His His
```

<210> SEQ ID NO 78
<211> LENGTH: 109
<212> TYPE: PRT
<213> ORGANISM: Artificial Sequence
<220> FEATURE:
<223> OTHER INFORMATION: Synthetic construct

<400> SEQUENCE: 78

```
Met Glu Phe Val Pro Pro Met Val Asn Val Thr Cys Ser Glu Val Ser
1               5                   10                  15

Glu Gly Asn Ile Thr Val Thr Cys Arg Ala Ser Ser Phe Tyr Pro Arg
            20                  25                  30

Asn Ile Thr Leu Thr Trp Arg Gln Asp Gly Val Ser Leu Ser His Asn
        35                  40                  45

Thr Gln Gln Trp Gly Asp Val Leu Pro Asp Gly Asn Gly Thr Tyr Gln
    50                  55                  60

Thr Trp Val Ala Thr Arg Ile Arg Gln Gly Glu Glu Gln Arg Phe Thr
65                  70                  75                  80

Cys Tyr Met Glu His Ser Gly Asn His Gly Thr His Pro Val Pro Ser
                85                  90                  95

Glu Asn Leu Tyr Phe Gln Gly His His His His His
            100                 105
```

<210> SEQ ID NO 79
<211> LENGTH: 48
<212> TYPE: PRT
<213> ORGANISM: Artificial Sequence
<220> FEATURE:
<223> OTHER INFORMATION: Synthetic construct

<400> SEQUENCE: 79

```
Met Glu Phe Thr Trp Val Ala Thr Arg Ile Arg Gln Gly Glu Glu Gln
1               5                   10                  15

Arg Phe Thr Cys Tyr Met Glu His Ser Gly Asn His Gly Thr His Pro
            20                  25                  30

Val Pro Ser Glu Asn Leu Tyr Phe Gln Gly His His His His His His
        35                  40                  45
```

<210> SEQ ID NO 80
<211> LENGTH: 101
<212> TYPE: PRT
<213> ORGANISM: Artificial Sequence
<220> FEATURE:
<223> OTHER INFORMATION: Synthetic construct

<400> SEQUENCE: 80

Met Glu Phe Cys Ser Glu Val Ser Glu Gly Asn Ile Thr Val Thr Cys
1               5                   10                  15

Arg Ala Ser Ser Phe Tyr Pro Arg Asn Ile Thr Leu Thr Trp Arg Gln
            20                  25                  30

Asp Gly Val Ser Leu Ser His Asn Thr Gln Gln Trp Gly Asp Val Leu
        35                  40                  45

Pro Asp Gly Asn Gly Thr Tyr Gln Thr Trp Val Ala Thr Arg Ile Arg
    50                  55                  60

Gln Gly Glu Glu Gln Arg Phe Thr Cys Tyr Met Glu His Ser Gly Asn
65                  70                  75                  80

His Gly Thr His Pro Val Pro Ser Glu Asn Leu Tyr Phe Gln Gly His
                85                  90                  95

His His His His His
            100

<210> SEQ ID NO 81
<211> LENGTH: 97
<212> TYPE: PRT
<213> ORGANISM: Artificial Sequence
<220> FEATURE:
<223> OTHER INFORMATION: Synthetic construct

<400> SEQUENCE: 81

Met Glu Phe Cys Ser Glu Val Ser Glu Gly Asn Ile Thr Val Thr Cys
1               5                   10                  15

Arg Ala Ser Ser Phe Tyr Pro Arg Asn Ile Thr Leu Thr Trp Arg Gln
            20                  25                  30

Asp Gly Val Ser Leu Ser His Asn Thr Gln Gln Trp Gly Asp Val Leu
        35                  40                  45

Pro Asp Gly Asn Gly Thr Tyr Gln Thr Trp Val Ala Thr Arg Ile Arg
    50                  55                  60

Gln Gly Glu Glu Gln Arg Phe Thr Cys Tyr Met Glu His Ser Gly Asn
65                  70                  75                  80

His Gly Thr His Glu Asn Leu Tyr Phe Gln Gly His His His His His
                85                  90                  95

His

<210> SEQ ID NO 82
<211> LENGTH: 83
<212> TYPE: PRT
<213> ORGANISM: Artificial Sequence
<220> FEATURE:
<223> OTHER INFORMATION: Synthetic construct

<400> SEQUENCE: 82

Met Glu Phe Cys Ser Glu Val Ser Glu Gly Asn Ile Thr Val Thr Cys
1               5                   10                  15

Arg Ala Ser Ser Phe Tyr Pro Arg Asn Ile Thr Leu Thr Trp Arg Gln
            20                  25                  30

Asp Gly Val Ser Leu Ser His Asn Thr Gln Gln Trp Gly Asp Val Leu

```
                35                  40                  45
Pro Asp Gly Asn Gly Thr Tyr Gln Thr Trp Val Ala Thr Arg Ile Arg
         50                  55                  60
Gln Gly Glu Glu Gln Arg Glu Asn Leu Tyr Phe Gln Gly His His His
 65                  70                  75                  80

His His His
```

<210> SEQ ID NO 83
<211> LENGTH: 15
<212> TYPE: PRT
<213> ORGANISM: Artificial Sequence
<220> FEATURE:
<223> OTHER INFORMATION: CDR L1 of antibody 1F5

<400> SEQUENCE: 83

```
Arg Ala Ser Lys Ser Val Ser Thr Ser Gly Tyr Ser Tyr Met His
 1               5                  10                  15
```

<210> SEQ ID NO 84
<211> LENGTH: 7
<212> TYPE: PRT
<213> ORGANISM: Artificial Sequence
<220> FEATURE:
<223> OTHER INFORMATION: CDR L2 of antibody 1F5

<400> SEQUENCE: 84

```
Arg Ala Ser Asn Leu Glu Ser
 1               5
```

<210> SEQ ID NO 85
<211> LENGTH: 9
<212> TYPE: PRT
<213> ORGANISM: Artificial Sequence
<220> FEATURE:
<223> OTHER INFORMATION: CDR L3 of antibody 1F5

<400> SEQUENCE: 85

```
Gln His Ser Arg Glu Leu Pro Leu Thr
 1               5
```

<210> SEQ ID NO 86
<211> LENGTH: 16
<212> TYPE: PRT
<213> ORGANISM: Artificial Sequence
<220> FEATURE:
<223> OTHER INFORMATION: CDR L1 of antibody 8C7

<400> SEQUENCE: 86

```
Arg Ser Ser Lys Ser Leu Leu Gln Ser Asn Gly Asn Thr Phe Leu Tyr
 1               5                  10                  15
```

<210> SEQ ID NO 87
<211> LENGTH: 7
<212> TYPE: PRT
<213> ORGANISM: Artificial Sequence
<220> FEATURE:
<223> OTHER INFORMATION: CDR L2 of antibody 8C7

<400> SEQUENCE: 87

```
Arg Met Ser Asn Leu Ala Ser
 1               5
```

<210> SEQ ID NO 88
<211> LENGTH: 9
<212> TYPE: PRT

```
<213> ORGANISM: Artificial Sequence
<220> FEATURE:
<223> OTHER INFORMATION: CDR L3 of antibody 8C7

<400> SEQUENCE: 88

Met Gln His Leu Glu Tyr Pro Phe Thr
1               5

<210> SEQ ID NO 89
<211> LENGTH: 5
<212> TYPE: PRT
<213> ORGANISM: Artificial Sequence
<220> FEATURE:
<223> OTHER INFORMATION: CDR H1 of antibody 1F5

<400> SEQUENCE: 89

Asp Tyr Ser Val His
1               5

<210> SEQ ID NO 90
<211> LENGTH: 17
<212> TYPE: PRT
<213> ORGANISM: Artificial Sequence
<220> FEATURE:
<223> OTHER INFORMATION: CDR H2 of antibody 1F5

<400> SEQUENCE: 90

Trp Ile Asn Thr Glu Thr Gly Glu Pro Thr Tyr Ala Asp Asp Phe Lys
1               5                   10                  15

Gly

<210> SEQ ID NO 91
<211> LENGTH: 8
<212> TYPE: PRT
<213> ORGANISM: Artificial Sequence
<220> FEATURE:
<223> OTHER INFORMATION: CDR H3 of antibody 1F5

<400> SEQUENCE: 91

Ala Gly Gly Asn Ala Phe Ala Tyr
1               5

<210> SEQ ID NO 92
<211> LENGTH: 5
<212> TYPE: PRT
<213> ORGANISM: Artificial Sequence
<220> FEATURE:
<223> OTHER INFORMATION: CDR H1 of antibody 8C7

<400> SEQUENCE: 92

Asn Tyr Gly Met Asn
1               5

<210> SEQ ID NO 93
<211> LENGTH: 17
<212> TYPE: PRT
<213> ORGANISM: Artificial Sequence
<220> FEATURE:
<223> OTHER INFORMATION: CDR H2 of antibody 8C7

<400> SEQUENCE: 93

Trp Ile Asn Thr Asn Thr Gly Glu Pro Thr Tyr Ala Glu Glu Phe Lys
1               5                   10                  15

Gly
```

```
<210> SEQ ID NO 94
<211> LENGTH: 9
<212> TYPE: PRT
<213> ORGANISM: Artificial Sequence
<220> FEATURE:
<223> OTHER INFORMATION: CDR H3 of antibody 8C7

<400> SEQUENCE: 94

Ser Gly Gly Ser Ser Pro Phe Ala Tyr
1               5

<210> SEQ ID NO 95
<211> LENGTH: 7
<212> TYPE: PRT
<213> ORGANISM: Artificial Sequence
<220> FEATURE:
<223> OTHER INFORMATION: CDR H1 of antibody 1F5

<400> SEQUENCE: 95

Gly Tyr Thr Phe Thr Asp Tyr
1               5

<210> SEQ ID NO 96
<211> LENGTH: 5
<212> TYPE: PRT
<213> ORGANISM: Artificial Sequence
<220> FEATURE:
<223> OTHER INFORMATION: CDR H2 of antibody 1F5

<400> SEQUENCE: 96

Asn Thr Glu Thr Gly
1               5

<210> SEQ ID NO 97
<211> LENGTH: 7
<212> TYPE: PRT
<213> ORGANISM: Artificial Sequence
<220> FEATURE:
<223> OTHER INFORMATION: CDR H1 of antibody 8C7

<400> SEQUENCE: 97

Gly Tyr Thr Phe Thr Asn Tyr
1               5

<210> SEQ ID NO 98
<211> LENGTH: 5
<212> TYPE: PRT
<213> ORGANISM: Artificial Sequence
<220> FEATURE:
<223> OTHER INFORMATION: CDR H2 of antibody 8C7

<400> SEQUENCE: 98

Asn Thr Asn Thr Gly
1               5

<210> SEQ ID NO 99
<211> LENGTH: 10
<212> TYPE: PRT
<213> ORGANISM: Artificial Sequence
<220> FEATURE:
<223> OTHER INFORMATION: CDR H1 of antibody 1F5

<400> SEQUENCE: 99

Gly Tyr Thr Phe Thr Asp Tyr Ser Val His
1               5                   10

<210> SEQ ID NO 100
```

```
<211> LENGTH: 9
<212> TYPE: PRT
<213> ORGANISM: Artificial Sequence
<220> FEATURE:
<223> OTHER INFORMATION: CDR H2 of antibody 1F5

<400> SEQUENCE: 100

Trp Ile Asn Thr Glu Thr Gly Glu Pro
1               5

<210> SEQ ID NO 101
<211> LENGTH: 10
<212> TYPE: PRT
<213> ORGANISM: Artificial Sequence
<220> FEATURE:
<223> OTHER INFORMATION: CDR H1 of antibody 8C7

<400> SEQUENCE: 101

Gly Tyr Thr Phe Thr Asn Tyr Gly Met Asn
1               5                   10

<210> SEQ ID NO 102
<211> LENGTH: 9
<212> TYPE: PRT
<213> ORGANISM: Artificial Sequence
<220> FEATURE:
<223> OTHER INFORMATION: CDR H2 of antibody 8C7

<400> SEQUENCE: 102

Trp Ile Asn Thr Asn Thr Gly Glu Pro
1               5

<210> SEQ ID NO 103
<211> LENGTH: 87
<212> TYPE: PRT
<213> ORGANISM: Artificial Sequence
<220> FEATURE:
<223> OTHER INFORMATION: Synthetic construct

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Trp Val
            20                  25                  30

Arg Gln Ala Pro Gly Gln Gly Leu Glu Trp Met Gly Arg Val Thr Ile
        35                  40                  45

Thr Ala Asp Thr Ser Thr Ser Thr Ala Tyr Met Glu Leu Ser Ser Leu
    50                  55                  60

Arg Ser Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 104
<211> LENGTH: 87
<212> TYPE: PRT
<213> ORGANISM: Artificial Sequence
<220> FEATURE:
<223> OTHER INFORMATION: Synthetic construct

<400> SEQUENCE: 104

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Trp Ile
```

```
                  20                  25                  30

Arg Gln Pro Gly Lys Gly Leu Glu Trp Ile Gly Arg Val Thr Ile
            35                  40                  45

Ser Val Asp Thr Ser Lys Asn Gln Phe Ser Leu Lys Leu Ser Ser Val
        50                  55                  60

Thr Ala Ala Asp Thr Ala Val Tyr Tyr Cys Ala Arg Trp Gly Gln Gly
65                  70                  75                  80

Thr Leu Val Thr Val Ser Ser
                85

<210> SEQ ID NO 105
<211> LENGTH: 87
<212> TYPE: PRT
<213> ORGANISM: Artificial Sequence
<220> FEATURE:
<223> OTHER INFORMATION: Synthetic construct

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Trp Val
            20                  25                  30

Arg Gln Ala Pro Gly Lys Gly Leu Glu Trp Val Ser Arg Phe Thr Ile
            35                  40                  45

Ser Arg Asp Asn Ser Lys Asn Thr Leu Tyr Leu Gln Met Asn Ser Leu
        50                  55                  60

Arg Ala Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 106
<211> LENGTH: 87
<212> TYPE: PRT
<213> ORGANISM: Artificial Sequence
<220> FEATURE:
<223> OTHER INFORMATION: Synthetic construct

<400> SEQUENCE: 106

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Trp Val
            20                  25                  30

Arg Gln Ala Pro Gly Gln Gly Leu Glu Trp Met Gly Arg Phe Val Phe
            35                  40                  45

Ser Leu Asp Thr Ser Val Ser Thr Ala Tyr Leu Gln Ile Ser Ser Leu
        50                  55                  60

Lys Ala Glu Asp Thr Ala Val Tyr Tyr Cys Ala Arg Trp Gly Gln Gly
65                  70                  75                  80

Thr Ser Leu Thr Val Ser Ser
                85

<210> SEQ ID NO 107
<211> LENGTH: 80
<212> TYPE: PRT
<213> ORGANISM: Artificial Sequence
<220> FEATURE:
<223> OTHER INFORMATION: Synthetic construct

<400> SEQUENCE: 107
```

```
Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
        35                  40                  45

Ser Gly Thr Asp Phe Thr Leu Thr Ile Ser Ser Leu Gln Pro Glu Asp
    50                  55                  60

Phe Ala Thr Tyr Tyr Cys Phe Gly Gln Gly Thr Lys Val Glu Ile Lys
65                  70                  75                  80

<210> SEQ ID NO 108
<211> LENGTH: 80
<212> TYPE: PRT
<213> ORGANISM: Artificial Sequence
<220> FEATURE:
<223> OTHER INFORMATION: Synthetic construct

<400> SEQUENCE: 108

Asp Ile Val Met Thr Gln Ser Pro Leu Ser Leu Pro Val Thr Pro Gly
1               5                   10                  15

Glu Pro Ala Ser Ile Ser Cys Trp Tyr Leu Gln Lys Pro Gly Gln Ser
            20                  25                  30

Pro Gln Leu Leu Ile Tyr Gly Val Pro Asp Arg Phe Ser Gly Ser Gly
        35                  40                  45

Ser Gly Thr Asp Phe Thr Leu Lys Ile Ser Arg Val Glu Ala Glu Asp
    50                  55                  60

Val Gly Val Tyr Tyr Cys Phe Gly Gln Gly Thr Lys Val Glu Ile Lys
65                  70                  75                  80

<210> SEQ ID NO 109
<211> LENGTH: 80
<212> TYPE: PRT
<213> ORGANISM: Artificial Sequence
<220> FEATURE:
<223> OTHER INFORMATION: Synthetic construct

<400> SEQUENCE: 109

Glu Ile Val Leu Thr Gln Ser Pro Gly Thr Leu Ser Leu Ser Pro Gly
1               5                   10                  15

Glu Arg Ala Thr Leu Ser Cys Trp Tyr Gln Gln Lys Pro Gly Gln Ala
            20                  25                  30

Pro Arg Leu Leu Ile Tyr Gly Ile Pro Asp Arg Phe Ser Gly Ser Gly
        35                  40                  45

Ser Gly Thr Asp Phe Thr Leu Thr Ile Ser Arg Leu Glu Pro Glu Asp
    50                  55                  60

Phe Ala Val Tyr Tyr Cys Phe Gly Gln Gly Thr Lys Val Glu Ile Lys
65                  70                  75                  80

<210> SEQ ID NO 110
<211> LENGTH: 79
<212> TYPE: PRT
<213> ORGANISM: Artificial Sequence
<220> FEATURE:
<223> OTHER INFORMATION: Synthetic construct

<400> SEQUENCE: 110

Asp Ile Val Met Thr Gln Ser Pro Asp Ser Leu Ala Val Ser Leu Gly
1               5                   10                  15
```

```
Glu Arg Ala Thr Ile Asn Cys Trp Tyr Gln Gln Lys Pro Gly Gln Pro
            20                  25                  30

Pro Lys Leu Leu Ile Tyr Gly Val Pro Asp Arg Phe Ser Gly Ser Gly
        35                  40                  45

Ser Gly Thr Asp Phe Thr Leu Thr Ile Ser Ser Leu Gln Ala Glu Asp
    50                  55                  60

Val Ala Val Tyr Tyr Cys Phe Gly Gln Gly Thr Lys Val Glu Ile
65                  70                  75
```

ANTIBODIES TO MICA AND MICB PROTEINS

CROSS REFERENCE TO RELATED APPLICATIONS

This application is a National Stage of International Application No. PCT/IB2014/001157, filed Mar. 15, 2014, which claims the benefit under 35 U.S.C. § 119(e) of U.S. Provisional Application No. 61/940,372, filed Feb. 15, 2014 and U.S. Provisional Application No. 61/801,329, filed Mar. 15, 2013. The contents of each cited priority application are incorporated herein by reference in their entireties.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "NBI-001_ST25.txt", a creation date of Mar. 15, 2014, and a size of 94 kilobytes. The Sequence Listing filed via EFS-Web is part of the specification and is hereby incorporated herein by reference in its entirety.

TECHNICAL FIELD

The present disclosure relates to antibodies, immunogens for generating the antibodies, and methods of using the antibodies for diagnostics and treatments.

BACKGROUND

Cancer rates worldwide are projected to continue to rise as more people live to an old age and as mass lifestyle changes occur in the developing world. Thus, cancer remains a major cause of human morbidity and mortality even with modern and more efficacious targeted oncology medicines. There is a continuing need for novel therapeutic strategies, especially those that can consistently provide or stimulate protective immunity as has been predicted for a number of immunotherapy treatments.

Oncology immunotherapy is designed to stimulate the body's immune system to fight tumors. Local immunotherapy injects a treatment into an affected area, thereby causing recruitment of immune cells, robust inflammation and consequently tumor shrinkage. Systemic immunotherapy treats the whole body by administering an agent, such as protein interferon alpha, that is also capable of shrinking tumors. Immunotherapy can also be considered non-specific if it improves overall cancer-fighting abilities by stimulating the entire immune system, and it can be considered targeted if the treatment directs the immune system to destroy cancer cells. These therapies, although relatively immature, have had success with treatments that introduce antibodies to the human body and which have resulted in the inhibition of cancer cell growth. An example of modern antibody immunotherapy drug is ipilimumab (Yervoy®), which targets CTLA4 surface proteins on immune cells, thereby interfering with specific regulatory brakes on the immune system and improving generalized immune attack towards tumor cells.

A key question surrounding the interplay between the immune system and transformed cancerous cells is how non-normal tumor cells can avoid detection and survive in the face of an apparently normal and intact immune defense system bent on destroying them. A significant amount of research concerning the innate immunosurveillance system and its interaction with stressed and transformed cells has suggested that this particular arm of the immune system is suppressed where moderate to advanced cancers are present. This is accomplished to a large extent by the release of decoy molecules from the tumor cells with the distinct objective of neutralizing the immunosurveillance system both locally and systemically. In fact, many viruses have evolved mechanisms for interfering with these defense systems and thus avoid immune detection during their infection cycles. It is desirable in consideration of therapies against cancers and viral infections to overcome the disease or pathogen instigated suppression of the immune system.

SUMMARY

The present disclosure provides compositions and methods for lowering the levels of circulating soluble MICA (sMICA) and/or soluble MICB (sMICB) proteins, which can have therapeutically beneficial effects by limiting the immunosuppressive effects of the sMIC proteins on immunosurveillance, thereby enhancing the immune response against disease cells. The composition herein relates to binding agents, particularly antibodies, that are capable of binding specifically to sMICA and/or sMICB but which do not bind specifically to full length MIC protein or forms of MIC protein bound to the cell membrane. In some embodiments, the antibodies bind specifically to immunologically hidden or cryptic regions, referred to as cryptic epitopes, of MICA and/or MICB protein, where the cryptic epitopes are revealed when these sMICA and/or sMICB ectodomains are released or shed from cell membranes.

Generally, in some embodiments, the binding agents can have insignificant autoimmune disease inducing activity. In some embodiments, the binding agents can have insignificant antagonistic activity towards binding of MICA and/or MICB to its cognate receptor NKG2D.

In some embodiments, the binding agents are capable of binding specifically to the alpha-3 domain of MICA and/or MICB protein but which do not bind specifically to full length MIC protein or forms of MIC protein bound to the cell membrane. In some embodiments, the binding agents are capable of binding specifically to a cryptic epitope on the alpha-3 domain of MICA and/or MICB protein, where the cryptic epitope to which the antibody binds is within the alpha-3 domain defined by amino acid residues 190 to 229;
    amino acid residues 190 to 238;
    amino acid residues 217 to 238;
    amino acid residues 243 to 256;
    amino acid residues 243 to 274; or
    amino acid residues 243 to 296/297
of MICA or MICB, where the amino acid positions are with respect to mature, processed MICA protein of the MICA*001 allele and to the mature, processed MICB protein of the MICB*001 allele, respectively.

In some embodiments, the binding agents are capable of binding specifically to a cryptic epitope on the alpha-3 domain of MICA, where the cryptic epitope is within an amino acid sequence selected from:

```
                                    (SEQ ID NO: 38)
   190_RSEASEG_196;

(SEQ ID NO: 39)
   217_RQDGV_221;
```

-continued

234_LPDGN_238; (SEQ ID NO: 40)
and

251_QGEEQR_256, (SEQ ID NO: 41)

where the amino acid positions are defined with respect to the mature, processed MICA protein of the MICA*001 allele.

In some embodiments, the binding agents are capable of binding specifically to a cryptic epitope on the alpha-3 domain of MICB, where the cryptic epitope is within an amino acid sequence selected from:

190_CSEVSEG_196; (SEQ ID NO: 43)

217_RQDGV_221; (SEQ ID NO: 44)

234_LPDGN_238; (SEQ ID NO: 45)
and

250_RQGEEQR_256, (SEQ ID NO: 46)

where the amino acid positions are defined with respect to the mature, processed MICB protein of the MICB*001 allele.

In some embodiments, the binding agents are capable of binding specifically to an epitope within a sequence defined by:

(a)
~$X^{41}$-S-$X^{43}$-$X^{44}$-S-E-G~, (SEQ ID NO: 47)

wherein $X^{41}$ is selected from R and C; $X^{43}$ is selected from E and K; and $X^{44}$ is selected from A and V;

(b)
~R-Q-D-G-$X^{B5}$~, (SEQ ID NO: 48)

wherein $X^{B5}$ is selected from V and L;

(c)
~$X^{D1}$-$X^{D2}$-G-E-E-Q-$X^{D7}$~, (SEQ ID NO: 49)

wherein $X^{D1}$ is selected from C or R; $X^{D2}$ is selected from Q, R and E; and $X^{D7}$ is selected from R, S and K; or (d)
~L-P-D-G-N~. (SEQ ID NO: 50)

In some embodiments, the binding agents comprise antibodies, where the antibodies can be polyclonal, monoclonal, chimeric, humanized, or fully human antibodies. In some embodiments, the binding agents can comprise fragments of the antibodies or single chain antibodies. In some embodiments, the antibodies can be bispecific or multispecific antibodies.

In some embodiments, the antibody comprises at least 1, 2, 3, 4, 5 or all 6 of the complementarity determining regions (CDRs) in the light chain variable region amino acid sequence of SEQ ID NO:23 and the heavy chain variable region amino acid sequence of SEQ ID NO:27. In some embodiments, the antibody comprises at least 1, 2, 3, 4, 5 or all 6 of the CDRs selected from: CDR L1 comprising an amino acid sequence RASKSVSTSGYSYMH (SEQ ID NO:83); CDR L2 comprising an amino acid sequence RASNLES (SEQ ID NO:84); CDR L3 comprising an amino acid sequence QHSRELPLT (SEQ ID NO:85); CDR H1 comprising an amino acid sequence DYSVH (SEQ ID NO:89), GYTFTDY (SEQ ID NO:95), or GYTFTDYSVH (SEQ ID NO:99); CDR H2 comprising an amino acid sequence WINTETGEPTYADDFKG (SEQ ID NO:90), NTETG (SEQ ID NO:96), or WINTETGEP (SEQ ID NO:100); and CDR H3 comprising an amino acid sequence AGGNAFAY (SEQ ID NO:91).

In some embodiments, the antibody comprises at least 1, 2, 3, 4, 5 or all 6 of the CDRs in the light chain variable region amino acid sequence of SEQ ID NO:31 and the heavy chain variable region amino acid sequence of SEQ ID NO:35. In some embodiments, the antibody comprises at least 1, 2, 3, 4, 5 or all 6 of the CDRs selected from: CDR L1 comprising an amino acid sequence RSSKSLLQSNGNTFLY (SEQ ID NO:86); CDR L2 comprising an amino acid sequence RMSNLAS (SEQ ID NO:87); CDR L3 comprising an amino acid sequence MQHLEYPFT (SEQ ID NO:88); CDR H1 comprising an amino acid sequence NYGMN (SEQ ID NO:92), GYTFTNY (SEQ ID NO:97), or GYTFTNYGMN (SEQ ID NO:101); CDR H2 comprising an amino acid sequence WINTNTGEPTYAEEFKG (SEQ ID NO:93), NTNTG (SEQ ID NO:98), or WINTNTGEP (SEQ ID NO:102); and CDR H3 comprising an amino acid sequence SGGSSPFAY (SEQ ID NO:94).

In some embodiments, the antibody comprises a light chain variable region VL comprising an amino acid sequence of SEQ ID NO:23 and a heavy chain variable region VH comprising an amino acid sequence of SEQ ID NO:27.

In some embodiments, the antibody comprises a light chain variable region VL comprising an amino acid sequence of SEQ ID NO:31 and a heavy chain variable region VH comprising an amino acid sequence of SEQ ID NO:35.

In another aspect, the present disclosure provides immunogens for preparing the antibodies that bind specifically to sMICA and/or sMICB, particularly to cryptic epitopes in the alpha-3 domain. In some embodiments, the immunogens can be coupled to carriers and prepared as compositions with appropriate adjuvants for preparing the binding agents of the disclosure.

In another aspect, the present disclosure provides methods of screening for antibodies that bind specifically to a cryptic epitope in the alpha-3 domain, as well as methods of preparing the antibodies.

The binding agents of the disclosure can be applied to various diagnostic and therapeutic uses. In some embodiments, the binding agents, such as the antibodies of the disclosure, can be used in diagnostic assays to determine the presence of sMICA and/or sMICB in biological samples, particularly samples obtained from subjects suspected of or diagnosed with a disease or disorder characterized by elevated levels of sMICA and/or sMICB.

In another aspect, the binding agents can be used for therapeutic applications. In some embodiments, the antibodies can be used in a method to reduce the levels of sMICA and/or sMICB by administering to a subject in need thereof an effective amount of the antibody agents of the disclosure. In some embodiments, the antibody agents can be used to treat a subject afflicted with a disease or disorder characterized by elevated levels of a sMIC protein. In these therapeutic applications, the binding agents disclosed herein can be administered in a therapeutically effective amount to a subject suffering from a disease or disorder characterized by elevated levels of sMICA and/or sMICB.

In some embodiments, the therapeutic methods can be used to treat a variety of disorders that are associated with elevated levels of sMICA and/or sMICB, such as a MIC tumor or a MIC viral infection. In some embodiments the MIC tumor comprises an epithelial cell tumor or a hematologic malignancy. In some embodiments, the tumors can comprise various types of epithelial tumors including, but not limited to, lung, breast, gastric, colon, ovarian, renal cell, prostate carcinomas, hepatocellular carcinomas, and melanoma. In some embodiments, the MIC hematologic malignancy can be selected from Acute Lymphoblastic Leukemia (ALL), Acute Myelogenous Leukemia (AML), Chronic Lymphocytic Leukemia (CLL), Chronic Myelogenous Leukemia (CML), Acute Monocytic Leukemia (AMol); lymphomas such as Hodgkin's lymphoma, and Non-Hodgkin's lymphoma; and Multiple Myelomas. The therapeutic antibodies can also be applied to certain viral infections, such as Respiratory Syncytial Virus (RSV) and Human Immunodeficiency Virus 1 (HIV-1) infections.

In some embodiments, the therapeutic application can be used in combination with other therapeutic agents used to treat the particular disorder associated with elevated sMIC levels, including combinations with chemotherapeutic agents; biologic agents, such as other therapeutic antibodies; and cancer vaccines, as further described in the detailed description that follow.

BRIEF DESCRIPTION OF THE FIGURES

FIG. 1A and FIG. 1B depict an exemplary amino acid sequence corresponding to a complete human MICA polypeptide (Allele *001: NCBI accession number NP_000238.1) (SEQ ID NO:1), and an exemplary amino acid sequence corresponding to a complete human MICB polypeptide (Allele *001: UniProtKB accession number Q29980.1) (SEQ ID NO:2), respectively.

FIG. 1C and FIG. 1D depict the amino acid sequence of the extracellular alpha-3 domain of MICA protein of the MICA*001 allele, amino acid residues 205-297 (SEQ ID NO:3); and the amino acid sequence of the extracellular alpha-3 domain of MICB protein of the MICB*001 allele, amino acid residues 205-297 (SEQ ID NO:4), respectively Amino acid numbering is based on the unprocessed MICA and MICB proteins. Amino acid numbering based on the processed, mature MICA*001 and MICB*001 corresponds to amino acid residues 182 to 274 for MICA and amino acid residues 182 to 274 for MICB.

FIG. 2 depicts an exemplary nucleotide sequence corresponding to the human MICA cDNA (Allele *001: NCBI accession no. NM_000247.2) (SEQ ID NO:5). The coding region is underlined.

FIG. 3 depicts an exemplary nucleotide sequence corresponding to human MICB cDNA (Allele *001: GenBank accession no. X91625.1) (SEQ ID NO:6). The coding region is underlined.

FIG. 4 depicts exemplary amino acid sequences of putative soluble MICA polypeptides (A—SEQ ID NO:7; B—SEQ ID NO:8; C—SEQ ID NO:9; D—SEQ ID NO:10; E—SEQ ID NO:11; F—SEQ ID NO:12; G—SEQ ID NO:13; H—SEQ ID NO:14).

FIG. 5 depicts exemplary amino acid sequences of putative soluble MICB polypeptides (A—SEQ ID NO:15; B—SEQ ID NO:16; C—SEQ ID NO:17; D—SEQ ID NO:18; E—SEQ ID NO:19; F—SEQ ID NO:20; G—SEQ ID NO:21).

FIG. 6 depicts the amino acid and nucleotide sequences of the light chain variable region and heavy chain variable region of antibody IF5. A—Amino acid sequence of the light chain variable region of antibody IF5, including the signal sequence (italics), variable region (bold, underlined) and part of the constant region (unmarked) (SEQ ID NO:22). B—Amino acid sequence of the light chain variable-region only, with CDRs delineated based on Kabat indicated (SEQ ID NO:23). C—Nucleotide sequence encoding the signal sequence and light chain variable region depicted in A above (SEQ ID NO:24). D—Nucleotide sequence encoding only the light chain variable region of antibody IF5 (SEQ ID NO:25). E—Amino acid sequence of the heavy chain variable region of antibody IF5, including the signal sequence (italics), variable region (bold, underlined) and part of the constant region (unmarked) (SEQ ID NO:26). F—Amino acid sequence of the heavy chain variable region only, with CDRs delineated based on Kabat indicated (SEQ ID NO:27). G—Nucleotide sequence encoding the signal sequence and light chain variable region depicted in E above (SEQ ID NO:28). H—Nucleotide sequence encoding only the heavy chain variable region of antibody IF5 (SEQ ID NO:29).

FIG. 7 depicts the amino acid and nucleotide sequences of the light chain variable region and heavy chain variable region of antibody 8C7. A—Amino acid sequence of the light chain variable region of antibody 8C7, including the signal sequence (italics), variable region (bold, underlined) and part of the constant region (unmarked) (SEQ ID NO:30). B—Amino acid sequence of the light chain variable region only, with CDRs delineated based on Kabat indicated (SEQ ID NO:31). C—Nucleotide sequence encoding the signal sequence and the light chain variable region depicted in A above (SEQ ID NO:32). D—Nucleotide sequence encoding only the light chain variable region of antibody 8C7 (SEQ ID NO:33). E—Amino acid sequence of the heavy chain variable region of antibody 8C7, including the signal sequence (italics), variable region (bold, underlined) and part of the constant region (unmarked) (SEQ ID NO:34). F—Amino acid sequence of the heavy chain variable-region only, with CDRs delineated based on Kabat indicated (SEQ ID NO:35). G—Nucleotide sequence encoding the signal sequence and the light chain variable region depicted in E above (SEQ ID NO:36). H—Nucleotide sequence encoding only the heavy chain variable region of antibody 8C7 (SEQ ID NO:37).

FIG. 8 depicts the amino acid sequences of human variable heavy chain consensus frameworks and human variable light chain consensus frameworks: human VH subgroup I consensus framework minus Kabat CDRs (SEQ ID NO:103); human VH subgroup II consensus framework minus Kabat CDRs (SEQ ID NO:104); human VH subgroup III consensus framework minus Kabat CDRs (SEQ ID NO:105); human VH subgroup VII consensus framework minus Kabat CDRs (SEQ ID NO:106); human VL subgroup I consensus framework minus Kabat CDRs (SEQ ID NO:107); human VL subgroup II consensus framework minus Kabat CDRs (SEQ ID NO:108); human VL subgroup III consensus framework minus Kabat CDRs (SEQ ID NO:109); and human VL subgroup IV consensus framework minus Kabat CDRs (SEQ ID NO:110).

FIG. 9 shows results of FACS analysis of antibody binding to heat-treated HCT116 colon carcinoma cells, which express MIC proteins on the cell surface. A—Positive control using antibody (IgG$_2$ isotype) that binds to an alpha-3 subdomain. B—Positive control using antibody that binds to alpha-1+alpha-2 subdomains (IgG$_1$ isotype). C—Binding of antibody clone 1F5. D—Binding of antibody clone 8C7. A and B show that control antibodies which bind to alpha-3 or alpha 1+2 subdomains also bind to heat-treated HCT116 colon carcinoma cells (peak near $10^2$ Yellow Fluorescence axis). C shows that 1F5 does not bind heat-treated HCT116 colon carcinoma cells (unbound antibody peak near $10^1$ Yellow Fluorescence axis). Similarly, D shows that antibody 8C7 does not bind heat-treated HCT116 colon carcinoma cells (unbound antibody peak near $10^1$ Yellow Fluorescence axis).

DETAILED DESCRIPTION

The present disclosure provides binding agents, particularly antibodies, that specifically recognize soluble forms of MHC class I chain-related gene A protein (MICA) and/or MHC class I chain-related gene B protein (MICB), use of such binding agents to treat diseases characterized by presence of elevated levels of soluble MICA (sMICA) and/or soluble MICB (sMICB), and use as diagnostic reagents for detecting the presence of soluble MIC proteins.

Before various embodiments of the present invention are further described, it is to be understood that this disclosure is not limited to particular embodiments described, as such may, of course, vary. It is also to be understood that the terminology used herein is for the purposes of describing particular embodiments only, and is not intended to be limiting.

It is also to be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In addition, the use of "or" means "and/or" unless stated otherwise. Similarly, "comprise," "comprises," "comprising," "include," "includes," and "including" are interchangeable and not intended to be limiting. Where descriptions of various embodiments use the term "comprising," those skilled in the art would understand that in some specific instances, an embodiment can be alternatively described using language "consisting essentially of" or "consisting of."

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Although any methods and materials similar or equivalent to those described herein can also be used in the practice or testing of the present invention, the preferred methods and materials are now described. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In some embodiments, methods recited herein may be carried out in any order of the recited events which is logically possible, as well as the recited order of events.

In the present disclosure, the abbreviations used for the genetically encoded amino acids herein are conventional and are as follows:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When the three-letter abbreviations are used, unless specifically preceded by an "L" or a "D" or clear from the context in which the abbreviation is used, the amino acid may be in either the L- or D-configuration about α-carbon (C$_\alpha$). For example, whereas "Ala" designates alanine without specifying the configuration about the α-carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When polypeptide and peptide sequences are presented as a string of one-letter or three-letter abbreviations (or mixtures thereof), the sequences are presented in the N→C direction in accordance with common convention.

The abbreviations used for the genetically encoding nucleosides are conventional and are as follows: adenosine (A); guanosine (G); cytidine (C); thymidine (T); and uridine (U). Unless specifically delineated, the abbreviated nucleotides may be either ribonucleosides or 2'-deoxyribonucleosides. The nucleosides may be specified as being either ribonucleosides or 2'-deoxyribonucleosides on an individual basis or on an aggregate basis. When specified on an individual basis, the one-letter abbreviation is preceded by either a "d" or an "r," where "d" indicates the nucleoside is a 2'-deoxyribonucleoside and "r" indicates the nucleoside is a ribonucleoside. For example, "dA" designates 2'-deoxyriboadenosine and "rA" designates riboadenosine. When specified on an aggregate basis, the particular nucleic acid or polynucleotide is identified as being either an RNA molecule or a DNA molecule. Nucleotides are abbreviated by adding a "p" to represent each phosphate, as well as whether the phosphates are attached to the 3'-position or the 5'-position of the sugar. Thus, 5'-nucleotides are abbreviated as "pN" and 3'-nucleotides are abbreviated as "Np," where "N" represents A, G, C, T or U. When nucleic acid sequences are presented as a string of one-letter abbreviations, the sequences are presented in the 5'→3' direction in accordance with common convention, and the phosphates are not indicated.

Unless defined otherwise, all technical and scientific terms used herein have the same meaning as commonly understood by one of ordinary skill in the art. Accordingly, the following terms are intended to have the following meanings.

As used herein, the term "antibody" is used in the broadest sense and refers to an immunoglobulin or fragment thereof, and encompasses any such polypeptide comprising an antigen-binding fragment or region of an antibody. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Immunoglobulin classes may also be further classified into sub-classes, including IgG subclasses $IgG_1$, $IgG_2$, $IgG_3$, and $IgG_4$; and IgA subclasses $IgA_1$ and $IgA_2$. The term includes, but is not limited to, polyclonal, monoclonal, monospecific, multispecific (e.g., bispecific antibodies), natural, humanized, human, chimeric, synthetic, recombinant, hybrid, mutated, grafted, antibody fragments (e.g., a portion of a full-length antibody, generally the antigen binding or variable region thereof, e.g., Fab, Fab', F(ab')2, and Fv fragments), and in vitro generated antibodies so long as they exhibit the desired biological activity. The term also includes single chain antibodies, e.g., single chain Fv (sFv or scFv) antibodies, in which a variable heavy and a variable light chain are joined together (directly or through a peptide linker) to form a continuous polypeptide.

As used herein, the term "isolated" refers to a change from a natural state, that is, changed and/or removed from its original environment. For example, a polynucleotide or polypeptide (e.g., antibody) naturally present in an organism is not "isolated," but the same polynucleotide or polypeptide when separated from a natural co-existing substance by the action of a human is "isolated." Thus, an "isolated antibody" is one which has been separated and/or recovered from a component of its natural environment.

As used herein, the term "purified antibody" refers to an antibody preparation in which the antibody is at least 80% or greater, at least 85% or greater, at least 90% or greater, at least 95% or greater by weight as compared to other contaminants (e.g., other proteins) in the preparation, such as by determination using SDS-PAGE under reducing or nonreducing conditions.

As used herein, the term "extracellular domain" and "ectodomain" are used interchangeably when used in reference to a membrane bound protein and refer to the portion of the protein that is exposed on the extracellular side of a lipid bilayer of a cell. In some embodiments, the extracellular domain of MICA is from amino acid residue at about 24 to about 299 of an unprocessed full length MICA protein, where the amino acid numbering is based on the MICA protein of the MICA*001 allele. In some embodiments, extracellular domain of MICB is from amino acid residue at about 24 to about 299 of an unprocessed full length MICB protein, where the amino acid numbering is based on the MICB protein of the MICB*001 allele. It is to be understood that the polypeptide region defining the extracellular domain of MICA and MICB is approximate and, in some embodiments, may extend to about amino acid residue 307. An exemplary unprocessed full length MICA protein of the MICA*001 allele is presented in FIG. 1A (SEQ ID NO:1), and an exemplary unprocessed full length MICB protein of the MICB*001 allele is presented in FIG. 1B (SEQ ID NO:2).

As used herein, the term "binds specifically" in the context of any binding agent, e.g., an antibody, refers to a binding agent that binds specifically to an antigen or epitope, such as with a high affinity, and does not significantly bind other unrelated antigens or epitopes.

As used herein, the term "functional" refers to a form of a molecule which possesses either the native biological activity of the naturally existing molecule of its type, or any specific desired activity, for example as judged by its ability to bind to ligand molecules. Examples of "functional" polypeptides include an antibody binding specifically to an antigen through its antigen-binding region.

As used herein, the term "Natural Killer Group 2D", "NKG2D" and "NKG2D receptor" refer to an activating cell surface molecule that is found on numerous types of immune cells, particularly NK cells, $CD8^+$ T cells (e.g., γδ $CD8^+$ T cells, and αβ $CD8^+$ T cells) and some $CD4^+$ T cells. NKG2D is also referred to as killer cell lectin-like receptor, subfamily C, member 4, or as KLRC4. The terms "NKG2D" and "NKG2D receptor" includes variants, isoforms, and species homologs of human NKG2D receptor (see, e.g., the isoforms described in Diefenbach et al., 2002, Nat Immunol. 3(12):1142-9). NKG2D is a type II transmembrane protein with an extracellular C-type (i.e., $Ca^{2+}$-binding) lectin-like domain but lacking the $Ca^{2+}$ binding site. It can form heterodimers with adapter proteins such as DAP10 or DAP12, and recognizes protein ligands that include MICA, MICB, ULBP1, ULBP2, ULBP3, ULBP4, ULBP5, and ULBP6. It is to be understood that any activity attributed herein to NKG2D, e.g., cell activation, recognition by antibodies, etc., can also refer to NKG2D-including complexes such as NKG2D-DAP10 or NKG2D-DAP12 heterodimers. Interaction of a NKG2D-bearing immune effector cell, for example an NK cell, with stressed or diseased cells expressing a NKG2D ligand, such as MICA or MICB, enhances the cellular immune response against the stressed/diseased cell.

As used herein, the term "MICA" refers to MHC class I chain-related gene A protein (MICA), including variants, isoforms, and species homologs of human MICA. Unlike HLA class I protein, the MICA protein does not associate with β2 microglobulin. MICA expression is stress induced, and MICA acts as a ligand for natural killer cell (NK) receptor NKG2D. MICA protein comprises three extracellular Ig-like domains, i.e., alpha-1, alpha-2 and alpha-3, a transmembrane domain, and an intracellular domain. The protein is expressed in cells of the gastric epithelium, endothelial cells and fibroblasts and in the cytoplasm of keratinocytes and monocytes. Exemplary sequences of MICA are available as NCBI accession nos. NP_000238.1 (allele MICA*001), presented in FIG. 1A (SEQ ID NO:1) of the present disclosure, and NP_001170990.1 (allele MICA*008.01). Other exemplary MICA sequences can be found in U.S. patent publication 20110311561, incorporated herein by reference.

As used herein, the term "MICB" refers to MHC class I chain-related gene B protein (MICB), including variants, isoforms, and species homologs of human MICB. Unlike HLA class I protein, the MICB protein does not associate with β2 microglobulin. MICB expression is stress induced, and MICB acts as a ligand for natural killer cell (NK) receptor NKG2D. MICB has about 84% sequence identity to MICA. MICB protein comprises three extracellular Ig-like domains, i.e., alpha-1, alpha-2 and alpha-3, a transmembrane domain, and an intracellular domain. The protein is expressed in the gastric epithelium, endothelial cells and fibroblasts and in the cytoplasm of keratinocytes and monocytes. An exemplary sequence of MICB is available as UniProtKB accession number Q29980.1, which is presented in FIG. 1B (SEQ ID NO:2) of the present disclosure. Other exemplary MICB sequences can be found in U.S. patent publication 20110311561, incorporated herein by reference.

As used herein, the term "soluble MICA" or "sMICA" refers to a MICA protein containing the alpha-1, alpha-2, and alpha-3 domains but which is not attached or tethered to a cell and thus exists extracellularly. Generally, soluble MICA lacks the transmembrane domain. In some embodiments, the sMICA is functional in binding to the NKG2D receptor. As used herein, sMICA encompasses forms released from cells by proteolysis, which forms can be variable because of non-specificity of the proteolytic process. Exemplary sMICA comprises a polypeptide containing amino acid residues from about 24 to about 297 of the unprocessed full length MICA presented in FIG. 1A (SEQ ID NO:1). Exemplary amino acid sequences of putative soluble MICA proteins are also presented in FIG. 4 (SEQ ID NOs:7-14).

As used herein, the term "soluble MICB" or "sMICB" refers to a MICB protein containing the alpha-1, alpha-2, and alpha-3 domains of the MICB protein but which is not attached or tethered to a cell and thus exists extracellularly. Generally, soluble MICB lacks the transmembrane domain. As used herein, sMICB encompasses forms released from cells by proteolysis, which forms can be variable because of non-specificity of the proteolytic process. Exemplary sMICB comprises a polypeptide of amino acid residues from about 24 to about 297 of the unprocessed full length MICB presented in FIG. 1B (SEQ ID NO:2). Exemplary amino acid sequences of putative soluble MICA proteins are also presented in FIG. 5 (SEQ ID NOs:15-21).

As used herein, the term "shedding" or "shed" in reference to a NKG2D ligand, such as MICA and MICB, refers to release of a soluble extracellular domain fragment of a NKG2D ligand from the cell surface of a cell that expresses the NKG2D ligand. Such shedding may be caused by proteolytic cleavage of cell surface NKG2D ligand resulting in release of an extracellular domain fragment from the cell surface. In some embodiments, the soluble extracellular domain or fragment thereof may be encoded by an alternate transcript.

As used herein, the term "full length MIC" refers to a MIC protein containing the alpha-1, alpha-2, and alpha-3 domains; the transmembrane domain; and the intracellular domain. "Unprocessed full length MIC protein" refers to a MIC protein that has not been processed following translation while a "full length mature MIC protein" or "full length processed MIC protein" refers to the processed form of the MIC protein, for example a MIC protein having a leader peptide removed. The full length unprocessed and the full length mature processed proteins can vary in length due to the existence of polymorphisms. In some embodiments, the total unprocessed length (containing a leader sequence) can range from about 332 to about 388 amino acids for MICA and, in some embodiments, is about 383 amino acids for MICB. In some embodiments, the unprocessed full length MIC protein can vary from about 332 to about 388 amino acids. A processed MIC protein (with leader sequences removed) can range from about 309 to about 365 amino acids for MICA and about 360 amino acids for MICB. Exemplary unprocessed full length MIC proteins are set forth in FIG. 1A (SEQ ID NO:1) for MICA and FIG. 1B (SEQ ID NO:2) for MICB. Other exemplary full length MICA and MICB sequences can be found in U.S. patent publication 20110311561 and International patent publication WO2013117647, incorporated herein by reference.

As used herein, the term "membrane bound form" in the context of a protein or polypeptide refers to the protein or polypeptide containing the extracellular domain or portions thereof attached to at least the transmembrane domain or other membrane attachment domain. A membrane bound form may or may not include the intracellular domain.

As used herein, the term "alpha-1 domain" of a MIC protein (e.g., MICA and MICB) refers to amino terminal proximal Ig-like region (i.e., G-like domain) on the extracellular domain of MICA and MICB proteins (see, e.g., Frigoul and Lefranc, 2005, Recent Res Devel Human Genet. 3:95-145; incorporated herein by reference). An exemplary alpha-1 domain of MICA contains amino acid residues from about 24 to about 108 of unprocessed MICA protein of the MICA*001 allele. An exemplary alpha-1 domain of MICB contains amino acid residues from about 24 to about 108 of unprocessed MICB protein of the MICB*001 allele.

As used herein, the term "alpha-2 domain" of a MIC protein (e.g., MICA and MICB) refers to the second Ig-like region (i.e., G-like domain) on the extracellular domain of MICA and MICB proteins (see, e.g., Frigoul and Lefranc, 2005, Recent Res Devel Human Genet. 3:95-145, incorporated herein by reference). An exemplary alpha-2 domain of MICA contains amino acid residues from about 109 to about 201 of unprocessed MICA protein of the MICA*001 allele. An exemplary alpha-2 domain of MICB protein contains amino acid residues from about 109 to about 201 of unprocessed MICB protein of the MICB*001 allele.

As used herein, the term "alpha-3 domain" of a MIC protein (e.g., MICA and MICB) refers to the transmembrane proximal region, also referred to as the C-like region on the extracellular domain of MICA and MICB proteins (see, e.g., Frigoul and Lefranc, 2005, Recent Res Devel Human Genet. 3:95-145, incorporated herein by reference). In some embodiments, the alpha-3 domain contains the disulfide bond formed between two cysteine residues in the alpha-3 domain. An exemplary alpha-3 domain of MICA contains amino acid residues from about 205 to about 296 or from about 205 to about 297 of unprocessed MICA protein of the MICA*001 allele. An exemplary alpha-3 domain of MICB protein contains amino acid residues from about 205 to about 296 or from about 205 to about 297 of unprocessed MICB protein of the MICB*001 allele.

As used herein, the term "insignificant autoimmune disease inducing" refers to the lack of a pathological autoimmune reaction inducing activity.

As used herein, the term "antigen" refers to a substance, such as a particular peptide or protein, which can bind to a specific antibody.

As used herein, the term "epitope" or "antigenic determinant" refers to that portion of an antigen capable of being recognized and specifically bound by a particular antibody. When the antigen is a polypeptide, epitopes can be formed from contiguous amino acids and/or noncontiguous amino acids juxtaposed by tertiary folding of a protein. Linear epitope is an epitope formed from contiguous amino acids on the linear sequence of amino acids. A linear epitope is typically retained upon protein denaturing. Conformational or structural epitope is an epitope composed of amino acid residues that are not contiguous and thus comprised of separated parts of the linear sequence of amino acids that are brought into proximity to one another by folding of the molecule, such as through secondary, tertiary, and/or quaternary structures. A conformational or structural epitope is typically lost upon protein denaturation. In some embodiments, an epitope can comprise at least 3, and more usually, at least 5 or 8-10 amino acids in a unique spatial conformation. Thus, an epitope as used herein encompasses a defined epitope in which an antibody binds only portions of the defined epitope. There are many methods known in the art for mapping and characterizing the location of epitopes on proteins, including solving the crystal structure of an antibody-antigen complex, competition assays, gene fragment expression assays, mutation assays, and synthetic peptide-based assays, as described, for example, in Using Antibodies: A Laboratory Manual, Chapter 11, Harlow and Lane, eds., Cold Spring Harbor Laboratory Press, Cold Spring Harbor, N.Y. (1999).

As used herein, the term "cryptic epitope" refers to an epitope that is not exposed for recognition by a binding agent within a native structure, but is capable of being recognized when there is a disruption of the native structure that exposes the cryptic epitope. In the context of a protein, a cryptic epitope refers to a protein sequence that is not exposed for recognition within a native protein, but is capable of being recognized by a binding agent when there is a disruption of the native protein structure or when the epitope is separate from the native protein. Sequences that are not exposed or are only partially exposed in the native structure are potential cryptic epitopes. If an epitope is not exposed, or only partially exposed, then it is likely buried within the interior of the molecule. Candidate cryptic epitopes can also be identified, for example, by examining the three-dimensional structure of a native protein. In some embodiments, structural disruptions capable of exposing cryptic epitopes include denaturation and proteolysis. Separation of the cryptic epitope from the native protein can occur by proteolysis, synthesis of a protein fragment containing the epitope, or release of an extracellular portion of the native protein from a membrane, such as a cell surface membrane.

As used herein, the term "polymorphic" or "polymorphism" refers to the occurrence of two or more forms of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long. A polymorphic protein refers to occurrence of two or more forms of the protein due to polymorphisms in the encoding gene sequence.

As used herein, the term "allele" refers to the specific gene sequence at a locus, which is the position occupied by a segment of a specific sequence of base pairs along a gene sequence of DNA.

As used herein, the term "protein," "polypeptide," or "peptide" denotes a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids. The polypeptide sequences are displayed herein in the conventional N-terminal to C-terminal orientation.

As used herein, the term "polynucleotide" and "nucleic acid" are used interchangeably herein and refer to two or more nucleosides that are covalently linked together. The polynucleotide may be wholly comprised ribonucleosides (i.e., an RNA), wholly comprised of 2' deoxyribonucleotides (i.e., a DNA) or mixtures of ribo- and 2' deoxyribonucleosides. The nucleosides will typically be linked together by sugar-phosphate linkages (sugar-phosphate backbone), but the polynucleotides may include one or more non-standard linkages. Non-limiting example of such non-standard linkages include phosphoramidates, phosphorothioates, and amides (see, e.g., Eckstein, F., Oligonucleotides and Analogues: A Practical Approach, Oxford University Press (1992)).

As used herein, the term "operably linked" or "operably associated" refers to a situation in which two or more polynucleotide sequences are positioned to permit their ordinary functionality. For example, a promoter is operably linked to a coding sequence if it is capable of controlling the expression of the sequence. Other control sequences, such as enhancers, ribosome binding or entry sites, termination signals, polyadenylation sequences, and signal sequences are also operably linked to permit their proper function in transcription or translation.

As used herein, the term "amino acid position" and "amino acid residue" are used interchangeably to refer to the position of an amino acid in a polypeptide chain. In some embodiments, the amino acid residue can be represented as "XN", where X represents the amino acid and the N represents its position in the polypeptide chain. Where two or more variations, e.g., polymorphisms, occur at the same amino acid position, the variations can be represented with a "I" separating the polymorphisms. A substitution of one amino acid residue with another amino acid residue at a specified residue position can be represented by XNY, where X represents the original amino acid, N represents the position in the polypeptide chain, and Y represents the replacement or substitute amino acid. When the terms are used to describe a polypeptide or peptide portion in reference to a larger polypeptide or protein, the first number referenced describes the position where the polypeptide or peptide begins (i.e., amino end) and the second referenced number describes where the polypeptide or peptide ends (i.e., carboxy end). For example, a peptide from amino acid position 190 to 196 of a processed full length MICA refers to a peptide in which its amino end is at position 190 and its carboxy end is at position 196 of the processed full length MICA protein.

As used herein, the term "polyclonal" antibody refers to a composition of different antibody molecules which is capable of binding to or reacting with several different specific antigenic determinants on the same or on different antigens. A polyclonal antibody can also be considered to be a "cocktail of monoclonal antibodies." The polyclonal antibodies may be of any origin, e g, chimeric, humanized, or fully human.

As used herein, the term "monoclonal antibody" refers to an antibody obtained from a population of substantially homogeneous antibodies, i.e., the individual antibodies comprising the population are identical except for possible naturally occurring mutations that may be present in minor amounts. Each monoclonal antibody is directed against a single determinant on the antigen. Monoclonal antibodies are highly specific. For example, the monoclonal antibodies to be used in accordance with the present disclosure can be made by the hybridoma method described by Kohler et al., 1975, Nature 256:495-7, or can be made by recombinant DNA methods. The monoclonal antibodies may also be isolated, e.g., from phage antibody libraries.

As used herein, the term "chimeric antibody" refers to an antibody made up of components from at least two different sources. A chimeric antibody can comprise a portion of an antibody derived from a first species fused to another molecule, e.g., a portion of an antibody derived from a second species. In some embodiments, a chimeric antibody comprises a portion of an antibody derived from a non-human animal, e.g., mouse or rat, fused to a portion of an antibody derived from a human. In some embodiments, a chimeric antibody comprises all or a portion of a variable region of an antibody derived from a non-human animal fused to a constant region of an antibody derived from a human.

As used herein, the term "humanized antibody" refers to an antibody that comprises a donor antibody binding specificity, e.g., the CDR regions of a donor antibody, such as a mouse monoclonal antibody, grafted onto human framework sequences. A "humanized antibody" typically binds to the same epitope as the donor antibody.

As used herein, the term "fully human antibody" or "human antibody" refers to an antibody that comprises human immunoglobulin protein sequences only. A fully human antibody may contain murine carbohydrate chains if produced in a mouse, in a mouse cell, or in a hybridoma derived from a mouse cell.

As used herein, the term "antibody fragment" or "antigen-binding moiety" refers to a portion of a full length antibody, generally the antigen binding or variable domain thereof. Examples of antibody fragments include Fab, Fab', F(ab')2, and Fv fragments; diabodies; linear antibodies; single-chain antibodies; and multispecific antibodies formed from antibody fragments that bind two or more different antigens. Several examples of antibody fragments containing increased binding stoichiometries or variable valencies (2, 3 or 4) include triabodies, trivalent antibodies and trimerbodies, tetrabodies, tandAbs®, di-diabodies and (sc(Fv)2)$_2$ molecules, and all can be used as binding agents to bind with high affinity and avidity to soluble antigens (see, e.g., Cuesta et al., 2010, Trends Biotech. 28:355-62).

As used herein, the term "single-chain Fv" or "sFv" antibody fragments comprise the VH and VL domains of an antibody, where these domains are present in a single polypeptide chain. Generally, the Fv polypeptide further comprises a polypeptide linker between the VH and VL domains which enables the sFv to form the desired structure for antigen binding. For a review of sFv, see Pluckthun in The Pharmacology of Monoclonal Antibodies, Vol. 113, pp. 269-315, Rosenburg and Moore, eds., Springer-Verlag, New York (1994).

As used herein, the term "diabodies" refers to small antibody fragments with two antigen-binding sites, which comprise a heavy chain variable domain (VH) connected to a light chain variable domain (VL) in the same polypeptide chain (VH-VL). By using a linker that is short to allow pairing between the two domains on the same chain, the domains are forced to pair with the complementary domains of another chain and create two antigen-binding sites.

As used herein, the term "antigen binding domain" or "antigen binding portion" refers to the region or part of the antigen binding molecule that specifically binds to and complementary to part or all of an antigen. In some embodiments, an antigen binding domain may only bind to a particular part of the antigen (e.g., an epitope), particularly where the antigen is large. An antigen binding domain may comprise one or more antibody variable regions, particularly an antibody light chain variable region (VL) and an antibody heavy chain variable region (VH), and particularly the complementarity determining regions (CDRs) on each of the VH and VL chains.

As used herein, the term "variable region" and "variable domain" are used interchangeably to refer to the polypeptide region that differ extensively in sequence between antibodies and confers the binding and specificity characteristics of each particular antibody. The variable region in the heavy chain of an antibody is referred to as "VH" while the variable region in the light chain of an antibody is referred to as "VL". The major variability in sequence is generally localized in three regions of the variable domain, denoted as "hypervariable regions" or "CDRs" in each of the VL region and VH region, and forms the antigen binding site. The more conserved portions of the variable domains are referred to as the framework region.

As used herein, the term "complementarity-determining region" or "CDR" are used interchangeably to refer to non-contiguous antigen binding regions found within the variable region of the heavy and light chain polypeptides. In some embodiments, the CDRs are also described as "hypervariable regions". Generally, naturally occurring antibodies comprise six CDRs, three in the VH (referred to as: CDR H1 or H1; CDR H2 or H2; and CDR H3 or H3) and three in the VL (referred to as: CDR L1 or L1; CDR L2 or L2; and CDR L3 or L3). The CDR domains have been delineated using various approaches, and it is to be understood that CDRs defined by the different approaches are to be encompassed herein. The "Kabat" approach for defining CDRs uses sequence variability and is the most commonly used (Kabat et al., 1991, "Sequences of Proteins of Immunological Interest, 5$^{th}$ Ed." NIH 1:688-96). "Chothia" uses the location of structural loops (Chothia and Lesk, 1987, J Mol Biol. 196:901-17). CDRs defined by "AbM" are a compromise between the Kabat and Chothia, and is delineated using Oxford Molecular AbM antibody modeling software (see, Martin et al., 1989, Proc. Natl Acad Sci USA. 86:9268; see also, world wide web www.bioinf-org.uk/abs). The "Contact" CDR delineations are based on analysis of known antibody-antigen crystal structures (see, e.g., MacCallum et al., 1996, J. Mol. Biol. 262, 732-45). The CDRs delineated by these methods typically include overlapping or subsets of amino acid residues when compared to each other. Generally, the residues defining the CDRs using each of the approaches are noted in the following:

| CDR | Kabat | Chothia | AbM | Contact |
| --- | --- | --- | --- | --- |
| CDR L1 | 24-34 | 24-34 | 24-34 | 30-36 |
| CDR L2 | 50-56 | 50-56 | 50-56 | 46-55 |
| CDR L3 | 89-97 | 89-97 | 89-97 | 89-96 |
| CDR H1 | 31-35B | 26-32B | 26-35 | 30-35B |
| | | (Kabat Numbering) | | |
| CDR H1 | 31-35 | 26-35 | 26-32 | 30-35 |
| | | (Chothia Numbering) | | |
| CDR H2 | 50-65 | 52-56 | 50-58 | 47-58 |
| CDR H3 | 95-102 | 95-102 | 95-102 | 93-101 |

It is to be understood that the exact residue numbers which encompass a particular CDR will vary depending on the sequence and size of the CDR, and those skilled in the art can routinely determine which residues comprise a particular CDR given the amino acid sequence of the variable region of an antibody.

Kabat, supra, also defined a numbering system for variable domain sequences that is applicable to any antibody. One of skill in the art can assign this system of "Kabat numbering" to any variable domain sequence. Accordingly, unless otherwise specified, references to the number of specific amino acid residues in an antibody or antigen binding fragment are according to the Kabat numbering system. In some embodiments, the sequences relevant to variable regions and CDRs (e.g., SEQ ID NOS: 23, 26, 31, 35, and 83-102) are not numbered according to Kabat numbering system, but one of ordinary skill in the art will recognize that such sequences can be converted to the Kabat numbering system.

As used herein, the term "framework region" or "FR region" refers to amino acid residues that are part of the variable region but are not part of the CDRs (e.g., using the Kabat, Chothia or AbM definition). The variable region of an antibody generally contains four FR regions: FR1, FR2, FR3 and FR4. Accordingly, the FR regions in a VL region appear in the following sequence: $FR_L1$-CDR L1-$FR_L2$-CDR L2-$FR_L3$-CDR L3-$FR_L4$, while the FR regions in a VH region appear in the following sequence: $FR1_H$-CDR H1-$FR_H2$-CDR H2-$FR_H3$-CDR H3-$FR_H4$.

As used herein, the term "human consensus framework" refers to a framework that represents the most commonly occurring amino acid residues in a selection of human immunoglobulin VL or VH framework sequences. Generally, the selection of human immunoglobulin VL or VH sequences is from a subgroup of variable domain sequences. In some embodiments, the subgroups sequences is a subgroup presented in Kabat et al., supra. In some embodiments, for the VL the subgroup is subgroup kappa described in Kabat et al., supra. In some embodiments, for the VH the subgroup is subgroup III described in Kabat et al., supra.

As used herein, the term "constant region" or "constant domain" refers to a region of an immunoglobulin light chain or heavy chain that is distinct from the variable region. The constant domain of the heavy chain generally comprises at least one of: a CH1 domain, a Hinge (e.g., upper, middle, and/or lower hinge region), a CH2 domain, and a CH3 domain. For example, an antibody described herein may comprise a polypeptide comprising a CH1 domain; a polypeptide comprising a CH1 domain, at least a portion of a Hinge domain, and a CH2 domain; a polypeptide comprising a CH1 domain and a CH3 domain; a polypeptide comprising a CH1 domain, at least a portion of a Hinge domain, and a CH3 domain, or a polypeptide comprising a CH1 domain, at least a portion of a Hinge domain, a CH2 domain, and a CH3 domain. In some embodiments, a polypeptide comprises a polypeptide chain comprising a CH3 domain. The constant domain of a light chain is referred to a CL, and in some embodiments, can be a kappa or lambda constant region. However, it will be understood by one of ordinary skill in the art that these constant domains (e.g., the heavy chain or light chain) may be modified such that they vary in amino acid sequence from the naturally occurring immunoglobulin molecule.

As used herein, the term "Fc region" or "Fc portion" refers to the C terminal region of an immunoglobulin heavy chain. The Fc region can be a native-sequence Fc region or a non-naturally occurring variant Fc region. Generally, the Fc region of an immunoglobulin comprises constant domains CH2 and CH3. Although the boundaries of the Fc region can vary, in some embodiments, the human IgG heavy chain Fc region can be defined to extend from an amino acid residue at position C226 or from P230 to the carboxy terminus thereof. In some embodiments, the "CH2 domain" of a human IgG Fc region, also denoted as "Cγ2", usually extends from about amino acid residue 231 to about amino acid residue 340. In some embodiments, N-linked carbohydrate chains are interposed between the two CH2 domains of an intact native IgG molecule. In some embodiments, the CH3 domain" of a human IgG Fc region comprises residues C-terminal to the CH2 domain, e.g., from about amino acid residue 341 to about amino acid residue 447 of the Fc region. A "functional Fc region" possesses an "effector function" of a native sequence Fc region. Exemplary Fc "effector functions" include, among others, C1q binding; complement dependent cytotoxicity (CDC); Fc receptor binding; antibody dependent cell-mediated cytotoxicity (ADCC); phagocytosis; down regulation of cell-surface receptors (e.g., LT receptor); etc. Such effector functions generally require the Fc region to be combined with a binding domain (e.g., an antibody variable domain) and can be assessed using various assays known in the art.

As used herein, the term "binding affinity" refers to strength of the sum total of noncovalent interactions between a ligand and its binding partner. In some embodiments, binding affinity is the intrinsic affinity reflecting a one-to-one interaction between the ligand and binding partner. The affinity is generally expressed in terms of equilibrium association ($K_A$) or dissociation constants ($K_D$), which are in turn reciprocal ratios of dissociation ($k_{off}$) and association rate constants ($k_{on}$).

As used herein, the term "percent (%) sequence identity" and "percentage sequence homology" are used interchangeably herein to refer to comparisons among polynucleotides or polypeptides, and are determined by comparing two optimally aligned sequences over a comparison window, wherein the portion of the polynucleotide or polypeptide sequence in the comparison window may comprise gaps as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, Adv Appl Math. 2:482, by the homology alignment algorithm of Needleman and Wunsch, 1970, J Mol Biol. 48:443, by the search for similarity method of Pearson and Lipman, 1988, Proc Natl Acad Sci USA. 85:2444-8, by computerized implementations of these algorithms (e.g., BLAST, ALIGN, GAP, BESTFIT, FASTA, and TFASTA; see, e.g., Mount, D. W., Bioinformatics: Sequence and Genome Analysis, $2^{nd}$ Ed., Cold Spring Harbor Laboratory Press, Cold Spring Harbor, N.Y. (2013))

Examples of algorithms that are suitable for determining percent sequence identity and sequence similarity are the BLAST and BLAST 2.0, FASTDB, or ALIGN algorithms, which are publically available (e.g., NCBI: National Center for Biotechnology Information). Those skilled in the art can determine appropriate parameters for aligning sequences. For example, the BLASTN program (for nucleotide sequences) can use as defaults a wordlength (W) of 11, an expectation (E) of 10, M=5, N=−4, and a comparison of both strands. Comparison of amino acid sequences using BLASTP can use as defaults a wordlength (W) of 3, an expectation (E) of 10, and the BLOSUM62 scoring matrix (see Henikoff and Henikoff, 1989, Proc Natl Acad Sci USA. 89:10915-9).

As used herein, the term "amino acid substitution" refers to the replacement of one amino acid in a polypeptide with another amino acid. A "conservative amino acid substitution" refers to the interchangeability of residues having similar side chains, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, isoleucine, and methionine; an amino acid with hydroxyl side chain is substituted with another amino acid with a hydroxyl side chain, e.g., serine and threonine; an amino acid having aromatic side chains is substituted with another amino acid having an aromatic side chain, e.g., phenylalanine, tyrosine, tryptophan, and histidine; an amino acid with a basic side chain is substituted with another amino acid with a basis side chain, e.g., lysine, arginine, and histidine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

As used herein, the term "amino acid insertion" refers to the incorporation of at least one amino acid into a predetermined amino acid sequence. An insertion can consist of the insertion of one or two amino acid residues; however, larger insertions of about three to about five, or up to about ten or more amino acid residues are contemplated herein.

As used herein, the term "amino acid deletion" refers to the removal of one or more amino acid residues from a predetermined amino acid sequence. A deletion can consist of the removal of one or two amino acid residues; however, larger deletions of about three to about five, or up to about ten or more amino acid residues are contemplated herein.

As used herein, the term "immunogen" refers to a moiety, which optionally can be administered to a subject, which induces an immunological response.

As used herein, the term "subsequence" refers to a sequence of a nucleic acid or polypeptide which comprises a part of a longer sequence of a nucleic acid or polypeptide, respectively.

As used herein, the term "adjuvant" refers to any substance that assists or modifies the immunological action of a composition, including but not limited to adjuvants that increase or diversify the immune response to an antigen.

As used herein, the term "fusion protein" and "fusion polypeptide" refer to a polypeptide comprising amino acid sequences derived from two or more heterologous polypeptides. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

As used herein, the term "candidate" in the context of screening refers to an antibody that is being considered or tested for desired properties, for example binding to defined epitopes.

As used herein, the term "identifying" refers to investigating for the presence or absence of a property. The process may include measuring or detecting various properties, including the binding or lack of binding to an epitope.

As used herein, the term "biological sample" refers to any biological material taken from a patient or subject. Such samples include tissue samples and fluid samples. A "fluid sample" includes, among others, a sample of a patient's blood, plasma, serum, urine, cerebrospinal fluid, lymph, synovial fluid, bile, semen, and saliva. A sample can also include a biopsy sample, whole cells, or lysates of cells.

As used herein, the term "subject" refers to a mammal, including, but not limited to humans, non-human primates, and non-primates, such as goats, horses, and cows. In some embodiments, the terms "subject" and "patient" are used interchangeably herein in reference to a human subject.

As used herein, the term "abnormal" or "abnormality" refers to a level or condition which is statistically different from the level or condition observed in organisms not suffering from such a disease or disorder and may be characterized as either an excess amount, intensity or duration of signal or a deficient amount, intensity or duration of signal. The abnormality may be realized as an abnormality in cell function, viability or differentiation state. An abnormal interaction level may also be greater or less than the normal level, and may impair the normal performance or function of the organism.

As used herein, the term "elevated" in the context of a disease or disorder refers to above normal levels of a substance or molecule, such as a disease marker or indicator, that has a statistically significant correlation with the occurrence of the disease or disorder. The levels can be compared to appropriate controls, e.g., healthy subjects without the disease, to determine the levels that signal presence of the disease.

As used herein, the terms "cancer" and "cancerous" refer to or describe the physiological condition in mammals in which a population of cells are characterized by unregulated cell growth. Examples of cancers include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

As used herein, the terms "proliferative disorder" and "proliferative disease" refer to disorders associated with abnormal cell proliferation such as cancer.

As used herein, the terms "tumor" and "neoplasm" refer to any mass of tissue that result from excessive cell growth or proliferation, either benign (noncancerous) or malignant (cancerous) including pre-cancerous lesions.

As used herein, the term "MICA$^+$ disease or disorder" refers to a disease or disorder displaying elevated levels of MICA protein or portions thereof, such as sMICA, that is correlated with the occurrence of the disease or disorder.

As used herein the term "MICB+ disease or disorder" refers to a disease or disorder displaying elevated levels of MICB protein or portions thereof, such as sMICB, that is correlated with the occurrence of the disease or disorder.

As used herein, the term "MIC+ epithelial tumor" refers to a tumor or neoplasm characterized by elevated levels of a MIC protein or portions thereof, such as sMICA, where the tumor or neoplasm originates from a tissue or cell that is of epithelial origin in accordance with clinical standards known in the art for identifying such disorders.

As used herein, the term "MIC+ hematologic malignancy" refers to proliferative disorders of cells of the lymphoid or myeloid system characterized by elevated levels of a MIC protein or portions thereof, such as sMICA and sMICB. Lymphoid disorders include acute lymphocytic leukemia and chronic lymphoproliferative disorders (e.g., lymphoma, myeloma, and chronic lymphoid leukemias). Lymphomas include Hodgkin's disease and non-Hodgkin's lymphoma, precursor T-cell leukemia/lymphoma, follicular lymphoma, diffuse large B-cell lymphoma, mantle cell lymphoma, MALT lymphoma, Burkitt's lymphoma, B-cell chronic lymphocytic leukemia/lymphoma, peripheral T-cell lymphoma—not-otherwise-specified, and mycosis fungoides. Chronic lymphoid leukemias include T cell chronic lymphoid leukemias and B cell chronic lymphoid leukemias. Myeloid disorders include chronic myeloid disorders and acute myeloid leukemia. Chronic myeloid disorders include chronic myeloproliferative disorders and myelodysplastic syndrome. Chronic myeloproliferative disorders include angiogenic myeloid metaplasia, essential thrombocythemia, chronic myelogenous leukemia, polycythemia vera, and atypical myeloproliferative disorders. Atypical myeloproliferative disorders include atypical CML, chronic neutrophilic leukemia, mast cell disease, and chronic eosinophilic leukemia.

As used herein, the term "MIC+ viral infection" refers to a viral infection characterized by elevated levels of a MIC protein or portions thereof, such as sMICA and sMICB.

As used herein, the term "treatment" or "treating" refers to a process that is intended to produce a beneficial change in the condition of a mammal, e.g., a human, often referred to as a patient. A beneficial change can, for example, include one or more of restoration of function; reduction of symptoms; reduction of severity; limitation or retardation of progression of a disease, disorder, or condition or prevention; or limitation or retardation of deterioration of a patient's condition, disease or disorder. In the context of a disease or disorder, a "therapy", "treatment", or "treatable" is meant the therapy achieves a desired pharmacologic and/or physiologic effect on the disease or disorder. The effect may be prophylactic in terms of completely or partially preventing the disease/disorder or symptom thereof and/or may be therapeutic in terms of a partial or complete cure for the disease/disorder and/or adverse effect attributable to the disease/disorder. The term includes: (a) preventing the disease from occurring in a subject which may be predisposed to the disease but has not yet been diagnosed as having it; (b) inhibiting the disease, i.e., arresting its development; or (c) relieving the disease, i.e., causing remission or regression of the disease. The therapeutic agent may be administered before, during or after the onset of the disease or disorder. The treatment of an ongoing disease, where the treatment stabilizes or reduces the undesirable clinical symptoms of the patient, is of particular interest. Such treatment is desirably performed prior to complete loss of function in the affected tissues.

As used herein, the term "therapeutically effective dose" or "therapeutically effective amount" refers to that quantity of a compound, including a biologic compound, or pharmaceutical composition that is sufficient to result in a desired activity upon administration to a mammal in need thereof. As used herein, with respect to the pharmaceutical compositions comprising an antibody, the term "therapeutically effective amount/dose" refers to the amount/dose of the antibody or pharmaceutical composition thereof that is sufficient to produce an effective response upon administration to a mammal.

As used herein, the term "pharmaceutically acceptable" refers to compounds or compositions which is generally safe, non-toxic and neither biologically nor otherwise undesirable, and includes a compound or composition that is acceptable for human pharmaceutical and veterinary use. The compound or composition may be approved or approvable by a regulatory agency or listed in the U.S. Pharmacopeia or other generally recognized pharmacopeia for use in animals, including humans.

As used herein, the term "pharmaceutically acceptable excipient, carrier or adjuvant" refers to an excipient, carrier or adjuvant that can be administered to a subject, together with at least one therapeutic agent (e.g., an antibody of the present disclosure), and which does not destroy the pharmacological activity thereof and is generally safe, nontoxic and neither biologically nor otherwise undesirable when administered in doses sufficient to deliver a therapeutic amount of the agent.

As used herein, the term "monotherapy" refers to a treatment regimen based on the delivery of one therapeutically effective compound, whether administered as a single dose or several doses over time.

As used herein, the term "combination therapy" refers to a therapeutic regimen that involves the provision of at least two distinct therapies to achieve an indicated therapeutic effect. For example, a combination therapy may involve the administration of two or more distinct active ingredients, for example, an antibody and a chemotherapeutic agent, or an antibody directed to a first target and a second antibody directed to a second target. Alternatively, a combination therapy may involve the administration of an antibody and/or one or more other therapeutic agents, alone or together with the delivery of another treatment, such as radiation therapy and/or surgery. In the context of the administration of two or more distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending physician or attending caregiver.

As used herein, the term "immune stimulating agent" or "immuno-activating agent" refers to an agent, such as a compound or composition, which enhances an immune response, e.g., as compared to the immune response in the absence of the immune stimulating agent.

As used herein, the term "vaccine" refers to a compound or composition which can be administered to humans or to animals in order to induce an immune system response; this immune system response can result in production of antibodies or result in the activation of certain cells, in particular antigen-presenting cells and immune system effector cells, such as T lymphocytes and B lymphocytes. The vaccine composition can be a composition for prophylactic purposes and/or for therapeutic purposes. As such, a "cancer vaccine" refers to a compound or composition which elicits an immune response against a cancer. The immune response can be against a broad spectrum of cancers or against a specific cancer.

As described above, in one aspect, the present disclosure provides binding agents, particularly antibodies, that bind specifically to soluble forms of MHC class I chain-related gene A protein (MICA) and/or MHC class I chain-related gene B protein (MICB). The MICA and MICB proteins are members of the MHC Class I-related chain (MIC) family and the related UL-16 binding proteins (Leelayuwat et al., 1994, Immunogenetics 40:339-51; Bahram, 1994, Proc Natl Acad Sci USA. 91:6259-63; Fodil et al., 1996, Immunogenetics 44:351-7; Groh et al., 1999, Proc Natl Acad Sci USA. 96:6879-84; Bauer et al., 1999, Science 285(5428):727-9), and act as ligands that bind to C-type lectin-like activating receptor Natural Killer Group 2D (NKG2D) on immune effector cells, including NK, NKT and both $\alpha\beta$ and $\gamma\delta$ CD8$^+$ T cells. Homology analyses indicate that MIC ligands are highly conserved in most mammals, with the exception of the rodent family, and are weakly related to MHC class I proteins. The highly related MICA and MICB glycoproteins are about 84% identical at the amino acid sequence level (Bahram et AL., 1994, Proc Natl Acad Sci USA. 91:6259-6263; Bahram, 1996, Immunogenetics 44:80-81; Bahram and Spies., 1996, Immunogenetics 43:230-233). The MICA and MICB proteins are stress-induced and are similar to MHC class I molecules; however, they do not associate with beta-2-microglobulin or bind peptides.

MIC proteins are expressed normally at low levels in the gut epithelium, on keratinocytes, monocytes and endothelial cells, but are induced to higher levels in stressed, transformed or some virally-infected cells (Groh et al., 1999, Proc Natl Acad Sci USA. 96:6879-84; Bauer et al., 1999, Science 285(5428):727-9; Zwirner et al, 1998, Immunogenetics 47:139-41). The interaction of NKG2D-bearing immune effector cells with stressed or diseased cells expressing MIC ligands on the cell surface creates a cellular immune response against the stressed/diseased cell that culminates in the death of the MIC expressing cells. Binding of the MIC ligands to NKG2D receptor bearing immune cells stimulates the activation of naive T cells and can even induce cytotoxicity in the absence of appropriate TCR ligation. In humans, the NKG2D receptor functions as a co-stimulatory molecule along with DAP10 to impart the ligand binding signal to the interior of the cell via the phosphatidylinositol kinase (PI3K) pathway.

The expression of NKG2D ligands has been reported in many types of tumors and is thought to be the result of gene expression arising from stimulation of heat shock promoter elements as well as the intracellular detection of DNA damage resulting from either environmental insult or the increasing level of genomic instability associated with cancer. In cancer patients, the extracellular domain comprising alpha-1, -2 and -3 domains is frequently shed into the blood by the action of proteases and results in the down-modulation (receptor internalization) of its intended receptor, NKG2D, on effector immune cells (see, e.g., Groh et al., 2002, Nature 419:734-8). In some individuals, MICA glycoproteins are produced intracellularly that are not routinely destined to become cell surface membrane-bound, but instead are incorporated within exosomes and released outside the cell where interaction with NKG2D receptors on immune cells occurs (Ashiru et al., 2010, Cancer Res. 70:481-9). Studies suggest that these tumor-derived soluble MICA and MICB ligands (sMICA and sMICB) shed from the surface of tumor cells function like decoy molecules and lead to down-modulation of the NKG2D receptor on immune effector cells such as NK, NKT and various CD8$^+$ T cells. The formation of sMICA and sMICB require the participation of protein disulfide isomerase ERp5, which appear to form transitory mixed disulphide complexes to enable proteolytic cleavage of the membrane bound MICA and MICB (Kaiser et al., 2007, Nature 447(7143):482-6). The formation of sMICA and sMICB leads to the unusual situation where the effectors of the innate defense system, whose natural role is to seek and destroy transformed cells, are shut down by the immunosuppressive actions of these decoy MIC ligand molecules. Through this mechanism, tumor cells are capable of hiding from the immune system and can continue to grow unabated. As a further consideration, persistent NKG2D ligand expression and shedding promote proliferation of normally rare, immunosuppressive NKG2D$^+$ CD4$^+$ T cells in cancer patients, and is directly correlated with serum concentration of sMICA, thereby enabling NKG2D costimulation of T cell proliferation (see, e.g., Groh et al., 2006, Nat Immunol. 7:755-62).

The adverse effects of sMICA and sMICB are supported by presence of significantly elevated levels of soluble MIC immune decoy molecules (sMICA and/or sMICB) in the blood of advanced cancer patients as compared to healthy individuals (Groh et al., 2002, Nature 419:734-8; Salih et al., 2002, J Immunol 169:4098-102). These high levels appear to correlate directly with both the clinical staging of the cancer and to poor clinical outcomes (Doubrovina et al., 2003, J Immunol. 171:6891-9; Wu et al., 2004, J Clin Invest. 114:560-8; Holdenreider et al., 2006, Intl J Cancer 118:684-7). In vitro experiments have also shown that addition of recombinant or tumor cell-derived sMIC proteins can decrease the level of NKG2D receptors on effector immune cells such as NK and T cells and that this effect can be blocked by neutralizing antibodies to the soluble ligands through interference with receptor binding (Groh et al., 2002, Nature 419:734-8). Thus, reduced NKG2D expression on both systemic and tumor-infiltrated effectors cells can limit the immune responses against tumors in sMIC patients. However, it is highly unlikely that the aforementioned specific neutralizing rodent antibodies could be useful as human therapeutics (even if humanized) as they would also bind cell-bound MIC ligands and could therefore create unwanted immune responses against certain cells expressing endogenous MIC ligands under normal conditions.

The involvement of sMICA and sMICB in viral infection comes from observations indicating that Respiratory Syncytial Virus (RSV) infections in respiratory epithelial cells led to the upregulation of cell surface expression of MICA and circulating levels of sMICA (Zdrenghea et al., 2012, Eur Respir J. 39:712-20). In this instance, higher levels of sMICA may impair clearance of the virus and potentially aid in prolonging the infection. Again, NK cells are known to play key cytotoxicity roles in the response of the immune system to RSV infections just as they function in detection of transformed cells in the proposed immunosurveillance system. Suppression of NK cell function via sMIC-induced down-modulation of NKG2D receptors on effector immune cells could either represent a viral response for avoiding immune detection or a cellular safety mechanism for reducing cytolysis of uninfected bystander cells once antiviral gamma interferon is released during the infection of the cell. Considering the delicate balance between development of an adequate immune response to the virus and the consequential loss of NK cell function known to occur in RSV infections, it can be surmised that excessive sMICA will not be helpful in the desired overall antiviral response. Efforts to reduce the levels of sMICA during these RSV infections are therefore warranted especially in the very young and in the elderly patient where prolonged viral infections frequently result in serious damage to the lining of the respiratory tract and even death as a result of difficult-to-treat secondary bacterial infections. Release of soluble NKG2D ligands has also been described in viral infections of humans with Human Immunodeficiency Virus type 1 (HIV-1) (Nolting et al., 2010, Virology 406:12-20) or with Hepatitis B Virus (HBV) that result in the onset of hepatocellular carcinoma (HCC). Matusali et al., 2013, FASEB J. 27(6):2440-50 reported that NKG2D ligand shedding by HIV-1 infected lymphocytes induces NKG2D down-regulation in NK and $CD8^+$ T cells and led to dampening of the immune response against the virally-infected cells. Levels of sMICA, sMICB and sULBP2 were all elevated in the medium of in vitro HIV-1 infected $CD4^+$ T cells. Moreover, chronically-infected patients with HIV-1 possessed 7-fold higher levels of sMICA compared with aviremic Highly Active Anti-Retroviral Therapy (HAART)-treated patients, and a similar trend was noted for sULBP2 but not with sMICB. Reducing the levels of soluble NKG2D ligands in HIV-1 infections by the binding agents and methods outlined in this disclosure may serve to improve the cytotoxic functionality of NK cells by increasing NKG2D cell-surface levels and thereby imparting an overall improvement in immunosurveillance and NK control of HIV-1 infections. Also, Kumar et al., 2012, PLOS One 7:1-6 E44743 found a significant elevation of sMICA in HBV-induced HCC cases. In fact, $HBV^+$ HCC patients who had elevated levels of sMICA had significantly worse survivability than those with normal levels, presumably because higher sMICA levels would cause inactivation of the immune surveillance system against HBV-infected cells. Again, reduction in circulating sMIC ligands would be consistent with improved immune reactivity towards chronic viral infections.

Given their role in immunosurveillance, MICA and MICB and cognate receptor NKG2D have been targets for development of therapeutics for treating various diseases associated with MICA and MICB, such as cancers and autoimmune diseases. For example, patent publication WO 98/019167 describes cell stress regulated human MIC Class 1 gene and treatment of certain disease states including GVHD and cancers. Patent publications WO 03/089616, US20050233391, US20100316650; and U.S. Pat. No. 7,771,718 describe soluble MIC polypeptides as markers for diagnosis, prognosis, and treatment of cancer and autoimmune diseases or conditions. Patent publications U.S. Pat. No. 7,666,417 and WO 2006/024367 describe NKG2D receptor/NKG2D ligand interaction blockers for treating autoimmune diseases. Patent publications WO 2008/036981 and U.S. Pat. No. 7,959,916 describe methods of treating MICA-related disorders through use of anti-MICA antibodies and modulation of ERp5 (protein disulfide isomerase) activity, such as by ERp5 antibodies or by modulating ERp5 expression. U.S. Pat. No. 8,182,809 also describes methods for treating cancer by inhibiting MIC shedding (e.g., formation of soluble MICA) by use of an anti-MICA antibody.

The present disclosure provides binding agents, particularly antibodies, directed to epitopes on the extracellular (i.e., ectodomain) of MICA and/or MICB, where the epitopes become available for binding when the extracellular domain is separated from the intact MIC protein. Thus, the antibodies should discriminate shed sMICA and/or sMICB proteins from intact or cell-bound MICA and/or MICB proteins. Because the binding agents will be specific for the soluble forms of the MIC proteins, it can be used as a therapeutic approach to neutralizing and/or instigating clearance of sMICA and/or sMICB, thereby mitigating the detrimental effects of, e.g., immunosuppressive properties, of sMICA and/or sMICB released from cells in certain types of diseases, including among others, cancers and viral infections.

Accordingly, in some embodiments, the binding agents herein are directed to antibodies that bind specifically to an extracellular domain of MICA but do not bind specifically to full length MICA or the extracellular domain of membrane bound form of MICA. In some embodiments, the binding agents herein are directed to antibodies that bind specifically to an extracellular domain of MICB but do not bind specifically to full length MICB or extracellular domain of membrane-bound form of MICB. An exemplary full length MICA protein is presented in FIG. 1A (SEQ ID NO:1), with the extracellular domain of MICA being represented by amino acid residues from about 24 to about 297, and up to residue 307, of the sequence in FIG. 1A. An exemplary full length MICB protein is presented in FIG. 1B (SEQ ID NO:2), with the extracellular domain of MICB being represented by amino acid residues from about 24 to about 297, and up to residue 307 of the sequence in FIG. 1B. In some embodiments, the antibodies herein comprise isolated antibodies.

In some embodiments, the antibody binds specifically to a soluble form of MICA (sMICA), where the antibody does not bind specifically to the naturally occurring full length MICA or extracellular domain of a membrane-bound form of MICA.

In some embodiments, the antibody binds specifically to a soluble form of MICB (sMICB), where the antibody does not bind specifically to naturally occurring full length MICB or extracellular domain of membrane-bound form of MICB.

The soluble forms of MICA and/or MICB are truncated proteins that lack the transmembrane domain and cytoplasmic tail but retain the three extra-cellular domains: alpha-1, alpha-2 and alpha-3 domains. The soluble forms of the MIC protein, which can be found in various types of tumors, can have variable carboxy terminal ends owing to the process by which the soluble forms are generated. Without being bound by theory, the naturally occurring soluble forms appear to result from the actions of a disulfide isomerase, endoplasmic reticulum protein 5, also referred to as ERp5, PDIA6 or P5, which forms a complex with the MICA or MICB protein and reduces the disulfide bond in the alpha-3 domain. The soluble MIC protein is released after proteolytic cleavage near the cell membrane. These truncations appear not to occur at specific proteolytic recognition sites (see, e.g., Wang et al., 2009, Biochem Biophys Res Comm. 387:476-81) but instead occur in a random fashion within the alpha-3 domain sequence upstream of the transmembrane section and downstream of the reported conserved ERp5 binding site at N238-T243 of MICA or homologous sequence in MICB.

The present disclosure has identified a number of epitopes on the alpha-3 domain, and specifically at the section of the alpha-3 domain that is in close proximity to the cellular membrane, that are exposed by the proteolytic processing of the MIC protein and to which antibodies can bind to distinguish between soluble forms of MIC protein (or the extracellular domain of the MIC proteins) from the intact or membrane bound forms of MICA and/or MICB. Accordingly, in some embodiments, the antibody binds specifically to the alpha-3 domain of MICA but does not bind specifically to the naturally occurring full length MICA or extracellular domain of a membrane-bound form of MICA. In some embodiments, the antibody binds specifically to a cryptic epitope on the alpha-3 domain of MICA, but does not bind specifically to the naturally occurring full length MICA or extracellular domain of a membrane-bound form of MICA. In some embodiments, the antibody binds specifically to the alpha-3 domain of MICB, but does not bind specifically to the naturally occurring full length MICB or extracellular domain of a membrane-bound form of MICB. In some embodiments, the antibody binds specifically to a cryptic epitope on the alpha-3 domain of MICB, but does not bind specifically to the naturally occurring full length MICA or extracellular domain of a membrane-bound form of MICB.

In some embodiments, the antibody of the present disclosure has insignificant autoimmune disease inducing activity when administered to a subject. Without being bound by theory, antibodies that bind the alpha-1 or alpha-2 domain or against sections of the alpha-3 domain that may be "recognized" normally by the immune system when the MICA (or MICB) protein is attached to a cell could create a situation where constitutively-expressed MICA, for example in the gut epithelium, could be bound by the inappropriately targeted therapeutic antibodies and hence lead to an unwanted immune response at that site, particularly an autoimmune reaction.

In some embodiments, the antibody of the present disclosure has insignificant antagonistic activity against binding of MIC protein to its cognate receptor NKG2D. The antibodies herein that bind specifically to the cryptic epitopes on the alpha-3 domain are unlikely to bind MICA and/or MICB present on the cell surface. Hence, the antibodies should have insignificant effect on interaction of the MICA and/or MICB protein with the NKG2D receptor. Additionally, the alpha-3 domain is located at a region proximal to the transmembrane domain, away from the regions that would typically interact with the receptor.

In some embodiments, enhancing immune response as contemplated herein also includes one or more of the following: upregulation of T cell, natural killer (NK) cell, natural killer T (NKT) cell, γδ T cell, αβ T cell, and B cell function. In some embodiments, upregulation of one or more of T cell, natural killer (NK) cell, natural killer T (NKT) cell, γδ T cell, αβ T cell, and B cell function includes enhancement and/or endowment of activity capable of inhibiting cancer progression or inhibiting viral infection.

In some embodiments, the antibody of the present disclosure binds specifically to undenatured or naturally occurring forms of sMICA and/or sMICB. Therapeutically useful antibodies will bind specifically to the naturally occurring target molecule, in this instance sMICA and sMICB. Such antibodies can be obtained by using polypeptide antigens that contain the cryptic epitopes but also retain the 3-dimensional structure in which the epitope resides. As further discussed below, using polypeptide immunogens that contain the alpha-3 domain or various substructures (e.g., loops) of the alpha-3 domain and then screening candidate antibodies using the defined cryptic epitopes will allow identification of antibodies with specific binding to undenatured or naturally occurring forms of sMICA and/or sMICB.

In some embodiments, the cryptic epitopes to which the antibody binds are within the alpha-3 domain of MICA defined by an amino acid sequence from amino acid residues 187 to 296, or 187 to 297, particularly amino acid residues 187 to 274, more particularly amino acid residues 190 to 256 of MICA protein, where the amino acid numbering is based on the processed MICA protein of the MICA*001 allele. An exemplary sequence for the alpha-3 domain on the extracellular region of MICA is presented in FIG. 1C (SEQ ID NO:3). In some embodiments, the cryptic epitopes to which the antibody binds are within the alpha-3 domain of MICB defined by an amino acid sequence from amino acid residues 187 to 296, or 187 to 297, particularly amino acid residues 187 to 274, more particularly amino acid residues 190 to 256 of MICB protein, where the amino acid numbering is based on the processed MICB protein of the MICB*001 allele. An exemplary sequence for the alpha-3 domain on the extracellular region of MICB is presented in FIG. 1D (SEQ ID NO:4). It is to be understood, as further described below, that the equivalent regions and corresponding amino acid sequences containing the cryptic epitopes in various polymorphic forms of MICA and MICB can be identified in view of the exemplary MICA and MICB proteins and sequences described in the present disclosure, for example by comparing the amino acid sequences. Sequence alignments can be conveniently determined using known computer programs, as described herein, for example, BLAST, FASTDB, ClustalW, and LALIGN (see, e.g., Altschul et al., 1990, J Mol Biol. 215(3):403-10; Brutlag et al., 1990, Comp App Biosci. 6:237-45; Smith and Waterman, 1981, Adv Appl Math. 2:482-9). An exemplary amino acid sequence alignment can be carried out using FASTDB using the following parameters: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. Alternatively, the sequence alignment can be carried out using BLAST, using default parameters.

In some embodiments, the cryptic epitopes to which the antibody binds are within a subsequence of the alpha-3 domain, wherein the subsequence is selected from:
  amino acid residues 190 to 229;
  amino acid residues 190 to 238;
  amino acid residues 217 to 238;
  amino acid residues 243 to 256
  amino acid residues 243 to 274; and
  amino acid residues 243 to 296/297
of MICA or MICB, where the amino acid numbering is as described above.

In some embodiments, the cryptic epitope within the alpha-3 domain comprises a sequence region selected from:
  amino acid residues 190 to 196;
  amino acid residues 217 to 221;
  amino acid residues 234 to 238
  amino acid residues 250 to 256; and
  amino acid residues 251 to 256
of MICA, including the corresponding region in any of the alleles of MICA existing in the human population, such as the identified MICA alleles available in Robinson et al., 2003, "IMGT/HLA and IMGT/MHC: Sequence databases for the study of the major histocompatibility complex", Nucleic Acids Res. 31:311-314 and the Anthony Nolan Research Institute world wide web site www.anthonynolan.org.uk/HIG/data.html; which are incorporated herein by reference. Thus, it is to be understood that for each and every embodiment of MICA cryptic epitopes described herein, the equivalent epitopes are also described for each and every one of the MICA allelic variants, including human MICA allelic variants selected from MICA*001, MICA*002:01, MICA*002:02, MICA*002:03, MICA*002:04, MICA*004, MICA*005, MICA*006, MICA*007:01, MICA*007:02, MICA*007:03, MICA*007:04, MICA*007:05, MICA*007:

06, MICA*008:01:01, MICA*008:01:02, MICA*008:02, MICA*008:03, MICA*008:04, MICA*008:05, MICA*009:01, MICA*009:02, MICA*010:01, MICA*010:02, MICA*011, MICA*012:01, MICA*012:02, MICA*012:03, MICA*012:04, MICA*013, MICA*014, MICA*015, MICA*016, MICA*017, MICA*018:01, MICA*018:02, MICA*019, MICA*020, MICA*022, MICA*023, MICA*024, MICA*025, MICA*026, MICA*027, MICA*028, MICA*029, MICA*030, MICA*031, MICA*032, MICA*033, MICA*034, MICA*035, MICA*036, MICA*037, MICA*038, MICA*039, MICA*040, MICA*041, MICA*042, MICA*043, MICA*044, MICA*045, MICA*046, MICA*047, MICA*048, MICA*049, MICA*050, MICA*051, MICA*052, MICA*053, MICA*054, MICA*055, MICA*056, MICA*057, MICA*058, MICA*059, MICA*060, MICA*061, MICA*062, MICA*064N, MICA*065, MICA*066, MICA*067, MICA*068, MICA*069, MICA*070, MICA*072, MICA*073, MICA*074, MICA*075, MICA*076, and MICA*077.

In some embodiments, the cryptic epitope within the alpha-3 domain to which the antibody binds comprises a sequence region selected from:
    amino acid residues 190 to 196;
    amino acid residues 217 to 221;
    amino acid residues 234 to 238; and
    amino acid residues 250 to 256
of MICB, including the region in any of the alleles of MICB existing in the human population, such as the identified MICB alleles available in Robinson et al., 2003, "IMGT/HLA and IMGT/MHC: Sequence databases for the study of the major histocompatibility complex", Nucleic Acids Res. 31:311-314 and the Anthony Nolan Research Institute world wide web site www.anthonynolan.org.uk/HIG/data.html; which are incorporated herein by reference. Thus, it is to be understood that for each and every embodiment of MICB cryptic epitopes described herein, the equivalent epitopes are also described for each and every one of the MICB allelic variants, including human MICB allelic variants selected from MICB*001, MICB*002:01:01, MICB*002:01:02, MICB*003, MICB*004:01:01, MICB*004:01:02, MICB*005:01, MICB*005:02:01, MICB*005:02:02, MICB*005:02:03, MICB*005:02:04, MICB*005:03, MICB*005:04, MICB*005:05, MICB*005:06, MICB*005:07, MICB*005:08, MICB*006, MICB*007, MICB*008, MICB*009N, MICB*010, MICB*011, MICB*012, MICB*013, MICB*014, MICB*015, MICB*016, MICB*018, MICB*019, MICB*020, MICB*021N, MICB*022; MICB*023, MICB*024, MICB*025, MICB*026, MICB*027, MICB*028, and MICB*029.

In some embodiments, the antibody binds specifically to an epitope of MICA defined by the sequence:
    190_RSEASEG_196, located on bottom of alpha-3 domain (SEQ ID NO:38);
    217_RQDGV_221, located on lower side of alpha-3 domain (SEQ ID NO:39);
    234_LPDGN_238, located near the top of alpha-3 domain (SEQ ID NO:40);
    251_QGEEQR_256, located on bottom of alpha-3 domain (SEQ ID NO:41); or
    251_RGEEQR_256, located on bottom of alpha-3 domain (SEQ ID NO:42),
where the amino acid positions are defined with respect to the mature, processed MICA protein of the MICA*001 allele.

All of the specific antigenic sites above for MICA are highly conserved within most of the different alleles known for MICA, and hence, the antibodies may specifically recognize a significant majority if not all of the polymorphic MICA proteins occurring in human populations.

In some embodiments, the antibody binds an epitope comprising one or more amino acid residues selected from R190, S191, E192, A193, S194, E195, and G196, located at the bottom of the alpha-3 domain, where the amino acid positions are defined with respect to the mature, processed MICA protein of the MICA*001 allele. In some embodiments, the epitope comprises 1, 2, 3 or more, or 1, 2, 3, 4 or more of the foregoing amino acid residues in the alpha-3 domain.

In some embodiments, the antibody binds an epitope comprising one or more amino acid residues selected from R217, Q218, D219, G220, and V221, located on the lower side of the alpha-3 domain, where the amino acid positions are defined with respect to the mature, processed MICA protein of the MICA*001 allele. In some embodiments, the epitope comprises 1, 2, 3 or more, or 1, 2, 3, 4 or more of the foregoing amino acid residues in the alpha-3 domain.

In some embodiments, the antibody binds an epitope comprising one or more amino acid residues selected from Q251/R251, G252, E253, E254, Q255, and R256, located on the bottom of the alpha-3 domain, where the amino acid positions are defined with respect to the mature, processed MICA protein of the MICA*001 allele. In some embodiments, the epitope comprises 1, 2, 3 or more, or 1, 2, 3, 4 or more of the foregoing amino acid residues in the alpha-3 domain.

In some embodiments, the antibody binds an epitope comprising one or more amino acid residues selected from L234, P235, D236, G237, and N238, located near the top of the alpha-3 domain, where the amino acid positions are defined with respect to the mature, processed MICA protein of the MICA*001 allele. In some embodiments, the epitope comprises 1, 2, 3 or more, or 1, 2, 3, 4 or more of the foregoing amino acid residues in the alpha-3 domain.

One exception to the high degree of conservation noted above concerns the predicted epitope surrounding MICA amino acid position 251, where the residue is glutamine (Q) in the MICA*001 allele and where there is a substantial presence of the amino acid arginine (R) at other MICA alleles. Accordingly, in some embodiments, the antibody binds specifically to an epitope defined by:
    251_RGEEQR_256, located on the bottom of the alpha-3 domain (SEQ ID NO:42), where the amino acid residue numbering is in reference to the mature, processed MICA protein of the MICA*001 allele. This epitope is found in, but not limited to, MICA alleles *005; *008:01:01; *008:01:02; *008:02; *008:03; *008:04; *008:05; *010:01; *010:02; *013; *016; *019; *022; *027; *033; *035; *037; *039; *042; *048; *053; *054; *056; *058; *062; *065; *069; *070; *073 and *076 (see, e.g., Robinson et al., supra; and Anthony Nolan Research Institute Web site at www.anthonynolan.org.uk/HIG/data.html).

In some embodiments, the antibody binds specifically to an epitope of MICB defined by the sequence:
    190_CSEVSEG_196, located on bottom of alpha-3 domain (SEQ ID NO:43);
    217_RQDGV_221, located on lower side of alpha-3 domain (SEQ ID NO:44);
    234_LPDGN_238, located near the top of alpha-3 domain (SEQ ID NO:45); or
    250_RQGEEQR_256, located on bottom of alpha-3 domain (SEQ ID NO:46), where the amino acid positions are defined with respect to the mature, processed MICB protein of the MICB*001 allele.

Similar to MICA, the antigenic sites above for MICB are highly conserved across most of the different alleles known for the alpha-3 domain of MICB such that the antibodies may specifically recognize a significant majority if not all of the polymorphic MICB proteins occurring in human populations.

In some embodiments, the antibody binds an epitope comprising one or more amino acid residues selected from C190, S191, E192, V193, S194, E195, and G196, located on the bottom of the alpha-3 domain, where the amino acid positions are defined with respect to the mature, processed MICB protein of the MICB*001 allele. In some embodiments, the epitope comprises 1, 2, 3 or more, or 1, 2, 3, 4 or more of the foregoing amino acid residues in the alpha-3 domain.

In some embodiments, the antibody binds an epitope comprising one or more amino acid residues selected from R217, Q218, D219, G220, and V221, located on the lower side of the alpha-3 domain, where the amino acid positions are defined with respect to the mature, processed MICB protein of the MICB*001 allele. In some embodiments, the epitope comprises 1, 2, 3 or more, or 1, 2, 3, 4 or more of the foregoing amino acid residues in the alpha-3 domain.

In some embodiments, the antibody binds an epitope comprising one or more amino acid residues selected from R250, Q251, G252, E253, E254, Q255, and R256, located on the bottom of the alpha-3 domain, where the amino acid positions are defined with respect to the mature, processed MICB protein of the MICB*001 allele. In some embodiments, the epitope comprises 1, 2, 3 or more, or 1, 2, 3, 4 or more of the foregoing amino acid residues in the alpha-3 domain.

In some embodiments, the antibody binds an epitope comprising one or more amino acid residues selected from L234, P235, D236, G237, and N238, located near the top of the alpha-3 domain, where the amino acid positions are defined with respect to the mature, processed MICB protein of the MICB*001 allele. In some embodiments, the epitope comprises 1, 2, 3 or more, or 1, 2, 3, 4 or more of the foregoing amino acid residues in the alpha-3 domain.

In some embodiments, the epitope of the alpha-3 domain to which the antibody binds is within the amino acid sequence defined by:

(a) (SEQ ID NO: 47)
~$X^{41}$-S-$X^{43}$-$X^{44}$-S-E-G~, where $X^{41}$ is selected from R and C; $X^{43}$ is selected from E and K; and $X^{44}$ is selected from A and V;

(b) (SEQ ID NO: 48)
~R-Q-D-G-$X^{B5}$~, where $X^{B5}$ is selected from V and L;

(c) (SEQ ID NO: 49)
~$X^{D1}$-$X^{D2}$-G-E-E-Q-$X^{D7}$~, where $X^{D1}$ is selected from C or R; $X^{D2}$ is selected from Q, R, and E; and $X^{D7}$ is selected from R, S, and K; or (d) (SEQ ID NO: 50)
~L-P-D-G-N~.

Accordingly, in some embodiments, the antibody binds specifically to an epitope of the alpha-3 domain within an amino acid sequence defined above. In some embodiments, the antibody binds specifically to an epitope within the amino acid sequence:

(a) (SEQ ID NO: 47)
~$X^{41}$-S-$X^{43}$-$X^{44}$-S-E-G~, where $X^{41}$ is selected from R and C; $X^{43}$ is selected from E and K; and $X^{44}$ is selected from A and V.

In some embodiments, the antibody binds specifically to an epitope within the amino acid sequence:

(b) (SEQ ID NO: 48)
~R-Q-D-G-$X^{B5}$~, where $X^{B5}$ is selected from V and L.

In some embodiments, the antibody binds specifically to an epitope within the amino acid sequence:

(c) (SEQ ID NO: 49)
~$X^{D1}$-$X^{D2}$-G-E-E-Q-$X^{D7}$~, where $X^{D1}$ is selected from C or R; $X^{D2}$ is selected from Q, R and E; and $X^{D7}$ is selected from R, S and K.

In some embodiments, the antibody binds specifically to an epitope within the amino acid sequence:

(d) (SEQ ID NO: 50)
~L-P-D-G-N~.

In some embodiments, any of the epitopes may contain an additional 1, 2, 3, 4, or 5 amino acids at the amino terminal and/or carboxy terminal end, where the additional amino acids can be those found on the naturally occurring MICA or MICB amino acid sequence surrounding the described defined region or the defined amino acid sequence.

In some embodiments, additional cryptic epitopes can be identified by examining the alpha-3 domain in the X-ray crystal structure of the extracellular domains of MICA or MICB (see, e.g., Li et al., 1999, Immunity 10:577-84; Li et al., 2001, Nature Immunol. 2(5):443-51; Holmes et al., 2002, J Immunol 169: 1395-400; and Protein Data Bank (PDB) X-ray crystal structures 1HYR for MICA and 1JE6 for MICB). Several looping structures consistent with predicted antigenic sites that are hidden from the immune system are likely exposed in the freed/shed MIC protein (sMICA and sMICB), including the epitopes described above, and thus useful for generating antibodies that bind the cryptic epitopes. These amino acid sequence motifs can be determined from secondary structural predictions (e.g., Chou and Fasman, 1978, Ann Rev Biochem. 47:251-76) as well as from close inspection of the 3-dimensional X-ray crystal structure(s), and more specifically by assessing the combination of primary sequence, surface accessibility, and β-turn characteristic that are consistent with potential B-cell epitopes. In addition, various prediction methods that can be used to identify these cryptic epitopes from 3D structures (e.g., crystal structures) include, among others, those described in Haste et al., 2006, Protein Sci. 15:2558-67; Kringelum et al., 2012, PLOS Computational Biol. 8(12): e1002829; Kuroda et al., 2012, Protein Eng Des Sel. 25(10): 507-521; and Soga et al., 2010, Protein Eng Des Sel. 23(6):441-8; all publications incorporated herein by reference.

While an analysis of amino acid residues 224 to 229 (amino acid numbering based on MICA protein of the MICA*001 allele) suggests that this region might serve as a cryptic site, studies described in International Patent Publication WO2013117647 indicate that this sequence may not comprise a cryptic epitope. The primary screening of antibodies in WO2013117647 used cell lines expressing MICA protein encoded by various alleles of MICA, and thus identified antibodies that bind to the extracellular domain of mature full length MICA protein. Accordingly, specifically excluded from scope of a cryptic epitope is the alpha-3 domain region defined by amino acid residues 224 to 232, as well as any other specific region defined in WO2013117647, incorporated herein by reference. Specific antibodies excluded from the scope of the present disclosure include monoclonal antibodies designated as 9C10, 12A10, 19E9, 18 E8, 10F3, 15F9, 6E4, 20C6, 10A7, 16A8, and 14B4, particularly antibodies 15F9, 16A8 and 14B4, as well as antibodies with the corresponding CDR sequences as described in WO2013117647. The primary epitope of 15F9 includes residues R6, N8, E97, H99, E100, D101, N102, S103, T104, R105, E115, L178, R179 and R180. The primary epitope of 16A8 includes residues W230, D232, T227, Q228, Q229, S224, H225 and D226 of MICA. The primary epitope of 14B4 includes T227, Q228, Q229, and thus overlaps with 16A8.

In some embodiments, also specifically excluded from the scope of the present disclosure are antibodies that bind the epitope defined by sequence 238_NGTYQT_243 (SEQ ID NO:51) in the reference MICA*001 allele, and the same or similar amino acid sequence in the reference MICB*001 allele. This sequence defines a region in the MIC proteins that interacts with the disulfide isomerase ERp5 and is believed required for proteolytic processing of membrane bound MIC to produce soluble MIC proteins. Antibodies that bind specifically to the NGTYQT (SEQ ID NO:51) epitope inhibits the interaction of MIC protein and ERp5, thereby inhibiting the production of soluble MIC proteins (see, e.g., U.S. Pat. No. 8,182,809). In order for the antibody to bind, the epitope must be exposed to the solution environment in the membrane bound MIC protein, and thus not considered a cryptic epitope as described herein.

In some embodiments, also excluded from the scope of the present disclosure are monoclonal antibodies designated 2C10, 6D4, 6G6, and 3H5, as well as antibodies with the corresponding CDR sequences, as disclosed in U.S. Pat. No. 7,771,718 and WO03089616. Monoclonal antibodies 2C10, 6D4, 6G6 and 3H5 were generated using cells expressing full length MICA protein as an immunogen.

Further excluded from the scope of the present disclosure include monoclonal antibodies designated as SR99, SR104 and SR116, as well as antibodies with the corresponding CDR sequences, as described in Hue et al, 2003, J Immunol 171:1909-1917 and Hue S, et al., 2004, Immunity 21:367-377. The SR99, SR104 and SR116 antibodies were selected for binding to MICA protein expressed on surface of cells, and therefore a selection that should not identify antibodies that bind cryptic epitopes, including the cryptic epitopes specifically described herein.

In the embodiments herein, the isolated antibody with the relevant properties can be polyclonal, monoclonal, non-human, chimeric, humanized, or fully human antibody. The antibody can be monospecific (i.e., binds to single epitope—monovalent) or multi-specific (i.e., binds to more than a single epitope—multivalent), including bispecific and trispecific antibodies (see, e.g., Sharkey et al., 2010, Cancer Biother Radiopharm. 25(1):1-12); U.S. patent publication 20080069820; incorporated herein by reference). In some embodiments, the antibody can be a single chain antibody or diabodies, which are small bivalent and bispecific antibody fragments. In some embodiments, the antibody can comprise a non-human antibody, such as prepared from goat, horse, cow, chicken, camel, llamas, rabbit, rat, or mouse, or a chimeric or humanized antibody based on the non-human antibody.

In some embodiments, the antibody of the disclosure is characterized by an affinity ($K_A$=equilibrium association constant or the ratio of association rate constant $k_{on}$/dissociation rate constant $k_{off}$) for the sMICA and/or sMICB protein, or the alpha-3 domain thereof, in the range of about $10^4$ to about $10^{12}$ $M^{-1}$, about $10^5$ to about $10^{12}$ $M^{-1}$, about $10^6$ to about $10^{12}$ $M^{-1}$, about $10^7$ to about $10^{12}$ $M^{-1}$, about $10^8$ to about $10^{12}$ $M^{-1}$, about $10^7$ to about $10^{11}$ $M^{-1}$ about $10^8$ to about $10^{11}$ $M^{-1}$ about $10^7$ to about $10^{10}$ $M^{-1}$, or about $10^8$ to about $10^{10}$ $M^{-1}$. In some embodiments, the binding agent has a $K_A$ of at least about $1\times10^7$ $M^{-1}$ or higher, at least about $1\times10^8$ $M^{-1}$ or higher, at least about $1\times10^9 M^{-1}$ or higher, at least about $1\times10^{10}$ $M^{-1}$ or higher, at least about $1\times10^{11}$ $M^{-1}$ or higher, or at least about $1\times10^{12}$ $M^{-1}$ or higher. In some embodiments, the antibody has a $K_A$ of the antibody 1F5 or antibody 8C7 described herein. In some embodiments, the antibody has a $K_A$ of about $1\times10^9$ $M^{-1}$ to about $1\times10^{10}$ $M^{-1}$ or higher (e.g., affinity of antibody 1F5). In some embodiments, the antibody has a $K_A$ or about $1\times10^8$ $M^{-1}$ to about $1\times10^9$ $M^{-1}$ or higher (e.g., affinity of antibody 8C7).

In some embodiments, the antibody of the disclosure is characterized by an equilibrium dissociation constant ($K_D$=equilibrium dissociation constant or ratio of dissociation rate constant $k_{off}$/association rate constant $k_{on}$) for the sMICA and/or sMICB protein, or the alpha-3 domain thereof, in the range of about $10^{-4}$ to about $10^{-12}$ M, about $10^{-5}$ to about $10^{-12}$ M, about $10^{-6}$ to about $10^{-12}$ M, about $10^{-7}$ to about $10^{-12}$ M, about $10^{-8}$ to about $10^{-12}$ M, about $10^{-7}$ to about $10^{-11}$M, about $10^{-8}$ to about $10^{-11}$M, about $10^{-7}$ to about $10^{-10}$M, or about $10^{-8}$ to about $10^{-10}$M. In some embodiments, the binding agent has a $K_A$ of about $1\times10^{-7}$ M or less, about $1\times10^{-8}$ M or less, about $1\times10^{-9}$ M or less, about $1\times10^{-10}$ M or less, about $1\times10^{-11}$ M or less, or about $1\times10^{-12}$M or less. In some embodiments, the antibody has a $K_D$ of the antibody 1F5 or antibody 8C7 described herein. In some embodiments, the antibody has a $K_D$ of about $1\times10^{-9}$ M to about $1\times10^{-10}$M or less (antibody 1F5). In some embodiments, the antibody has a $K_D$ of about $5\times10^{-9}$ M to about $1\times10^{-10}$ M or less (antibody 8C7).

In some embodiments, the antibody is characterized by a $k_{on}$ association rate constant for the sMICA and/or sMICB protein, or the alpha-3 domain thereof, in the range of about $10^3$ to about $10^9$ $M^{-1}$ $s^{-1}$ or greater, about $10^4$ to about $10^9$ $M^{-1}$ $s^{-1}$ or greater, about $10^5$ to about $10^9$ $M^{-1}$ $s^{-1}$ or greater, about $10^6$ to about $10^9$ $M^{-1}$ $s^{-1}$ or greater, about $10^7$ to about $10^9$ $M^{-1}$ $s^{-1}$ or greater, about $10^4$ to about $10^8$ $M^{-1}$ $s^{-1}$ or greater, or about $10^5$ to about $10^8$ $M^{-1}$ $s^{-1}$ or greater. In some embodiments, the binding agent has a $k_{on}$ association rate constant of at least about $1\times10^3$ $M^{-1}$ $s^{-1}$ or greater, at least about $1\times10^4$ $M^{-1}$ $s^{-1}$ or greater, at least about $1\times10^5$ $M^{-1}$ $s^{-1}$ or greater, at least about $1\times10^6$ $M^{-1}$ $s^{-1}$ or greater, at least about $1\times10^7$ M$^{-1}$ s$^{-1}$ or greater, at least about $1\times10^8$ M$^{-1}$ s$^{-1}$ or greater, or at least about $1\times10^9$ M$^{-1}$ s$^{-1}$ or greater. In some embodiments, the antibody has a $k_{on}$ association rate constant for MICA characteristic of the antibody 1F5 or antibody 8C7 described herein.

In some embodiments, the antibody of the disclosure is characterized by a $k_{off}$ dissociation rate constant for the sMICA and/or sMICB protein, or the alpha-3 domain thereof, of about $10^{-3}$ to about $10^{-10}$ s$^{-1}$ or less, about $10^{-4}$ to about $10^{-10}$ s$^{-1}$ or less, about $10^{-5}$ to about $10^{-10}$ s$^{-1}$ or less, about $10^{-6}$ to about $10^{-10}$ s$^{-1}$ or less, about $10^{-7}$ to about $10^{-10}$ s$^{-1}$ or less, about $10^{-5}$ to about $10^{9}$ s$^{-1}$ or less, about $10^{-6}$ to about $10^{-9}$ s$^{-1}$ or less, about $10^{-5}$ to about $10^{-8}$ s$^{-1}$ or less, or about $10^{-6}$ to about $10^{-8}$ s$^{-1}$ or less. In some embodiments, the binding agent has a $k_{off}$ dissociation rate constant of about $10^{-3}$ s$^{-1}$ or less, about $10^{-4}$ s$^{-1}$ or less, about $10^{-5}$ s$^{-1}$ or less, about $10^{-6}$ s$^{-1}$ or less, about $10^{-7}$ s$^{-1}$ or less, about $10^{-8}$ s$^{-1}$ or less, about $10^{-9}$ s$^{-1}$ or less or about $10^{-10}$ s$^{-1}$ or less. In some embodiments, the antibody has a $k_{off}$ dissociation rate constant for MICA characteristic of the antibody 1F5 or antibody 8C7 described herein.

In some embodiments, the $K_A$ or $K_D$ as well as the $k_{on}$ and $k_{off}$ rate constants can be determined by surface plasmon resonance (SPR) screening, such as by analysis with a BIAcore™ SPR analytical device, as described in Popov et al., 1996, Mol Immunol 33:493-502; and Karlsson et al., 1991, J Immunol Methods 145:229-40, incorporated herein by reference. In some embodiments, the $K_A$ or $K_D$ as well as the $k_{on}$ and $k_{off}$ rate constants can be determined by Bio-Layer Interferometry (BLI), which is based on interference pattern of white light reflected from two surfaces (see, e.g., Rich and Myszka, 2007, Anal Biochem. 361:1-6; Fransson et al., 2010, J Mol Biol. 398(2):214-31) and commercially available as Octet RED96 (ForteBio, Menlo Park, Calif., USA). Other methods for determining affinity and kinetic parameters include equilibrium dialysis and globulin precipitation (see, e.g., Azimzadeh et al., 1990, J Mol Recognit. 3(3):108-16).

In some embodiments, the antibody comprises the antigen binding characteristics of antibody 1F5 or antibody 8C7, described herein and in the Examples. These antibodies bind specifically to the alpha-3 domain of MICA but do not bind to membrane bound MICA expressed in cells. Accordingly, in some embodiments, the antibody comprises a CDR L1, CDR L2, and CDR L3 in the light chain variable region amino acid sequence comprising:

```
                                          (SEQ ID NO: 23)
DIVLTQSPASLAVSLGQRATISCRASKSVSTSGYSYMHWYQQKPGQPPK
LLIYRASNLESGVPARFSGSGSGTDFTLNIHPVEEEDAATYYCQHSREL
PLTFGAGTKLELKR;
``` and a CDR H1, CDR H2 and CDR H3 in the heavy chain variable region amino acid sequence comprising:

```
                                          (SEQ ID NO: 27)
QIQLVQSGPELKKPGETVKISCKASGYTFTDYSVHWVKQAPGKGLKWMG
WINTETGEPTYADDFKGRFAFSLETSASTAYLQINNLKNEDTATYFCAR
AGGNAFAYWGQGTLVTVSA.
```

In some embodiments, the antibody comprises a CDR L1, CDR L2, and CDR L3 in the light chain variable region amino acid sequence comprising:

```
                                          (SEQ ID NO: 31)
DIVMTQAAPSVPVTPGESVSISCRSSKSLLQSNGNTFLYWFMQRPGQS
PQLLIYRMSNLASGVPDRFSGSGSGTAFTLRISRVEAEDVGVYYCMQH
LEYPFTFGGGTKLEIKR;
``` and a CDR H1, CDR H2 and CDR H3 in the heavy chain variable region amino acid sequence comprising:

```
                                          (SEQ ID NO: 35)
QIQLVQSGPELKKPGETVKISCKASGYTFTNYGMNWVKQAPGKGLKWM
GWINTNTGEPTYAEEFKGRFAFSLETSASTAYLQINNLKNEDTATYFC
ARSGGSSPFAYWGQGTLVTVSA.
```

As is understood in the art and as described herein, the amino acid position/boundary delineating the CDR regions of an antibody can vary, depending on the context and the various definitions known in the art. Some positions within the variable regions can be viewed as hybrid CDRs in that the positions can be within a CDR region under one set of criteria while being deemed to be outside a CDR region under a different set of criteria. In some embodiments, the CDRs in the foregoing variable light and variable heavy chains can be delineated using the Kabat, Chothia, or AbM schemes, as described herein, in particular based on the Kabat numbering system. In some embodiments, exemplary CDRs are represented in Table I.

TABLE I

| | KABAT | | |
|---|---|---|---|
| Monoclonal | CDR L1 | CDR L2 | CDR L3 |
| 1F5 VL | RASKSVSTSGYSYMH (SEQ ID NO: 83) | RASNLES (SEQ ID NO: 84) | QHSRELPLT (SEQ ID NO: 85) |
| 8C7 VL | RSSKSLLQSNGNTFLY (SEQ ID NO: 86) | RMSNLAS (SEQ ID NO: 87) | MQHLEYPFT (SEQ ID NO: 88) |
| | CHOTHIA | | |
| Monoclonal | CDR L1 | CDR L2 | CDR L3 |
| 1F5 VL | RASKSVSTSGYSYMH (SEQ ID NO: 83) | RASNLES (SEQ ID NO: 84) | QHSRELPLT (SEQ ID NO: 85) |
| 8C7 VL | RSSKSLLQSNGNTFLY (SEQ ID NO: 86) | RMSNLAS (SEQ ID NO: 87) | MQHLEYPFT (SEQ ID NO: 88) |

TABLE I-continued

AbM

| Monoclonal | CDR L1 | CDR L2 | CDR L3 |
|---|---|---|---|
| 1F5 VL | RASKSVSTSGYSYMH (SEQ ID NO: 83) | RASNLES (SEQ ID NO: 84) | QHSRELPLT (SEQ ID NO: 85) |
| 8C7 VL | RSSKSLLQSNGNTFLY (SEQ ID NO: 86) | RMSNLAS (SEQ ID NO: 87) | MQHLEYPFT (SEQ ID NO: 88) |

KABAT

| Monoclonal | CDR H1 | CDR H2 | CDR H3 |
|---|---|---|---|
| 1F5 VH | DYSVH (SEQ ID NO: 89) | WINTETGEPTYADDFKG (SEQ ID NO: 90) | AGGNAFAY (SEQ ID NO: 91) |
| 8C7 VH | NYGMN (SEQ ID NO: 92) | WINTNTGEPTYAEEFKG (SEQ ID NO: 93) | SGGSSPFAY (SEQ ID NO: 94) |

CHOTHIA

| Monoclonal | CDR H1 | CDR H2 | CDR H3 |
|---|---|---|---|
| 1F5 VH | GYTFTDY (SEQ ID NO: 95) | NTETG (SEQ ID NO: 96) | AGGNAFAY (SEQ ID NO: 91) |
| 8C7 VH | GYTFTNY (SEQ ID NO: 97) | NTNTG (SEQ ID NO: 98) | SGGSSPFAY (SEQ ID NO: 94) |

AbM

| Monoclonal | CDR H1 | CDR 112 | CDR H3 |
|---|---|---|---|
| 1F5 VH | GYTFTDYSVH (SEQ ID NO: 99) | WINTETGEP (SEQ ID NO: 100) | AGGNAFAY (SEQ ID NO: 91) |
| 8C7 VH | GYTFTNYGMN (SEQ ID NO: 101) | WINTNTGEP (SEQ ID NO: 102) | SGGSSPFAY (SEQ ID NO: 94) |

While the CDR sequences above have been defined using Kabat, Chothia, and AbM approaches, it is to be understood that other methods, including the "Contact" approach, IMGT approach (Lefranc et al., 2003) Dev Comp Immunol. 27:55-77) and computational programs such as Paratome (Kunik et al., 2012, Nucl Acids Res. W521-4; www.ofranlab.org/paratome/) can also be used.

In some embodiments, the antibody comprises at least 1, 2, 3, 4, 5 or all 6 of the CDRs in the light chain variable region of amino acid sequence of SEQ ID NO:23 and the heavy chain variable region of amino acid sequence of SEQ ID NO:27. In some embodiments, the antibody comprises at least 1, 2, 3, 4, 5 or all 6 of the CDRs selected from: CDR L1 comprising an amino acid sequence RASKSVSTSGYSYMH (SEQ ID NO:83); CDR L2 comprising an amino acid sequence RASNLES (SEQ ID NO:84); CDR L3 comprising an amino acid sequence QHSRELPLT (SEQ ID NO:85); CDR H1 comprising an amino acid sequence DYSVH (SEQ ID NO:89), GYTFTDY (SEQ ID NO:95) or GYTFTDYSVH (SEQ ID NO:99); CDR H2 comprising an amino acid sequence WINTETGEPTYADDFKG (SEQ ID NO:90), NTETG (SEQ ID NO:96) or WINTETGEP (SEQ ID NO:100); and CDR H3 comprising an amino acid sequence AGGNAFAY (SEQ ID NO:91).

In some embodiments, the antibody comprises at least 1, 2, 3, 4, 5 or all 6 of the CDRs in the light chain variable region of amino acid sequence of SEQ ID NO:31 and the heavy chain variable region of amino acid sequence of SEQ ID NO:35. In some embodiments, the antibody comprises at least 1, 2, 3, 4, 5 or all 6 of the CDRs selected from: CDR L1 comprising an amino acid sequence RSSKSLLQSNGNTFLY (SEQ ID NO:86); CDR L2 comprising an amino acid sequence RMSNLAS (SEQ ID NO:87); CDR L3 comprising an amino acid sequence MQHLEYPFT (SEQ ID NO:88); CDR H1 comprising an amino acid sequence NYGMN (SEQ ID NO:92), GYTFTNY (SEQ ID NO:97) or GYTFTNYGMN (SEQ ID NO:101); CDR H2 comprising an amino acid sequence WINTNTGEPTYAEEFKG (SEQ ID NO:93), NTNTG (SEQ ID NO:98) or WINTNTGEP (SEQ ID NO:102); and CDR H3 comprising an amino acid sequence SGGSSPFAY (SEQ ID NO:94).

In some embodiments, the antibody comprises a CDR L1 comprising an amino acid sequence RASKSVSTSGYSYMH (SEQ ID NO:83); a CDR L2 comprising an amino acid sequence RASNLES (SEQ ID NO:84); a CDR L3 comprising an amino acid sequence QHSRELPLT (SEQ ID NO:85); a CDR H1 comprising an amino acid sequence DYSVH (SEQ ID NO:89), GYTFTDY (SEQ ID NO:95) or GYTFTDYSVH (SEQ ID NO:99); a CDR H2 comprising an amino acid sequence WINTETGEPTYADDFKG (SEQ ID NO:90), NTETG (SEQ ID NO:96), or WINTETGEP (SEQ ID NO:100); and a CDR H3 comprising an amino acid sequence AGGNAFAY (SEQ ID NO:91).

In some embodiments, the antibody comprises a CDR L1 comprising an amino acid sequence RASKSVSTSGYSYMH (SEQ ID NO:83); a CDR L2 comprising an amino acid sequence RASNLES (SEQ ID NO:84); a CDR L3 comprising an amino acid sequence QHSRELPLT (SEQ ID NO:85); a CDR H1 comprising an amino acid sequence DYSVH (SEQ ID NO:89); a CDR H2 comprising an amino acid sequence WINTETGEPTYADDFKG (SEQ ID NO:90); and a CDR H3 comprising an amino acid sequence AGGNAFAY (SEQ ID NO:91).

In some embodiments, the antibody comprises a CDR L1 comprising an amino acid sequence RSSKSLLQSNGNT-FLY (SEQ ID NO:86); a CDR L2 comprising an amino acid sequence RMSNLAS (SEQ ID NO:87); a CDR L3 comprising an amino acid sequence MQHLEYPFT (SEQ ID NO:88); a CDR H1 comprising an amino acid sequence NYGMN (SEQ ID NO:92), GYTFTNY (SEQ ID NO:97), or GYTFTNYGMN (SEQ ID NO:101); a CDR H2 comprising an amino acid sequence WINTNTGEPTYAEEFKG (SEQ ID NO:93), NTNTG (SEQ ID NO:98), or WINTNTGEP (SEQ ID NO:102); and a CDR H3 comprising an amino acid sequence SGGSSPFAY (SEQ ID NO:94).

In some embodiments, the antibody comprises a CDR L1 comprising an amino acid sequence RSSKSLLQSNGNT-FLY (SEQ ID NO:86); a CDR L2 comprising an amino acid sequence RMSNLAS (SEQ ID NO:87); a CDR L3 comprising an amino acid sequence MQHLEYPFT (SEQ ID NO:88); a CDR H1 comprising an amino acid sequence NYGMN (SEQ ID NO:92); a CDR H2 comprising an amino acid sequence WINTNTGEPTYAEEFKG (SEQ ID NO:93); and a CDR H3 comprising an amino acid sequence SGGSSPFAY (SEQ ID NO:94).

In some embodiments, for any of the embodiments above containing one or more CDRs, the CDR sequence may have one or more amino acid substitutions, deletions, and/or insertions, provided the antibody retains the relevant functional properties, e.g., of binding specifically to the alpha 3 domain, or the cryptic epitopes thereof, of MICA and/or MICB. In some embodiments, the CDR sequence has at least 1, 2, 3, 4, 5 or more amino acid substitutions, deletions, and/or insertions. In some embodiments, where the CDR has an amino acid substitution, the substitution comprises a conservative substitution.

In some embodiments, the antibody comprises a light chain variable region VL having at least 80%, 85%, 90%, 91%, 92%, 93%, 94%, 95%, 96%, 97%, 98%, 99% or greater sequence identity to the amino acid sequence of SEQ ID NO:23.

In some embodiments, the antibody comprises a light chain variable region VL having at least 80%, 85%, 90%, 91%, 92%, 93%, 94%, 95%, 96%, 97%, 98%, 99% or greater sequence identity to the amino acid sequence of SEQ ID NO:31.

In some embodiments, the antibody comprises a heavy chain variable region VH having at least 80%, 85%, 90%, 91%, 92%, 93%, 94%, 95%, 96%, 97%, 98%, 99% or greater sequence identity to the amino acid sequence of SEQ ID NO:27.

In some embodiments, the antibody comprises a heavy chain variable region VH having at least 80%, 85%, 90%, 91%, 92%, 93%, 94%, 95%, 96%, 97%, 98%, 99% or greater sequence identity to the amino acid sequence of SEQ ID NO:35.

In some embodiments, the antibody comprises a light chain variable region VL having at least 80%, 85%, 90%, 91%, 92%, 93%, 94%, 95%, 96%, 97%, 98%, 99% or greater sequence identity to the amino acid sequence of SEQ ID NO:23, and a heavy chain variable region VH having at least 80%, 85%, 90%, 91%, 92%, 93%, 94%, 95%, 96%, 97%, 98%, 99% or greater sequence identity to the amino acid sequence of SEQ ID NO:27.

In some embodiments, the antibody comprises a light chain variable region VL having at least 80%, 85%, 90%, 91%, 92%, 93%, 94%, 95%, 96%, 97%, 98%, 99% or greater sequence identity to the amino acid sequence of SEQ ID NO:31, and a heavy chain variable region VH having at least 80%, 85%, 90%, 91%, 92%, 93%, 94%, 95%, 96%, 97%, 98%, 99% or greater sequence identity to the amino acid sequence SEQ ID NO:35.

In some embodiments, the antibody with the defined level of amino acid sequence identity to the light chain variable region has one or more amino acid substitutions, deletions and/or insertions as compared to the VL reference sequence of SEQ ID NO:23 or SEQ ID NO:31. In some embodiments, the antibody comprises 1, 2, 3, 4, 5 or more amino acid substitutions, deletions, and/or insertions as compared to the light chain variable region reference sequence. In some embodiments, in the context of amino acid substitutions, the substitutions comprise conservative amino acid substitutions. In particular, in some embodiments, the conservative substitutions are present on the framework regions (non-CDR regions: $FR_L1$, $FR_L2$, $FR_L3$ and $FR_L4$) of the light chain variable region reference sequence.

In some embodiments, the antibody with the defined level of amino acid sequence identity to the heavy chain variable region has one or more amino acid substitutions, deletions and/or insertions as compared to the VH reference sequence of SEQ ID NO:27 or SEQ ID NO:35. In some embodiments, the antibody comprises 1, 2, 3, 4, 5 or more amino acid substitutions, deletions, and/or insertions as compared to the heavy chain variable region reference sequence. In some embodiments, in the context of amino acid substitutions, the substitutions comprise conservative amino acid substitutions. In particular, in some embodiments, the conservative substitutions are present on the framework regions (non-CDR regions: $FR_H1$, $FR_H2$, $FR_H3$ and $FR_H4$) of the heavy chain variable region reference sequence.

In some embodiments, the antibody comprises a light chain variable region VL comprising an amino acid sequence of SEQ ID NO:23 and a heavy chain variable region VH comprising an amino acid sequence of SEQ ID NO:27.

In some embodiments, the antibody comprises a light chain variable region VL comprising an amino acid sequence of SEQ ID NO:31 and a heavy chain variable region VH comprising an amino acid sequence of SEQ ID NO:35.

In some embodiments, the antibody with any of the specified antigen binding domains can comprise any suitable framework variable region sequence, provided the functional properties of the antigen binding domain in binding to sMICA and/or sMICB, or the alpha-3 domain thereof, are maintained. In some embodiments, the framework sequences are those of rodent variable light chain and heavy chain framework sequences, in particular mouse framework sequences. In some embodiments, the framework sequences of the antibody are those of a human heavy chain consensus framework sequence. Examples of VH consensus framework sequences include: human VH subgroup I consensus framework (SEQ ID NO:103); human VH subgroup II consensus framework (SEQ ID NO:104); human VH subgroup III consensus framework (SEQ ID NO:105); and human VH subgroup VII consensus framework (SEQ ID NO:106) (FIG. 8). In some embodiments, the framework sequences of the antibody comprise a human κ1 light chain consensus framework sequence. Examples of VL consensus framework sequences include: human VL kappa subgroup I consensus framework (SEQ ID NO:107); human VL kappa subgroup II consensus framework (SEQ ID NO:108); human VL kappa subgroup III consensus framework (SEQ ID NO:109); and human VL kappa subgroup IV consensus framework (SEQ ID NO:110) (FIG. 8).

In some embodiments, the antibody with any of the specified antigen binding domains can have a constant domain on the light chain and/or the heavy chain of any origin. The constant domain can be that of rodent, primate, or other mammals. In some embodiments, the constant domain is of human origin. Accordingly, in some embodiments, the antibody with any of the specified antigen binding domains above can have a human constant region, for example, a human light chain constant region CL and/or a human heavy chain constant region. In some embodiments, the human light chain constant region CL comprises a human kappa or human lambda constant region. In some embodiments, the human heavy chain constant region comprises at least one or all of the following: a human CH1, human Hinge, human CH2 and human CH3 domain. In some embodiments, the heavy chain constant region comprises an Fc portion, where the Fc portion is a human $IgG_1$, $IgG_2$, $IgG_3$, $IgG_4$ or IgM isotype.

In some embodiments, the antibody comprises at least 1, 2, 3, 4, 5 or all 6 of the CDRs selected from: CDR L1 comprising an amino acid sequence RASKSVSTSGY-SYMH (SEQ ID NO:83); CDR L2 comprising an amino acid sequence RASNLES (SEQ ID NO:84); CDR L3 comprising an amino acid sequence QHSRELPLT (SEQ ID NO:85); CDR H1 comprising an amino acid sequence DYSVH (SEQ ID NO:89), GYTFTDY (SEQ ID NO:95), or GYTFTDYSVH (SEQ ID NO:99); CDR H2 comprising an amino acid sequence WINTETGEPTYADDFKG (SEQ ID NO:90), NTETG (SEQ ID NO:96), or WINTETGEP (SEQ ID NO:100); and CDR H3 comprising an amino acid sequence AGGNAFAY (SEQ ID NO:91); and a human light chain constant region of human kappa or lambda; and/or a human heavy chain constant region, in particular a human heavy chain constant region comprising at least one or all of: human CH1, human Hinge, human CH2 and human CH3 domain. In such embodiments, the antibody can comprise human framework sequences in the variable regions. In some embodiments, the heavy chain constant region comprises an Fc portion, where the Fc portion is a human $IgG_1$, $IgG_2$, $IgG_3$, $IgG_4$ or IgM isotype.

In some embodiments, the antibody comprises at least 1, 2, 3, 4, 5 or all 6 of the CDRs selected from: CDR L1 comprising an amino acid sequence RSSKSLLQSNGNT-FLY (SEQ ID NO:86); CDR L2 comprising an amino acid sequence RMSNLAS (SEQ ID NO:87); CDR L3 comprising an amino acid sequence MQHLEYPFT (SEQ ID NO:88); CDR H1 comprising an amino acid sequence NYGMN (SEQ ID NO:92), GYTFTNY (SEQ ID NO:97) or GYTFTNYGMN (SEQ ID NO:101); CDR H2 comprising an amino acid sequence WINTNTGEPTYAEEFKG (SEQ ID NO:93), NTNTG (SEQ ID NO:98) or WINTNTGEP (SEQ ID NO:102); and CDR H3 comprising an amino acid sequence SGGSSPFAY (SEQ ID NO:94); and a human light chain constant region (CL) of human kappa or lambda; and/or a human heavy chain constant region, in particular a human heavy chain constant region comprising at least one or all of: human CH1, human Hinge, human CH2 and human CH3 domain. In such embodiments, the antibody can comprise human framework sequences in the variable regions. In some embodiments, the heavy chain constant region comprises an Fc portion, where the Fc portion is a human $IgG_1$, $IgG_2$, $IgG_3$, $IgG_4$ or IgM isotype.

In some embodiments, the antibody comprises a light chain variable region VL comprising an amino acid sequence of SEQ ID NO:23; a heavy chain variable region VH comprising an amino acid sequence of SEQ ID NO:27; a human light chain constant (CL) region of human kappa or lambda; and a human heavy chain constant region, in particular a human heavy chain constant region comprising human CH1, human Hinge, human CH2 and human CH3 domain. In some embodiments, the heavy chain constant region comprises an Fc portion, where the Fc portion is a human $IgG_1$, $IgG_2$, $IgG_3$, $IgG_4$ or IgM isotype.

In some embodiments, the antibody comprises a light chain variable region VL comprising an amino acid sequence of SEQ ID NO:31; a heavy chain variable region VH comprising an amino acid sequence of SEQ ID NO:35; a human light chain constant region (CL) of human kappa or lambda, and a human heavy chain constant region, in particular a human heavy chain constant region comprising human CH1, human Hinge, human CH2 and human CH3 domain. In some embodiments, the heavy chain constant region comprises an Fc portion, where the Fc portion is a human $IgG_1$, $IgG_2$, $IgG_3$, $IgG_4$ or IgM isotype.

In some embodiments, the antibody of the disclosure comprises an antibody or antigen binding fragment which competes for binding to sMICA and/or sMICB, or the alpha-3 domain thereof, with an antibody comprising the antigen binding domain of antibody 1F5, or an antibody comprising the antigen binding domain of antibody 8C7. In some embodiments, the antibody of the disclosure competes for binding to MICA and/or MICB with an antibody comprising: the VL region of SEQ ID NO:23 and a VH region of SEQ ID NO:27. In some embodiments, the antibody of the disclosure competes for binding to sMICA and/or sMICB, or the alpha-3 domain thereof, with an antibody comprising: the VL region of SEQ ID NO:31 and a VH region of SEQ ID NO:35. Competition between antibodies can be determined by an assay in which the antibody of interest or candidate antibody inhibits specific binding of a reference antibody to a common antigen, e.g., alpha-3 domain of MICA or the cryptic epitopes in the alpha-3 domain. Numerous types of competitive binding assays are known, including, for example, solid phase direct or indirect radioimmunoassay (RIA), solid phase direct or indirect enzyme immunoassay (EIA), sandwich competition assay; solid phase direct biotin-avidin EIA; solid phase direct labeled assay, and solid phase direct labeled sandwich assay.

In some embodiments, in light of the high amino acid sequence similarity between MICA and MICB, the antibody presented herein is cross-reactive with sMICA and sMICB proteins, and in particular, cross-reactive with the alpha-3 domain of the sMICA and the alpha-3 domain of the sMICB protein. That is, in some embodiments, the antibody is capable of binding specifically to the sMICA protein and to the sMICB protein. As noted above, these antibodies do not bind specifically to full length MICA and full length MICB, or the extracellular domain of membrane bound form of MICA and membrane bound form of MICB. In some embodiments, the cross-reactive antibody binds to a common epitope (e.g., cryptic epitope) on the MICA and MICB proteins. Exemplary epitopes common between MICA and MICB includes: 217_RQDGV_221, located on the lower side of alpha-3 domain of MICA and MICB (SEQ ID NO:39 and SEQ ID NO:44); 234_LPDGN_238, located near the top of the alpha-3 domain of MICA and MICB (SEQ ID NO:40 and SEQ ID NO:45); and the sequence common between 251_QGEEQR_256 of MICA (SEQ ID NO:41) and 250_RQGEEQR_256 of MICB (SEQ ID NO:46), located on the bottom of the alpha-3 domain.

In some embodiments, the antibody comprises a multimeric antibody containing three or more binding sites, for example an IgM isotype or a synthetically generated multimeric antibody. IgM antibodies generally have four, five or six units of bivalent binding units, i.e., two heavy chains and two light chains assembled into a tetramer, pentamer and/or hexamer. The IgM antibody may or may not have a J chain. Expression of IgM without a J chain forms predominantly hexamers while expression of IgM with J chains forms predominantly pentamers. The multimeric antibodies would promote efficient binding to sMICA and/or sMICB due in part to high avidity resulting from the higher number of antigen binding sites. In some embodiments, IgM antibodies can be obtained by isolating IgM antibodies from immunized animals, by isolating monoclonal antibody producing cell lines (e.g., hybridoma cell lines, etc.) expressing IgM isotype antibody, or transfection/transformation of appropriate cell lines (e.g., CHO, COS, 3T3, PC12, BHK, Vero, C6 glioma, and HeLa) with nucleic acids encoding an IgM antibody or IgM variable heavy and variable light chains, with or without J chains (see, e.g., Azuma et al., 2007, Clin Cancer Res. 13:2745-50; Mader et al., 2013, Advances in Biosci Biotech. 4:38-43; U.S. Pat. No. 7,709,615). In some embodiments, an initially isolated IgG antibody can be class switched to the IgM isotype by expression in appropriate cells lines. For example, Kunert et al., 2004, AIDS Res Hum Retroviruses, 20:755-62 and Wolbank et al., 2003, J Virol. 77:4095-103 describe switching of IgG monoclonal antibodies to IgM isotype. In some embodiments, multimeric antibodies can be generated using single chain antibodies or antibody fragments produced as multimeric antibodies (see, e.g., Power et al., 2003, Methods Mol Biol. 207:335-50; Gail et al., 1999, FEBS Lett. 453(1-2):164-8). The IgM or single chain multimeric antibodies can be purified by techniques known in the art, such as gel filtration chromatography, ion exchange chromatography (e.g., hydroxyapatite), and affinity chromatography (see, e.g., Valasek et al., 2011, BioProcess Int'l. 9(11):28-37; Gagnon et al., 2008, BioPharm Int'l. S26-S36). In some embodiments, the multimeric antibodies can comprise 50% or more hexamer, 60% or more pentamer, or particularly 80% or more pentamer or hexamer IgM molecule. In some embodiments, the IgM or multimeric antibody comprises an antibody binding domain described above, including the various combinations of the CDRs or variable regions of antibody 1F5 or 8C7.

In some embodiments, the binding agent can be a fragment of the antibody of the present disclosure, including portions of the full length antibody, and includes the antigen binding or variable region. Exemplary antibody fragments include Fab, Fab', F(ab')2 and Fv fragments. Proteolytic digestion with papain produces two identical antigen binding fragments, the Fab' fragment, each with a single antigen binding site. Proteolytic digestion with pepsin yields an F(ab')2 fragment that has two antigen binding fragments which are capable of cross-linking antigen, and a residual pFc' fragment. Other types of fragments can include diabodies, linear antibodies, single-chain antibodies, and multispecific antibodies formed from antibody fragments. The antibody fragments are functional in that they retain the desired binding properties, e.g., specific binding to cryptic epitopes in the alpha-3 domain of MICA and/or MICB.

In some embodiments, the antibodies herein can be labeled with a variety of labels, including reporter molecules and detectable labels, such as fluorophores, bioluminescent moieties, luminescent moieties, enzymes, radiolabels, and prosthetic groups. Exemplary enzymes include, among others, horseradish peroxidase, alkaline phosphatase, β-galactosidase, and acetylcholinesterase. Exemplary prosthetic groups include, among others, streptavidin/biotin and digoxigenin. Exemplary fluorophores include, among others, fluorescein, fluorescein isothiocyanate, rhodamine, dichlorotriazinylamine fluorescein, dansyl chloride, Texas Red and phycoerythrin. Exemplary luminescent label includes luminal Exemplary bioluminescent labels include luciferase, luciferin, and aequorin. Exemplary radiolabels include, among others, $^{125}$I, $^{131}$I $^{35}$S, $^{211}$At, $^{90}$Y, $^{186}$Re, $^{188}$Re, $^{14}$C, $^{225}$Ac, $^{212}$Bi, $^{227}$Ac, $^{194}$Os, $^{223}$Ra, $^{149}$Tb, and $^{3}$H.

In some embodiments, the antibody of the disclosure can be conjugated to an effector moiety. The effector moiety includes, among others, antineoplastic agents, drugs, toxins, biologically active proteins, other antibody or antibody fragments, synthetic or naturally occurring polymers, nucleic acids (e.g., DNA and RNA), chelated metals, and nanoparticles. For example, the anti-sMICA or anti-sMICB antibodies can be conjugated to an effector moiety, such as a cytotoxic agent, a radionuclide or drug moiety to modify a given biological response. The effector moiety can be a protein or polypeptide, such as, for example and without limitation, a toxin (e.g., abrin, ricin A, *Pseudomonas* exotoxin, or Diphtheria toxin), a thrombotic agent or an anti-angiogenic agent (e.g., angiostatin or endostatin), or a biological response modifier such as a cytokine or growth factor (e.g., interleukin-I (IL-I), interleukin-2 (IL-2), interleukin-6 (IL-6), granulocyte macrophage colony stimulating factor (GM-CSF), granulocyte colony stimulating factor (G-CSF), or nerve growth factor (NGF)).

In some embodiments, the effector moieties can be cytotoxins or cytotoxic agents. Exemplary cytotoxins and cytotoxic agents include taxol, chlorambucil, cytochalasin B, gramicidin D, ethidium bromide, emetine, mitomycin, etoposide, teniposide, vincristine, vinblastine, colchicine, doxorubicin, daunorubicin, dihydroxyanthracenedione, mitoxantrone, mithramycin, actinomycin D, I-melphalan, puromycin, and analogs or homologs thereof.

Techniques for conjugating such effector moieties to antibodies are well known in the art (see, e.g., Hellstrom et al., Controlled Drug Delivery, 2nd Ed., Robinson et al., eds., pp. 623-53 (1987); Thorpe et al., 1982, Immunol Rev. 62:119-58; Dubowchik et al., 1999, Pharmacol Ther. 83:67-123); and "Antibody-Drug Conjugates and Immunotoxins: From Pre-Clinical Development to Therapeutic Applications," in Cancer Drug Discovery and Development, Gail Lewis Phillips, ed., Springer Publisher (2012)).

In some embodiments, the antibodies of the present disclosure can be attached to polyethylene glycol (PEG) moieties. In some embodiments, the antibody is an antibody fragment. The PEG moieties can be attached through any available amino acid side-chain or terminal amino acid functional group located in the antibody or antibody fragment, for example any free amino, imino, thiol, hydroxyl or carboxyl group. Such amino acids can occur naturally in the antibody or antibody fragment or can be engineered into the antibody or fragment using recombinant DNA methods. Multiple sites can be used to attach two or more PEG molecules. PEG moieties can be covalently linked through a thiol group of at least one cysteine residue located in the antibody or fragment. Where a thiol group is used as the point of attachment, appropriately activated effector moieties (for example, thiol selective derivatives such as maleimides and cysteine derivatives) can be used (see, e.g., Poly(ethyleneglycol) Chemistry and Biological Applications, Milton Harris and S. Zalipsky, eds., American Chemical Society, Washington D.C. (1997); Bioconjugation Protein Coupling Techniques for the Biomedical Sciences, M. Aslam and A. Dent, eds., Grove Publishers, New York, 1998; and Chapman, 2002, Adv Drug Deliv Rev. 54:531-45).

In some embodiments, the antibodies can be prepared as a pharmaceutical composition for treating a disease or disorder associated with elevated levels of MIC protein, as further described below. Accordingly, in some embodiments, provided are pharmaceutical compositions comprising an isolated antibody, including a combination of two or more antibodies, that bind specifically to a cryptic epitope of MICA and/or MICB protein, particularly a cryptic epitope of the alpha-3 domain; and a pharmaceutically acceptable excipient, carrier, or vehicle that are compatible with the antibody preparations. Therapeutic formulations of the antibodies can be prepared for storage as lyophilized formulations or as aqueous solutions by mixing the antibody having the desired degree of purity with optional pharmaceutically acceptable carriers, excipients or stabilizers typically employed in the art (all of which are referred to herein as "carriers"), including, for example, buffering agents, stabilizing agents, preservatives, isotonifiers, non-ionic detergents, antioxidants, and other miscellaneous additives (see, e.g., Remington: The Science and Practice of Pharmacy, 19th Ed., Volumes 1 and 2, Pharmaceutical Press (2012); and Formulation and Process Development Strategies for Manufacturing Biopharmaceuticals, Jameel, F. and Hershenson, S. eds. Wiley (2010); incorporated herein by reference). Such additives are nontoxic to the recipients at the dosages and concentrations employed.

Buffering agents help to maintain the pH in the range which approximates physiological conditions. Suitable buffering agents for use with the binding agents of the present disclosure include both organic and inorganic acids and salts thereof such as citrate buffers, succinate buffers, tartrate buffers, fumarate buffers, gluconate buffers, oxalate buffers, lactate buffers, and acetate buffers. Additionally, phosphate buffers, histidine buffers and trimethylamine salts such as Tris can be used.

In some embodiments, the carrier comprises a preservative to retard microbial growth, and can be present in amounts ranging from 0.2%-1% (w/v). Suitable preservatives for use with antibody preparations include phenol, benzyl alcohol, meta-cresol, methyl paraben, propyl paraben, octadecyldimethylbenzyl ammonium chloride, benzalkonium halides (e.g., chloride, bromide, and iodide), hexamethonium chloride, and alkyl parabens such as methyl or propyl paraben, catechol, resorcinol, cyclohexanol, and 3-pentanol.

In some embodiments, the carrier comprises isotonicifiers, sometimes referred to as "stabilizers" to ensure isotonicity of liquid compositions, examples of which include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive that solubilizes the therapeutic agent or helps prevent denaturation or adherence to the container wall. Exemplary stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc.; organic sugars or sugar alcohols, such as lactose, trehalose, stachyose, mannitol, sorbitol, xylitol, ribitol, myo-inositol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, monothioglycerol and sodium thio sulfate; low molecular weight polypeptides (e.g., peptides of 10 residues or fewer); proteins such as human serum albumin, bovine serum albumin, gelatin or immunoglobulins; hydrophilic polymers, e.g., polyvinylpyrrolidone; monosaccharides, such as xylose, mannose, fructose, glucose; disaccharides such as lactose, maltose, sucrose and trisaccharides such as raffinose; and polysaccharides such as dextran. In some embodiments, stabilizers can be present in the range from 0.1 to 10,000 weight per part of weight active protein.

Non-ionic surfactants or detergents, sometimes referred to as "wetting agents", can be added to help solubilize the therapeutic agent and protect the therapeutic protein against agitation-induced aggregation, which also permits the formulation to be exposed to surface shear stress without causing denaturation of the protein. Suitable non-ionic surfactants include polysorbates (20, 80, etc.), poloxamers (184, 188, etc.), pluronic polyols, and polyoxyethylene sorbitan mono ethers (TWEEN®-20, TWEEN®-80, etc.). In some embodiments, non-ionic surfactants can be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

Sterile injectable solutions of can be prepared by incorporating the antibody in the required amount in an appropriate solvent with one or a combination of ingredients enumerated above, as required, followed by sterilization, such as by microfiltration. Generally, dispersions are prepared by incorporating the active compound into a sterile vehicle that contains a basic dispersion medium and the required other ingredients from those enumerated above and known in the art. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

In some embodiments, the antibodies can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, poly(orthoesters), and polylactic acid. Many methods for the preparation of such formulations are patented or generally known to those skilled in the art (see, e.g., Sustained and Controlled Release Drug Delivery Systems, J. R. Robinson, ed., Marcel Dekker, Inc., New York (1978)).

Various methods of mixing, solubilizing, stabilizing and lyophilizing to prepare the pharmaceutical compositions will use standard conventional techniques applicable to antibody therapeutics (see, e.g., Wang et al., 2007, J Pharm Sci. 96(1):1-26; Remington: The Science and Practice of Pharmacy, 19th Ed., Volumes 1 and 2, Pharmaceutical Press (2012); and Formulation and Process Development Strategies for Manufacturing Biopharmaceuticals, Jameel and Hershenson, eds., Wiley (2010)).

The binding agents of the present disclosure can be prepared by various techniques available to the skilled artisan. The preparation of polyclonal antibodies can employ conventional procedures well-known to those skilled in the art, for example, Green et al., "Production of Polyclonal Antisera," in: Immunochemical Protocols, Manson, ed., Humana Press (1992); Coligan et al., "Production of Polyclonal Antisera in Rabbits, Rats Mice and Hamsters," in: Current Protocols in Immunology, John Wiley & Sons, Inc. (1992), which are hereby incorporated herein by reference.

The preparation of monoclonal antibodies can also use conventional techniques known in the art, for example, Kohler and Milstein, 1975, Nature 256(5517):495-7; Coligan et al., supra, sections 2.5.1-2.6.7; Current Protocols in Immunology, John Wiley & Sons, Inc. (1992); and Antibodies: A Laboratory Manual, Harlow and Lane, eds., Cold Spring Harbor Press, New York (1988); Monoclonal Antibodies: Methods and Protocols in Methods Mol Biol., Vol. 378, Albitar M., ed., Humana Press (2007), which are hereby incorporated herein by reference. Monoclonal antibodies are most frequently generated in mice by administration of the "antigen" and subsequent isolation of B-cells that make antibodies. The B-cells are then immortalized by fusion to another, stable cell type of the same species of the B-cell to create a "hybridoma". An individual B-cell makes one specific antibody (i.e., is clonally monospecific) which is defined by its primary amino acid sequence and its underlying gene sequence. Also, the terms "heterohybridoma" and "heteromyeloma" refer to lymphocyte cell lines immortalized by fusion of lymphocytes and myelomas from two different species. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, e.g., Coligan, et al., supra, sections 2.7.1-2.7.12 and sections 2.9.1-2.9.3; Barnes, et al., Purification of Immunoglobulin G (IgG), in Methods Mol. Biol., Vol. 10, pages 79-104, Humana Press (1992)). An exemplary method for preparing antibodies is described in the Examples.

In some embodiments, the generation of monoclonal antibodies can be achieved using immunogens derived from DNA, peptides, or proteins. Hybridomas are generated by immunizing an animal, which can be for example, a mouse or rabbit, or any animal that will give a suitable antibody response. In some embodiments, immunization is performed by introducing into the animal an antigen-encoding nucleic acid, or a protein antigen, such as MICA/MICB or a fragment thereof (e.g., alpha-3 domain), or a nucleic acid encoding MICA/MICB or an immunogenic fragment thereof. The skilled artisan will appreciate that certain epitopes will be more immunogenic in an animal when removed from their native environment. Thus, a peptide corresponding to an epitope of an antigen conjugated to a carrier such as keyhole limpet hemocyanin, may elicit a stronger antibody response than either the peptide alone or the epitope when part of the native protein on which it is found. Such variations and other immunization schemes are known to the skilled artisan are included in the immunization methods of the disclosure.

Chimeric antibodies, which are antibodies having variable sequences derived from a non-human immunoglobulin, such as rat or mouse antibody, and in some embodiments, human immunoglobulin constant regions, typically chosen from a human immunoglobulin template, can also be prepared by conventional techniques. One method is to clone the non-human genes encoding the variable regions and the human genes encoding the constant regions and recombine them using recombinant techniques to form a chimeric gene. Expression in appropriate cells produces an mRNA encoding the chimeric protein. An alternative process is to use homologous recombination, where a rodent or mouse hybridoma cell line is transfected with a human constant region gene flanked by sequences homologous to the corresponding rodent immunoglobulin constant region gene. At a low frequency the transfected DNA will recombine with the rodent gene resulting in the insertion of the human immunoglobulin constant region gene sequence. Various methods for producing chimeric antibodies are described in Morrison et al., 1984, Proc Natl Acad Sci USA. 81:6851-5; Morrison et al., 1985, Science 229(4719):1202-7; Neuberger et al., 1985, Nature 314:268-71; Oi et al., 1986, BioTechniques 4:214-21; Gillies et at., 1985, Immunol. Methods 125:191-202; U.S. Pat. Nos. 5,807,715; 4,816,567; and 4,816,397; all of which are incorporated herein by reference in their entireties.

In some embodiments, the antibodies herein can be prepared as humanized antibodies, which are chimeric immunoglobulins, immunoglobulin chains or fragments thereof (such as Fv, Fab, Fab', F(ab')2 or other target-binding sub domains of antibodies) which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody can also comprise at least a portion or all of an immunoglobulin constant region, typically that of a human immunoglobulin consensus sequence. Methods of antibody humanization are known in the art, and are described in, for example, Riechmann et at., 1988, Nature 332:323-7; U.S. Pat. Nos. 5,225,539; 5,530, 101; 5,585,089; 5,565,332; 5,693,761; 5,693,762; and 6,180,370; PCT publication WO 91/09967; Padlan, 1991, Mol Immunol 28:489-98; Studnicka et at., 1994, Prot Eng. 7:805-14; and Roguska et at., 1994, Proc Natl Acad Sci USA. 91:969-73; all of which are hereby incorporated herein by reference in their entireties.

Fully human antibodies can be generated using transgenic or trans-chromosomic animals carrying parts of the human immune system rather than the host animal system. These transgenic and trans-chromosomic animals include mice referred to as HuMAb mice and KM mice. The HuMAb Mouse™ (Medarex, Inc.) contains human immunoglobulin gene miniloci that encode un-rearranged human heavy (mu and gamma) and kappa light chain immunoglobulin sequences, together with targeted mutations that inactivate the endogenous mu and kappa chain loci (see, e.g., Lonberg et al., 1994, Nature 368(6474):856-9). Accordingly, the mice exhibit reduced expression of mouse IgM or kappa, and in response to immunization, the introduced human heavy and light chain transgenes undergo class switching and somatic mutation to generate high affinity human IgG kappa monoclonal antibodies (Lonberg, N., 1994, Handbook of Experimental Pharmacology 113:49-101; Lonberg, N. and Huszar, D., 1995, Intern Rev Immunol 13:65-93; and Harding, F. and Lonberg, N., 1995, Ann NY Acad Sci. 764:536-46). The preparation and use of HuMAb mice, and the genomic modifications carried by such mice, are further described in Tuaillon et al., 1994, J Immunol. 152:2912-20; Taylor et al., 1994, International Immunology 6:579-91; Fishwild et al., 1996, Nature Biotech. 14:845-51; U.S. Pat. Nos. 5,545,806; 5,569,825; 5,625,126; 5,633,425; 5,789,650; 5,877,397; 5,661,016; 5,814,318; 5,874,299; 5,770,429; 5,545,807; and PCT publications WO 92103918, WO 93/12227, WO 94/25585, WO 97113852, WO 98/24884; WO 99/45962; and WO 01/14424; the contents of all of which are hereby specifically incorporated herein by reference in their entirety. An alternative transgenic system referred to as the Xenomouse™ (Abgenix, Inc.) can be used, which are described in Green, L L., 1999, J Immunol Methods, 231 (1-2):11-23; U.S. Pat. Nos. 5,939,598; 6,075,181; 6,114, 598; 6,150,584 and 6,162,963, all of which are incorporated herein by reference.

In some embodiments, human antibodies that specifically bind to the epitopes can be raised using a mouse that carries human immunoglobulin sequences on transgenes and transchromosomes, such as a mouse that carries a human heavy chain transgene and a human light chain trans-chromosome, as described in WO 02/043478. In some embodiments, a rabbit system expressing human immunoglobulin genes that can be used to generate fully human antibodies (Rader et al., 2000, J Biol Chem. 275(18):13668-76).

In other embodiments, fully human monoclonal antibodies can be prepared using phage display methods for screening libraries of human immunoglobulin genes. Such phage display methods for isolating human antibodies are established in the art, and are described in, for example, Human Monoclonal Antibodies: Methods and Protocols, Methods Mol Biol., Vol. 1060, Steinitz, M., ed., Humana Press (2013); Marks and Bradbury, 2004, Methods Mol Biol., 248:161-76; Pansri et al., BMC Biotech., 9:6-22; Rader, C., 2012, Methods Mol Biol., 901:53-79; U.S. Pat. Nos. 5,223,409; 5,403,484; 5,571,698; 5,427,908; 5,580,717; 5,969,108; 6,172,197; 5,885,793; 6,521,404; 6,544,731; 6,555,313; 6,582,915 and 6,593,081.

Single chain antibodies, which are fusion proteins of the variable heavy chains and variable light chains of immunoglobulins, can be prepared by phage display methods, where the antigen binding domain is expressed as a single polypeptide and screened for specific binding activity. Alternatively, the single chain antibody can be prepared by cloning the heavy and light chains from a cell, typically a hybridoma cell line expressing a desired antibody. Generally, a linker peptide, typically from 10 to 25 amino acids in length is used to link the heavy and light chains. The linker can be glycine, serine, and/or threonine rich to impart flexibility and solubility to the single chain antibody. Specific methods for generating single chain antibodies are described in, for example, Loffler et al., 2000, Blood 95(6):2098-103; Worn and Pluckthun, 2001, J Mol Biol. 305, 989-1010; Pluckthun, In The Pharmacology of Monoclonal Antibodies, Vol. 113, pp. 269-315, Rosenburg and Moore, eds., Springer-Verlag, New York (1994); U.S. Pat. Nos. 5,840,301; 5,844,093; and 5,892,020; all of which are incorporated herein by reference.

Making antibody fragments are also well known in the art (see, e.g., Antibodies: A Laboratory Manual, Harlow and Lane, eds., Cold Spring Harbor Laboratory, New York (1988), incorporated herein by reference). Antibody fragments can be prepared by proteolytic hydrolysis of the antibody or by expression in E. coli. of DNA encoding the fragment. Antibody fragments can be obtained by pepsin or papain digestion of whole antibodies. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly.

In the embodiments for preparing antibodies of the disclosure, standard techniques may be used for recombinant DNA, oligonucleotide synthesis, tissue culture, and transfection (e.g., electroporation, lipofection, etc.). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification (see, e.g. Sambrook and Russell, Molecular Cloning: A Laboratory Manual, 3rd Ed., Vol. 1-3, Cold Spring Harbor Laboratory Press, Cold Spring Harbor, N.Y. (2001); Antibodies: A Laboratory Manual, Greenfield, E. A., ed., Cold Spring Harbor Laboratory Press, New York (2012); and Current Protocols in Immunology, Coligan et al., eds., Wiley (1999), updates to 2013).

In some embodiments, the isolated antibody can be further purified as measurable by: (1) weight of protein as determined using the Lowry method; (2) to a degree sufficient to obtain at least 15 residues of N-terminal or internal amino acid sequence by use of a spinning-cup sequencer; or (3) to homogeneity by SDS-PAGE under reducing or non-reducing conditions using Coomassie blue or, preferably, silver stain. Various techniques can be used for purifying the antibody, for example by chromatography (e.g., affinity chromatography: Protein A, peptide epitope, etc; ion exchange chromatography; molecular sieve chromatograph; etc.), high performance liquid chromatography, differential solubility, and the like (see, e.g., Fisher, Laboratory Techniques, In Biochemistry And Molecular Biology, Work and Burdon, eds., Elsevier (1980); Antibodies: A Laboratory Manual, Greenfield, E. A., ed., Cold Spring Harbor Laboratory Press, New York (2012)). The purified antibody can be 85% or greater, 90% or greater, 95% or greater, or at least 99% by weight as determined by the foregoing methods.

In another aspect, provided herein are polynucleotides that encode the antibodies or antigen binding regions of the present disclosure. In particular, the polynucleotides are isolated polynucleotides. The polynucleotides may be operatively linked to one or more heterologous control sequences that control gene expression to create a recombinant polynucleotide capable of expressing the polypeptide of interest. Expression constructs containing a heterologous polynucleotide encoding the relevant polypeptide or protein can be introduced into appropriate host cells to express the corresponding polypeptide.

In some embodiments, the polynucleotide encodes a light chain variable region VL having at least 80%, 85%, 90%, 91%, 92%, 93%, 94%, 95%, 96%, 97%, 98%, 99% or greater sequence identity to the amino acid sequence of SEQ ID NO:23. In some embodiments, the polynucleotide encodes a heavy chain variable region VH having at least 80%, 85%, 90%, 91%, 92%, 93%, 94%, 95%, 96%, 97%, 98%, 99% or greater sequence identity to the amino acid sequence of SEQ ID NO:27.

In some embodiments, the polynucleotide encodes a light chain variable region VL having at least 80%, 85%, 90%, 91%, 92%, 93%, 94%, 95%, 96%, 97%, 98%, 99% or greater sequence identity to the amino acid sequence of SEQ ID NO:31. In some embodiments, the polynucleotide encodes a heavy chain variable region VH having at least 80%, 85%, 90%, 91%, 92%, 93%, 94%, 95%, 96%, 97%, 98%, 99% or greater sequence identity to the amino acid sequence of SEQ ID NO:35.

In some embodiments, the polynucleotide encodes a light chain variable region VL comprising the amino acid sequence of SEQ ID NO:23. In some embodiments, the polynucleotide encodes a heavy chain variable region VH comprising the amino acid sequence of SEQ ID NO:27. In some embodiments, the polynucleotide encodes a light chain variable region VL comprising the amino acid sequence of SEQ ID NO:31. In some embodiments, the polynucleotide encodes a heavy chain variable region VH comprising the amino acid sequence of SEQ ID NO:35.

In some embodiments, the polynucleotide encodes one or more CDRs selected from: a CDR L1 comprising an amino acid sequence of SEQ ID NO:83; CDR L2 comprising an amino acid sequence SEQ ID NO:84; CDR L3 comprising an amino acid sequence of SEQ ID NO:85; CDR H1 comprising an amino acid sequence of SEQ ID NO:89; CDR H1 comprising an amino acid sequence of SEQ ID NO:95; CDR H1 comprising an amino acid sequence of SEQ ID NO:99; CDR H2 comprising an amino acid sequence of SEQ ID NO:90; CDR H2 comprising an amino acid sequence of SEQ ID NO:96; CDR H2 comprising an amino acid sequence of SEQ ID NO:100; and CDR H3 comprising an amino acid sequence of SEQ ID NO:91.

In some embodiments, the polynucleotide encodes one or more CDRs selected from: a CDR L1 comprising an amino acid sequence of SEQ ID NO:86; CDR L2 comprising an amino acid sequence of SEQ ID NO:87; CDR L3 comprising an amino acid sequence of SEQ ID NO:88; CDR H1 comprising an amino acid sequence of SEQ ID NO:92; CDR H1 comprising an amino acid sequence of SEQ ID NO:97; CDR H1 comprising an amino acid sequence of SEQ ID NO:101; CDR H2 comprising an amino acid sequence of SEQ ID NO:93; CDR H2 comprising an amino acid sequence of SEQ ID NO:98; CDR H2 comprising an amino acid sequence of SEQ ID NO:102; and CDR H3 comprising an amino acid sequence of SEQ ID NO:94.

In some embodiments, the polynucleotide encodes at least 1, 2, 3, 4, 5 or all 6 of the CDRs in the light chain variable region of amino acid sequence of SEQ ID NO:23 and the heavy chain variable region of amino acid sequence of SEQ ID NO:27. In some embodiments, the polynucleotide encodes at least 1, 2, 3, 4, 5 or all 6 of the CDRs selected from: CDR L1 comprising an amino acid sequence of SEQ ID NO:83; CDR L2 comprising an amino acid sequence of SEQ ID NO:84; CDR L3 comprising an amino acid sequence of SEQ ID NO:85; CDR H1 comprising an amino acid sequence of SEQ ID NO:89, SEQ ID NO:95, or SEQ ID NO:99; CDR H2 comprising an amino acid sequence of SEQ ID NO:90, SEQ ID NO:96, or SEQ ID NO:100; and CDR H3 comprising an amino acid sequence of SEQ ID NO:91.

In some embodiments, the polynucleotide encodes at least 1, 2, 3, 4, 5 or all 6 of the CDRs in the light chain variable region of amino acid sequence of SEQ ID NO:31 and the heavy chain variable region of amino acid sequence of SEQ ID NO:35. In some embodiments, the polynucleotide encodes at least 1, 2, 3, 4, 5 or all 6 of the CDRs selected from: CDR L1 comprising an amino acid sequence of SEQ ID NO:86; CDR L2 comprising an amino acid sequence of SEQ ID NO:87; CDR L3 comprising an amino acid sequence of SEQ ID NO:88; CDR H1 comprising an amino acid sequence of SEQ ID NO:92, SEQ ID NO:97, or SEQ ID NO:101; CDR H2 comprising an amino acid sequence of SEQ ID NO:93, SEQ ID NO:98, or SEQ ID NO:102; and CDR H3 comprising an amino acid sequence of SEQ ID NO:94.

As will be apparent to the skilled artisan, the knowledge of a protein sequence provides a description of all the polynucleotides capable of encoding the subject protein sequence because of the knowledge of the all possible codons corresponding to the various amino acids. An extremely large number of nucleic acids encoding the forgoing polypeptides can be made by selecting combinations based on the possible codon choices, and all such variations are to be considered specifically disclosed for the polypeptide described herein.

In some embodiments, the polynucleotide has at least about 80%, 85%, 86%, 87%, 88%, 89%, 90%, 91%, 92%, 93%, 94%, 95%, 96%, 97%, 98%, or 99% or more sequence identity at the nucleotide level to: (a) a reference polynucleotide sequence of SEQ ID NO:25, and encodes the polypeptide of SEQ ID NO:23, or (b) a reference polynucleotide sequence of SEQ ID NO:24, and encodes a polypeptide comprising residues 1 to 132 of SEQ ID NO:22. In some embodiments, the polynucleotide has at least about 80%, 85%, 86%, 87%, 88%, 89%, 90%, 91%, 92%, 93%, 94%, 95%, 96%, 97%, 98%, or 99% or more sequence identity at the nucleotide level to: (a) a reference polynucleotide sequence of SEQ ID NO:29, and encodes the polypeptide of SEQ ID NO:27, or (b) a reference polynucleotide sequence of SEQ ID NO:28, and encodes a polypeptide comprising residues 1 to 136 of SEQ ID NO:26. In some embodiments, the polynucleotide has about 80%, 85%, 86%, 87%, 88%, 89%, 90%, 91%, 92%, 93%, 94%, 95%, 96%, 97%, 98%, or 99% or more sequence identity at the nucleotide level to: (a) a reference polynucleotide sequence of SEQ ID NO:33, and encodes the polypeptide of SEQ ID NO:31, or (b) a reference polynucleotide sequence of SEQ ID NO:32, and encodes a polypeptide comprising residues 1 to 133 of SEQ ID NO:30. In some embodiments, the polynucleotide has about 80%, 85%, 86%, 87%, 88%, 89%, 90%, 91%, 92%, 93%, 94%, 95%, 96%, 97%, 98%, or 99% or more sequence identity at the nucleotide level to: (a) a reference polynucleotide sequence of SEQ ID NO:37, and encodes the polypeptide of SEQ ID NO:35, or (b) a reference polynucleotide sequence of SEQ ID NO:36, and encodes a polypeptide comprising residues 1 to 137 of SEQ ID NO:34.

In some embodiments, the polynucleotides herein may be manipulated in a variety of ways to provide for expression of the encoded polypeptide. In some embodiments, the polynucleotide is operably linked to control sequences, including among others, transcription promoters, leader sequences, transcription enhancers, ribosome binding or entry sites, termination sequences, and polyadenylation sequences for expression of the polynucleotide and/or corresponding polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., Molecular Cloning: A Laboratory Manual, 3rd Ed., Cold Spring Harbor Laboratory Press, New York (2001); and Current Protocols in Molecular Biology, Ausubel. F. ed., Greene Pub. Associates (1998), updates to 2013.

In some embodiments, the polynucleotides can be part of an expression vector, where the vector and polynucleotide includes one or more operably linked control sequences for controlling expression of the polynucleotide and/or expression of the encoded polypeptide. The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids. Exemplary expression vectors include, among others, vectors based on T7 or T7lac promoters (pACY: Novagen; pET); vectors based on Baculovirus promoters (e.g., pBAC); vectors based on Ef1-α and HTLV promoters (e.g., pFUSE2; Invitrogen, CA, USA); vectors based on CMV enhancer and human ferritin light chain gene promoters (e.g., pFUSE: Invitrogen, CA, USA); vectors based on CMV promoters (e.g, pFLAG: Sigma, USA); and vectors based on dihydrofolate reductase promoters (e.g., pEASE: Amgen, USA). Various vectors can be used for transient or stable expression of the polypeptides of interest.

In another aspect, the polynucleotide encoding a polypeptide is operatively linked to one or more control sequences for expression of the polypeptide in a host cell. Host cells for use in expressing the polypeptides are well known in the art and include, but are not limited to, bacterial cells, such as E. coli, yeast cells; insect cells such as Drosophila S2 and Spodoptera Sf9 cells; animal cells such as Chinese Hamster Ovary (CHO), African Green Monkey kidney (COS), baby hamster kidney (BHK), mouse myelomas (e.g., NS0 and Sp2/0), and human embryo kidney (HEK); and plant cells. Appropriate culture mediums and growth conditions for the above-described host cells are well known in the art. In some embodiments, the host cells and the expression vectors are used to express the polypeptides of interest.

In some embodiments, the host cells comprising the expression vectors and polynucleotides described herein are cultured in suitable media and under culture conditions appropriate for expression of the encoded polypeptide, for example the polypeptides comprising SEQ ID NO:23, SEQ ID NO:27, SEQ ID NO:31, and/or SEQ ID NO:35. In some embodiments, an in vitro expression system can be used with the expression vectors to express the polypeptide. In vitro expression systems include those based on E. coli., rabbit reticulocyte, wheat germ, insect cells, and human cells. Whether expressed in a host cell or in vitro, the expressed polypeptides can be isolated or purified, as further described herein.

In another aspect, for preparing the antibodies of the disclosure, the MIC polypeptides and the epitopes can be part of immunogens for eliciting the production of antibodies. Accordingly, in some embodiments, the present disclosure provides an immunogen for preparing an antibody described herein. In some embodiments, the immunogen comprises a peptide within the alpha-3 domain of MICA or MICB protein. As noted herein, the immunogen of an alpha-3 domain can comprise a polypeptide region from amino acid residues 205 to 297 of the full length MICA of the MICA*001 allele, or full length MICB protein of the MICB*001 allele. In some embodiments, where the extracellular domain or alpha-3 domain is used an immunogen, antibodies that bind specifically to cryptic epitopes can be prepared by affinity techniques using peptides containing epitope sequences. Alternatively, for preparing monoclonal antibodies, the antibodies can be screened for specific binding using the peptide containing the epitope (e.g., cryptic) sequences.

In some embodiments, the immunogen comprises a cryptic epitope of the alpha-3 domain of MICA or MICB, for example the cryptic epitope within amino acid residues 187 to 297, particularly amino acid residues 187 to 274, more particularly amino acid residues 190 to 256 of MICA or MICB as described above. Generally, polypeptide or peptides are selected that retain the 3-dimensional structure present in the naturally occurring extracellular domain of the MIC protein, for example sMICA and sMICB.

In some embodiments, the immunogen comprises a peptide within a subsequence of the alpha-3 domain, wherein the subsequence is selected from:
    amino acid residues 190 to 229;
    amino acid residues 190 to 238;
    amino acid residues 217 to 238;
    amino acid residues 243 to 256
    amino acid residues 243 to 274; and
    amino acid residues 243 to 296/297
of MICA or MICB, as described herein, where the amino acid positions are defined with respect to the MICA protein of the MICA*001 allele and the MICB protein of the MICB*001 allele, respectively.

In some embodiments, the immunogen comprises a peptide within the alpha-3 domain comprising a sequence selected from:
    amino acid residues 190 to 196;
    amino acid residues 217 to 221;
    amino acid residues 234 to 238;
    amino acid residues 250 to 256; and
    amino acid residues 251 to 256
of MICA (amino acid numbering based on *001 allele), including the corresponding region in any of the alleles of MICA existing in the human population, such as the identified MICA alleles available in Robinson et al., 2003, "IMGT/HLA and IMGT/MHC: Sequence databases for the study of the major histocompatibility complex", Nucleic Acids Res. 31:311-314 and the Anthony Nolan Research Institute world wide web site www.anthonynolan.org.uk/HIG/data.html; which are incorporated herein by reference.

In some embodiments, immunogen comprises a peptide within the alpha-3 domain comprising a sequence selected from:
    amino acid residues 190 to 196;
    amino acid residues 217 to 221;
    amino acid residues 234 to 238; and
    amino acid residues 250 to 256
of MICB (amino acid numbering based on *001 allele), including the region in any of the alleles of MICB existing in the human population, such as the identified MICB alleles available in Robinson et al., 2003, "IMGT/HLA and IMGT/MHC: Sequence databases for the study of the major histocompatibility complex", Nucleic Acids Res. 31:311-314 and the Anthony Nolan Research Institute world wide web site www.anthonynolan.org.uk/HIG/data.html; which are incorporated herein by reference.

In some embodiments, the immunogen comprises a peptide, where the peptide comprises a sequence:
    190_RSEASEG_196, located on bottom of alpha-3 domain (SEQ ID NO:38);
    217_RQDGV_221, located on lower side of alpha-3 domain (SEQ ID NO:39);
    234_LPDGN_238, located near the top of alpha-3 domain (SEQ ID NO:40); or
    251_QGEEQR_256, located on bottom of alpha-3 domain (SEQ ID NO:41),
where the amino acid positions are defined with respect to the MICA protein of the MICA*001 allele.

In some embodiments, the immunogen comprises a peptide, where the peptide comprises a sequence:
    251_RGEEQR_256, located on bottom of alpha-3 domain (SEQ ID NO:42),
wherein the amino acid residue numbering is in reference to the MICA protein of the MICA*001 allele. As noted above, this epitope is found in, but not limited to, MICA alleles *005, *008:01:01; *008:01:02; *008:02; *008: 03; *008:04; *008:05; *010:01; *010:02; *013; *016; *019; *022; *027; *033; *035; *037; *039; *042; *048; *053; *054; *056; *058; *062; *069; *070; *073; and *076.

In some embodiments, immunogen comprises a peptide, where the peptide comprises a sequence:
    190_CSEVSEG_196, located on bottom of alpha-3 domain (SEQ ID NO:43);
    217_RQDGV_221, located on lower side of alpha-3 domain (SEQ ID NO:44);

234_LPDGN_238, located near the top of alpha-3 domain (SEQ ID NO:45); or

250_RQGEEQR_256, located on bottom of alpha-3 domain (SEQ ID NO:46), where the amino acid positions are defined with respect to the MICB protein of the MICB*001 allele.

In some embodiments, the immunogen comprises a peptide, where the peptide comprises an amino acid sequence:

(a)

(SEQ ID NO: 47)
~$X^{41}$-S-$X^{43}$-$X^{44}$-S-E-G~, wherein $X^{41}$ is selected from R and C; $X^{43}$ is selected from E and K; and $X^{44}$ is selected from A and V;

(b)

(SEQ ID NO: 48)
~R-Q-D-G-$X^{B5}$~, wherein $X^{B5}$ is selected from V and L;

(c)

(SEQ ID NO: 49)
~$X^{D1}$-$X^{D2}$-G-E-E-Q-$X^{D7}$~, wherein $X^{D1}$ is selected from C or R; $X^{D2}$ is selected from Q, R and E; and $X^{D7}$ is selected from R, S and K; or (d)

(SEQ ID NO: 50)
~L-P-D-G-N~.

In some embodiments, the specific sequences described above can have additional amino acids appended to the amino and/or carboxy terminal ends, where the additional amino acids can be those found on the naturally occurring MICA or MICB amino acid sequence surrounding the defined region or the defined amino acid sequence. In some embodiments, the peptide immunogens can have additional 1, 2, 3, 4, 5, 10, 15, 20, 25, 30, 35, 40, 45, 50 amino acids at the amino terminal and/or carboxy terminal ends of the specific immunogen peptide sequences.

In some embodiments, an exemplary immunogen for generating antibodies that bind to cryptic epitopes in the alpha-3 domain of MICA comprises a peptide selected from:

(a)

(SEQ ID NO: 52)
182_VPPMVNVTRSEASEGNITVTCRASGFYPWNITLSWRQDGVSLSHD
TQQWGDVLPDGNGTYQTWVATRICQGEEQRFTCYMEHSGNHSTHPVP
S_274;

(b)

(SEQ ID NO: 53)
243_TWVATRICQGEEQRFTCYMEHSGNHSTHPVPS_274;

(c)

(SEQ ID NO: 54)
190_RSEASEGNITVTCRASGFYPWNITLSWRQDGVSLSHDTQQWGDVL
PDGNGTYQTWVATRICQGEEQRFTCYMEHSGNHSTHPVPS_274;

(d)

(SEQ ID NO: 55)
190_RSEASEGNITVTCRASGFYPWNITLSWRQDGVSLSHDTQQWGDVL
PDGNGTYQTWVATRICQGEEQRFTCYMEHSGNHSTH_270;
and (e)

(SEQ ID NO: 56)
190_RSEASEGNITVTCRASGFYPWNITLSWRQDGVSLSHDTQQWGDVL
PDGNGTYQTWVATRICQGEEQR_256, where the amino acid numbering is based on the mature, processed MICA protein of the MICA*001 allele.

In some embodiments, an exemplary immunogen for generating antibodies that bind to cryptic epitopes in the alpha-3 domain of MICB comprises a peptide selected from:

(a)

(SEQ ID NO: 57)
182_VPPMVNVTCSEVSEGNITVTCRASSFYPRNITLTWRQDGVSLSHN
TQQWGDVLPDGNGTYQTWVATRIRQGEEQRFTCYMEHSGNHGTHPVP
S_274;

(b)

(SEQ ID NO: 58)
243_TWVATRIRQGEEQRFTCYMEHSGNHGTHPVPS_274;

(c)

(SEQ ID NO: 59)
190_CSEVSEGNITVTCRASSFYPRNITLTWRQDGVSLSHNTQQWGDVLP
DGNGTYQTWVATRIRQGEEQRFTCYMEHSGNHGTHPVPS_274;

(d)

(SEQ ID NO: 60)
190_CSEVSEGNITVTCRASSFYPRNITLTWRQDGVSLSHNTQQWGDVLP
DGNGTYQTWVATRIRQGEEQRFTCYMEHSGNHGTH_270;
and (e)

(SEQ ID NO: 61)
190_CSEVSEGNITVTCRASSFYPRNITLTWRQDGVSLSHNTQQWGDVLP
DGNGTYQTWVATRIRQGEEQR_256, where the amino acid numbering is based on the mature, processed MICB protein of the MICB*001 allele.

In some embodiments, the immunogen peptides described herein can have additional amino acids appended, where the amino acids are not part of the naturally occurring amino acid sequence present on MICA or MICB, for example, to increase the immunogenicity of the peptides; and/or provide functional groups, such as amino groups, imino groups, cysteine groups, or carboxy groups for coupling the peptide to immunogenic carriers. Other heterologous sequence that can be appended include, among others, purification sequences (e.g., His tag); cleavage sequences (e.g., protease recognition sequences); and epitope tags (e.g., c-myc, GFP, hemagglutinin, etc.). The heterologous sequences can be 1, 2, 3, 4, 5, 10, 15, 20, 25, 30, 35, 40, 45, 50 or more amino acids at the amino terminal and/or carboxy terminal ends.

In some embodiments, the peptides containing the cryptic epitopes can be prepared as fusion proteins, such as by chemical synthesis or recombinant techniques. Particularly useful are fusion proteins that increase the immunogenicity of the attached peptide containing the defined epitopes. In some embodiments, one or more of the peptides defining the epitopes above can be linked together, such as a head to tail arrangement to produce fusions of the peptides. In some embodiments, a linker, for example glycine, serine, and/or threonine containing linkers, can be used to connect the peptides to provide some structural flexibility to the fusion constructs. These fused peptides can be prepared by chemical synthesis, or prepared by recombinant methods using nucleic acid constructs designed to express the fused peptides, with or without linkers. In some embodiments, the peptides can be cyclized to promote its immunogenic properties In some embodiments, the peptides can be produced as fusion proteins, where the fusion is to a T cell epitope that can elicit strong humoral response to the peptide epitope. These T cell epitopes, sometimes referred to as T helper cell (Th) epitopes, comprise sequences of about 15-30 amino acids with common structural features (see, e.g., Cease et al., 1987, Proc Natl Acad Sci USA. 84:4249-53; U.S. Pat. No. 5,759,551 and U.S. patent publication 20030027979; all of which are incorporated herein by reference). Some pathogen derived T helper cell epitopes include, among others, FFLL-TRILTIPQSLD (SEQ ID NO:62); KKLRRLLYMIYMS-GLAVRVHVSKEEQY (SEQ ID NO:63); KKQYIKANSK-FIGITEL (SEQ ID NO:64); KKFNNFTVSFWLRVPKVSASHL (SEQ ID NO:65); YMSGLAVRVHVSKEE (SEQ ID NO:66); YDPNYL-RTDSDKDRFLQTMVKLFNRIK (SEQ ID NO:67); GAYARCPNGTRALTVAELRGNAEL (SEQ ID NO:68); LSEIKGVIVHRLEGV (SEQ ID NO:69); GILESRGIKAR-ITHVDTESY (SEQ ID NO:70); WVRDIIDDFTNESSQKT (SEQ ID NO:71); and DVSTIVPYIGPALNHV (SEQ ID NO:72). Other such Th epitopes are described in the art, such as in U.S. patent publication 20030027979, incorporated herein by reference.

In some embodiments, the peptides are coupled to a suitable carrier for imparting or increasing the immunogenicity of the peptides. Suitable carriers include, among others, tetanus toxoid, diphtheria toxoid, keyhole limpet hemocyanin (KLH), Concholepas concholepas hemocyanin, and cationized bovine serum albumin (cBSA).

In some embodiments, the immunogen above can be prepared as an immunogen composition, such as with an adjuvant. Suitable adjuvants include, among others, Complete Freund's adjuvant (CFA), which is typically composed of a mineral oil, an emulsifying agent, and killed mycobacteria, such as *Mycobacterium tuberculosis*. Aqueous antigen solutions are mixed with these components to create a water-in-oil emulsion. In some embodiments, the adjuvant is Incomplete Freund's adjuvant (IFA), which is similar to CFA but does not include the bacterial component. Other adjuvants that can be used include, among others, muramyl dipeptide (MDP) the minimal unit of the mycobacterial cell wall complex that generates the adjuvant activity observed with CFA (see, e.g., Chedid et al., 1978, Prog Allergy 25:63-105; Byars et al., 1987, Vaccine 5:223-8; Chedid et al., Infect Immun. 35:417-24; Gisler et al., Immunomodulations of Microbial Products and Related Synthetic Compounds, Y. Yamamura and S. Kotani, eds., pg. 167, Excerpta Medica, Amsterdam (1981); and Ellouz et al., 1974, Biochem Biophys Res Commun. 59:1317-25); MF59, a highly immunogenic, submicron oil-in-water emulsion sub-micron oil-in-water emulsion of a squalene, polyoxyethylene sorbitan monooleate (Tween™ 80) and sorbitan trioleate (see, e.g., Ott et al., "MF59-Design and Evaluation of a Safe and Potent Adjuvant for Human Vaccines" in Vaccine Design: The Subunit and Adjuvant Approach, Powell, M. F. and Newman, M. J. eds., pg. 277-96, Plenum Press, New York (1995); and AS04 and AS02, which are oil in water emulsions containing MPL™, a series of 4'-monophosphoryl lipid A species that vary in the extent and position of fatty acid substitution.

In some embodiments, the antibodies of the present disclosure can be prepared by immunizing an animal with any of the described immunogens under conditions sufficient to elicit an antibody response; and isolating the antibody.

In some embodiments, the antibodies generated can be screened for the desired binding properties, e.g., binding to sMIC protein but not to a MIC polypeptide comprising an alpha-3 domain and a transmembrane domain (e.g., full length MIC protein), or a membrane bound MICA or MICB.

Accordingly, in some embodiments, the method of screening for the antibodies of the present disclosure can comprise:

(a) contacting a candidate antibody with sMICA or sMICB under conditions suitable for the antibody to interact with the sMICA or sMICB;

(b) contacting the antibody with a MICA or MICB polypeptide comprising an alpha-3 domain and a transmembrane domain, or a membrane bound MICA or MICB; and (c) determining whether the antibody binds specifically to the sMICA or sMICB but does not bind specifically to the MICA or MICB polypeptide comprising the alpha-3 domain and the transmembrane domain, or the membrane bound MICA or MICB.

In some embodiments, the method of screening for the antibodies of the present disclosure can comprise:

(a) contacting a candidate antibody with a polypeptide comprising an alpha-3 domain of MICA or MICB under conditions where a cryptic epitope on the alpha-3 domain is capable of interacting with the antibody;

(b) contacting the candidate antibody with a MICA or MICB polypeptide comprising an alpha-3 domain and a transmembrane domain, or a membrane bound MICA or MICB; and (c) determining whether the antibody binds specifically to the alpha-3 domain of MICA or MICB but does not bind specifically to the MICA or MICB polypeptide comprising the alpha-3 domain and the transmembrane domain, or the membrane bound MICA or MICB.

In some embodiments, the method of screening for the antibodies of the present disclosure can comprise:

(a) contacting a candidate antibody with a cryptic epitope on the alpha-3 domain of MICA under conditions where the cryptic epitope is capable of interacting with the antibody;

(b) contacting the candidate antibody with a MICA or MICB polypeptide comprising an alpha-3 domain and a transmembrane domain, or a membrane bound MICA or MICB; and (c) determining whether the antibody binds specifically to the cryptic epitope of MICA but does not bind specifically to MICA or MICB polypeptide comprising the alpha-3 domain and the transmembrane domain, or the membrane bound MICA or MICB.

In some embodiments, the method of screening for the antibodies of the present disclosure can comprise:

(a) contacting a candidate antibody with a cryptic epitope on the alpha-3 domain of MICB under conditions where the epitope is capable of interacting with the antibody;

(b) contacting the candidate antibody with a MICA or MICB polypeptide comprising an alpha-3 domain and a transmembrane domain, or a membrane bound MICA or MICB; and (c) determining whether the antibody binds specifically to the cryptic epitope of MICB but does not bind specifically to MICA or MICB polypeptide comprising the alpha-3 domain and the transmembrane domain, or the membrane bound MICA or MICB.

In some embodiments of the screening methods, the MICA or MICB polypeptide comprising an alpha-3 domain and a transmembrane domain can be a full length MICA or full length MICB protein, respectively, either in its full length unprocessed or processed form.

In some embodiments, any of the polypeptides described herein, including the specific cryptic peptides can be used for screening the antibodies. In some embodiments, the cryptic peptide used for screening can comprise a sequence represented by:

amino acid residues 190 to 229;
amino acid residues 190 to 238;
amino acid residues 217 to 238;
amino acid residues 243 to 256
amino acid residues 243 to 274; and
amino acid residues 243 to 296/297 of MICA or MICB protein, where the amino acid positions are defined with respect to the MICA protein of the MICA*001 allele or the MICB protein of the MICB*001 allele, respectively.

In some embodiments, the cryptic peptide used for screening can comprise a sequence:
190_RSEASEG_196, located on bottom of alpha-3 domain (SEQ ID NO:38);
217_RQDGV_221, located on lower side of alpha-3 domain (SEQ ID NO:39);
234_LPDGN_238, located near the top of alpha-3 domain (SEQ ID NO:40);
251_QGEEQR_256, located on bottom of alpha-3 domain (SEQ ID NO:41); or
251_RGEEQR_256, located on bottom of alpha-3 domain (SEQ ID NO:42), where the amino acid positions are defined with respect to the MICA protein of the MICA*001 allele.

In some embodiments, the cryptic peptide used for screening can comprise a sequence:
190_CSEVSEG_196, located on bottom of alpha-3 domain (SEQ ID NO:43);
217_RQDGV_221, located on lower side of alpha-3 domain (SEQ ID NO:44);
234_LPDGN_238, located near the top of alpha-3 domain (SEQ ID NO:45); or
250_RQGEEQR_256, located on bottom of alpha-3 domain (SEQ ID NO:46), where the amino acid positions are defined with respect to MICB protein of the MICB*001 allele.

In some embodiments, the peptide use for screening can comprise a sequence:

(a)
$$\sim X^{41}\text{-}S\text{-}X^{43}\text{-}X^{44}\text{-}S\text{-}E\text{-}G\sim,$$
(SEQ ID NO: 47)

wherein $X^{41}$ is selected from R and C; $X^{43}$ is selected from E and K; and $X^{44}$ is selected from A and V;

(b)
$$\sim R\text{-}Q\text{-}D\text{-}G\text{-}X^{B5}\sim,$$
(SEQ ID NO: 48)

wherein $X^{B5}$ is selected from V and L;

(c)
$$\sim X^{D1}\text{-}X^{D2}\text{-}G\text{-}E\text{-}E\text{-}Q\text{-}X^{D7}\sim,$$
(SEQ ID NO: 49)

wherein $X^{D1}$ is selected from C or R; $X^{D2}$ is selected from Q, R and E; and $X^{D7}$ is selected from R, S and K; or (d)
$$\sim L\text{-}P\text{-}D\text{-}G\text{-}N\sim.$$
(SEQ ID NO: 50)

In some embodiments of the screening method, the candidate antibody is assessed for insignificant autoimmune disease inducing activity. In some embodiments, the candidate antibody is assessed for insignificant antagonistic activity against binding of MIC protein to its cognate receptor NKG2D.

Conditions suitable for screening can be those used in conventional screening procedures, for example, incubation of cells or polypeptides with the antibodies in aqueous buffered solutions followed by several washings. In some embodiments, the peptide containing the epitopes or MIC protein expressing cells can be immobilized on a solid surface, such as a membrane or plate, which is then contacted with the candidate antibodies. Non-specifically bound antibodies can be washed away with solutions containing non-specific competing agent, such as a suitable blocking agent. Exemplary contacting conditions may comprise incubation on ice or at 4° C. for between 30 minutes and 4 hours. Alternatively, carrying out the contacting step at room temperature or 37° C. is possible and may be preferable in some cases. In addition, appropriate reagents such as blocking agents can be used to reduce non-specific binding, for example, bovine serum albumin, non-ionic detergents (e.g., NP40, Triton X100, Tween20, etc.), or other suitable blocking agent (e.g., non-fat milk). It will be appreciated that the contacting conditions can be varied and adapted by a skilled person depending on the aim of the screening method. For example, if the incubation temperature is increased, for example to room temperature, this may increase the possibility of identifying binders to a different subset of target entities. Such adaptations to the conditions are within the ambit of the skilled person.

In some embodiments, the specific binding of a candidate antibody to the peptide containing the cryptic epitopes can be determined by surface plasmon resonance (e.g., Biacore system) or Bio-Layer Interferometry (BLI). For surface plasmon resonance, antibodies can be immobilized on sensor chips and the chip exposed to peptides containing a defined epitope. The binding properties of the antibody to the peptide can be measured directly by the change in the local index of refraction upon interaction of the peptide with the antibody. Alternatively, the peptide can be bound to a sensor chip and the chip exposed to the candidate antibody (see, e.g., Rich, R. L. and Myszka, D. G., 2007, Anal Biochem. 361(1):1-6; and Pope et al., 2009, J Immunol Meth. 341(1-2):86-96; incorporated by reference herein). For BLI, the peptide antigen (or antibody) is bound to a biosensor (e.g., fiber optic probe), and the biosensor contacted with a solution containing the antibody (or peptide antigen). The biosensor tip is illuminated with white light, and the changes in interference pattern measured to detect binding. In some embodiments, one or more of other known methods, such as ELISA, FACS, or Western blotting can be used in addition to surface plasmon resonance or BLI to determine appropriate antibody binding potentials and antigenic site-specificities of the antibodies.

In another aspect, the antibodies of the disclosure can be applied to various diagnostic applications. In some embodiments, the antibody can be used to detect the presence and/or levels of sMIC proteins in biological samples, such as those obtained from patients who are suspected of or diagnosed with diseases characterized by elevated MIC protein levels, for example, epithelial cancers, hematologic malignancies, and autoimmune diseases. In some embodiments, the method of detecting sMICA can comprise:
(a) contacting a biological sample with any of the antibody of the disclosure that binds specifically to sMICA; and
(b) determining or measuring the specific binding of the antibody to determine the level of sMICA in the sample.

In some embodiments, the method of detecting sMICB can comprise:

(a) contacting a biological sample with any of the antibody of the disclosure that binds specifically to sMICB; and (b) determining or measuring the specific binding of the antibody to determine the level of sMICB in the sample.

In some embodiments of the diagnostic methods, the antibody can be a cross-reactive antibody that binds specifically to both sMICA and sMICB. Where the biological sample is from a patient suspected or diagnosed with disease or disorder characterized by elevated sMIC levels, the levels of sMICA and/or sMICB detected can be compared to a standard, the standard level being a statistical average of the levels of the sMIC protein in a plurality of subjects without the disease or disorder. As described herein, the level of sMIC detected is abnormal if there is a statistically significant difference from the standard level. In some embodiments, the subject can be examined for sMIC levels over a period of time, including, before diagnosis with a disease or disorder, subsequent to diagnosis of the disease or disorder, prior to treatment with a therapeutic agent, and subsequent to treatment with therapeutic agent. The diagnostic method can be used alone, or in combination with other methods and markers used as a diagnostic for a particular disease or disorder.

In the diagnostic methods, the biological sample can be any suitable sample taken from a subject for analysis, including cell samples, tissue samples and fluid samples. In some embodiments, the fluid sample includes blood, plasma, serum, urine, cerebrospinal fluid, lymph, synovial fluid, bile, semen, saliva, tears, and aqueous or vitreous humor. In some embodiments, the tissue sample includes biopsies of organs, solid tumors, preserved tissues, whole cells, and cell lysates. The biological sample can be prepared by methods known in the art which are suitable for the particular sample, and include, among others, disruption by mechanical means, exposure to freezing (e.g., liquid nitrogen), or by exposure to chemicals, such as detergents, acids, or bases prior to reaction with the antibody. Assays for detecting presence and/or levels of sMIC proteins include those typically used in the art, including among others, immunohistochemistry, competitive and sandwich assays, and steric inhibition assays.

Detecting the specific binding of the antibody (e.g., the antibody-sMIC protein complexes) can rely on use of an antibody containing a reporter molecule or a detectable label, for example, a fluorescent label, detectable enzyme, or a detectable conjugate system. In some embodiments, specific binding of the antibody can rely on a secondary detection agent, such as another antibody that binds specifically to the primary antibody. The secondary antibody can be labeled with a reporter molecule, a detectable label, or a detectable conjugate.

In some embodiments, the diagnostic methods herein can be used to detect levels of sMICA and/or sMICB in biological samples of subjects suspected of having a disease or disorder characterized by elevated MIC levels, which may provide an indicator of the presence of the disease and/or the progression of the disease.

In some embodiments, the diagnostic methods can be used to detect levels of sMICA and/or sMICB in biological samples of a subject already diagnosed with a disease and/or disorder characterized by elevated MIC levels, which may provide confirmation of the presence of the disease and/or the progression of the disease.

In some embodiments, the diagnostic methods can be used to detect levels of sMICA and/or sMICB in subjects who have undergone treatment, to determine the efficacy of the therapeutic agent and/or the therapeutic regimen, and/or the likelihood of disease relapse based on the change in levels of sMICA and/or sMICB.

As noted above, various diseases are associated with elevated or abnormal levels of sMICA and/or sMICB. Although MICA and MICB and its interaction with NKG2D-bearing immune effector cells are involved in immunosurveillance of stressed or diseased cells that culminates in the death of the MIC cells, the presence of soluble MIC proteins downregulates NKG2D receptor levels, enabling MIC tumors to survive in the face of typically competent immune systems. As discussed herein, high levels of sMICA and sMICB have been identified in the blood of cancer patients but not in "normal" individuals, and this has been positively correlated with severity of the cancer staging (Salih et al., 2002, J Immunol 169:4098-102; Doubrovina et al., 2003, J Immunol 171:6891-9; Wu et al., 2004, J Clin Invest. 114:560-8; and Holdenreider, 2006, Intl J Cancer 118:684-7).

Accordingly, in some embodiments, therapeutic antibodies that are designed or selected to bind selectively and specifically to sMICA and/or sMICB when they have been shed or released from the cell (membranes) provides a basis for neutralizing the detrimental effects of sMICA and/sMICB. An advantage of using an antibody that selectively binds to the shed forms of MIC proteins is that the antibodies are unlikely to bind to MIC proteins expressed on surface of cells, thereby decreasing the likelihood of a pathological autoimmune reaction by improper activation of immune effector cells. Similarly, the antibody's absence of significant antagonistic activity against binding of MICA and/or MICB expressed on disease cells to NKG2D receptor levels may preserve the immune mediated destruction of MIC expressing tumor cells. Accordingly, the antibodies of the disclosure can be used in a method of reducing the levels of sMICA and/or sMICB in a subject in need of such treatment (i.e., reduction), where the method comprises:

administering to a subject in need thereof a therapeutically effective amount of an anti-sMICA and/or anti-sMICB antibody described herein.

Generally, the subject to be treated will have elevated levels of sMICA and/or sMICB, where the levels are associated with the presence of a disease or disorder. The term "elevated" or its grammatical equivalents, including "higher," or "greater," etc., when in reference to the level of a molecule (e.g., sMICA and/or sMICB) that is an indicator of a disease or disorder, refers to the quantity of the molecule that is higher in populations with the disease or disorder in a statistically significant manner as compared to the level of the molecule in a population that does not have the disease (e.g., healthy subjects). In some embodiments, the quantity of the sMICA and/or sMICB in the disease population is at least 10% greater than, at least 25% greater than, at least 50% greater than, at least 75% greater than, and/or at least 90% greater than the quantity of the same molecule in the control population that does not have the disease or disorder.

A variety of diseases have been identified that have elevated levels of sMICA and/or sMICB. Such diseases include epithelial cell tumors or cancers, and hematologic malignancies. Thus, in some embodiments, the subject to be treated is afflicted with a MIC tumor or cancer, or a MIC hematologic malignancy. In some embodiments, the MIC tumor or cancer to be treated can be selected from brain cancer, lymphatic cancer, liver cancer, stomach cancer, testicular cancer, cervical cancer, ovarian cancer, vaginal and vulval cancer, leukemia, melanoma, squamous cell carcinoma, malignant mesothelioma cancer, oral cancer, head and neck cancer, throat cancer, thymus cancer, gastrointestinal stromal tumor (GIST) cancer, nasopharyngeal cancer, esophageal cancer, colon cancer, anal cancer, breast cancer, lung cancer, prostate cancer, penile cancer, bladder cancer, pancreatic cancer, neuroblastoma, glioma, hepatocellular carcinoma, and renal cancer. More specifically, it is contemplated for use with cancers involving various types of epithelial tumors, including but not limited to, lung, breast, gastric, colon, ovarian, renal cell, prostate carcinomas and melanoma. Accordingly, in some embodiments, the antibodies of the disclosure can be used to treat a subject afflicted with a MIC tumor or cancer, the method comprising:

administering to a subject afflicted with a MIC tumor or cancer a therapeutically effective amount of an antibody described herein.

In some embodiments, the MIC hematologic malignancy to be treated can be selected from Acute Lymphoblastic Leukemia (ALL), Acute Myelogenous Leukemia (AML), Chronic Lymphocytic Leukemia (CLL), Chronic Myelogenous Leukemia (CML), Acute Monocytic Leukemia (AMol), lymphomas (e.g., Hodgkin's lymphoma and Non-Hodgkin's lymphoma), and Multiple Myelomas. Accordingly, in some embodiments, the antibodies of the disclosure can be used to treat a subject afflicted with a MIC hematologic malignancy, the method comprising:

administering to a subject afflicted with a MIC hematologic malignancy a therapeutically effective amount of an antibody described herein.

In addition to the diseases above, elevated levels of sMICA and/or sMICB occur during certain viral infections. As discussed above, the higher levels of sMICA and/or sMICB present in viral infections appear to prolong and/or increase the severity of the infection by suppression of the immune response by the sMIC proteins. Accordingly, a method of treating a subject with a viral infection characterized by elevated levels of sMIC protein can comprise:

administering to a subject afflicted with a viral infection characterized by elevated levels of sMIC protein a therapeutically effective amount of an antibody of the present disclosure.

Exemplary viral infections that display elevated sMIC protein levels include, among others, infections with hepatitis-B virus (HBV), respiratory syncytial virus (RSV), human cytomegalovirus (HCMV), hepatitis c virus (HCV), and human immunodeficiency virus (HIV). Accordingly, in some embodiments, a method of treating a subject infected with a with hepatitis-B virus (HBV), respiratory syncytial virus (RSV), human cytomegalovirus (HCMV), hepatitis c virus (HCV), or human immunodeficiency virus (HIV: e.g., HIV-1, HIV-2) can comprise:

administering to a subject infected with HBV, RSV, HCMV, HCV or HIV-1 a therapeutically effective amount of an antibody of the present disclosure.

In some embodiments, for any of the treatment methods herein, an exemplary antibody can comprise at least 1, 2, 3, 4, 5 or all 6 of the CDRs in the light chain variable region of amino acid sequence of SEQ ID NO:23 and the heavy chain variable region of amino acid sequence of SEQ ID NO:27. In some embodiments, the antibody for use in the therapeutic treatment comprises at least 1, 2, 3, 4, 5 or all 6 of the CDRs selected from: CDR L1 comprising an amino acid sequence of SEQ ID NO:83; CDR L2 comprising an amino acid sequence of SEQ ID NO:84; CDR L3 comprising an amino acid sequence of SEQ ID NO:85; CDR H1 comprising an amino acid sequence of SEQ ID NO:89, SEQ ID NO:95, or SEQ ID NO:99; CDR H2 comprising an amino acid sequence of SEQ ID NO:90, SEQ ID NO:96, or SEQ ID NO:100; and CDR H3 comprising an amino acid sequence SEQ ID NO:91.

In some embodiments, the antibody for use in the therapeutic treatment comprises at least 1, 2, 3, 4, 5 or all 6 of the CDRs in the light chain variable region of amino acid sequence of SEQ ID NO:31 and the heavy chain variable region of amino acid sequence of SEQ ID NO:35. In some embodiments, the antibody for use in the therapeutic treatment comprises at least 1, 2, 3, 4, 5 or all 6 of the CDRs selected from: CDR L1 comprising an amino acid sequence of SEQ ID NO:86; CDR L2 comprising an amino acid sequence of SEQ ID NO:87; CDR L3 comprising an amino acid sequence of SEQ ID NO:88; CDR H1 comprising an amino acid sequence of SEQ ID NO:92, SEQ ID NO:97, or SEQ ID NO:101; CDR H2 comprising an amino acid sequence of SEQ ID NO:93, SEQ ID NO:98, or SEQ ID NO:102; and CDR H3 comprising an amino acid sequence of SEQ ID NO:94.

In some embodiments, the antibody for use in the therapeutic treatment comprises a light chain variable region VL comprising an amino acid sequence of SEQ ID NO:23 and a heavy chain variable region VH comprising an amino acid sequence of SEQ ID NO:27.

In some embodiments, the antibody for use in the therapeutic treatment comprises a light chain variable region VL comprising an amino acid sequence of SEQ ID NO:31 and a heavy chain variable region VH comprising an amino acid sequence of SEQ ID NO:35.

In some embodiments, the methods disclosed herein are generally useful for generating immune responses, as prophylactic agents, or immune response-stimulating therapeutics. The methods disclosed herein can be applied to a wide range of mammals, including, among others, humans, non-human primates (e.g., chimpanzees, monkeys, etc.), or non-primates (e.g., horses, cattle, pigs, sheep, deer, elk, goats, dogs, cats, rabbits, rats, and mice). Generally, the subject or patient is preferably a human. In certain embodiments, the human is a pediatric patient. In other embodiments, the human is an adult patient. In some embodiments, the subject can be an ape (e.g., gorilla, chimpanzee, or orangutan) or a domesticated mammal (e.g., dog, cat, sheep, cow, or horse).

Any of the compositions described herein, particularly the pharmaceutical compositions, can be administered to the host's body where suitable for administration. The antibody can be delivered to, without limitation, the joints, nasal mucosa, blood, lungs, intestines, muscle tissues, skin, or peritoneal cavity of a mammal. In addition, a composition can be administered by intravenous, intraperitoneal, intramuscular, subcutaneous, intramuscular, intrarectal, intravaginal, intrathecal, intratracheal, intradermal, or transdermal injection, by oral or nasal administration, by inhalation, or by gradual perfusion over time. In a further example, an aerosol preparation of a composition can be given to a host by inhalation. The most suitable route for administration in any given case will depend on the particular antibody, the subject, the nature and severity of the disease, and the physical condition of the subject.

The dosage administered depends on, among others, the route of administration; the nature of the formulation; the nature of the subject's illness; the subject's size, weight, surface area, age, and sex; other drugs being administered; and the judgment of the attending physician. Suitable dosages can be in the range of 0.0001-100 mg/kg body weight. Wide variations in the dosages administered are to be expected in view of the variety of antibody compositions available and the differing efficiencies of various routes of administration. Variations in these dosage levels can be adjusted using standard empirical routines for optimization as is well understood in the art. In some embodiments, for treatment of indications described herein, the effective dose of an antibody of the disclosure can range from about 0.001 to about 75 mg/kg body weight; 0.005 mg/kg to about 50 mg/kg body weight; about 0.01 mg/kg to about 30 mg/kg body weight; or about 0.01 to 5 mg/kg body weight. In some embodiments, the dosages can be about 0.001 mg/kg body weight, about 0.01 mg/kg body weight, about 0.3 mg/kg body weight, about 1 mg/kg body weight, about 3 mg/kg body weight, about 5 mg/kg body weight or about 10 mg/kg body weight, or within the range of 1-10 mg/kg body weight per single (e.g., bolus) administration.

Dosage regimens are adjusted to provide the optimum desired response (e.g., a therapeutic response, manageable toxicity or side effects, etc.). For example, a single bolus may be administered, several divided doses may be administered over time, or the dose may be proportionally reduced or increased as needed by the therapeutic situation. The duration of treatment with any of the compositions provided herein can be any length of time from as short as one day to indefinitely, as needed. The administration can be a single bolus or the administration repeated, e.g., after one day, two days, three days, five days, one week, two weeks, three weeks, one month, five weeks, six weeks, seven weeks, two months, three months, or more. The repeated administration can be at the same dose or at a different dose. For example, a defined dosage regimen is continued for period of time, for example, 2 weeks to 6 months, from 3 months to 1 or 2 years, from 6 months to 3 or 4 years, from 8 months to 18 months, or the like, as necessary to treat the disease (e g, eliminate the disease, cause remission, or halt disease progression). In some embodiments, the initial treatment can be a defined dosage regimen 2 weeks to 2 months, followed by a maintenance dosage regimen, where the maintenance dosage can be the same or lower dose than the initial treatment, repeated as necessary to treat the disease or disorder, for example, a maintenance treatment of once every two weeks, once a month, once every two months, or once every four months, or on an as needed basis as determined by a physician.

In some embodiments, the antibodies can be used as monotherapy, and can be administered as a single dose or several doses over time. In some embodiments, the antibody can be administered as induction therapy, i.e., the first in a series of therapeutic measures used to treat a disease, followed by maintenance therapy with the antibody.

In some embodiments, the antibodies can be used in combination with other therapeutic agents suitable for treating the disease or disorder characterized by elevated levels of sMIC protein. In the combination therapy, the antibody of the disclosure and one or more of the combination therapeutic agent can be administered concurrently (e.g., simultaneously), sequentially, together, or separately.

In some embodiments, the antibodies of the disclosure are used in combination with chemotherapeutic agents used to treat tumors, cancers or autoimmune diseases. The chemotherapeutic agents can include, among others, cytotoxic agents, anti-metabolite agents (e.g., folate antagonists, purine analogs, pyrimidine analogs, etc.), topoisomerase inhibitors (e.g., camptothecin derivatives, anthracenedione, anthracyclines, epipodophyllotoxins, quinoline alkaloids, etc.), anti-microtubule agents (e.g., taxanes, vinca alkaloids), protein synthesis inhibitors (e.g., cephalotaxine, camptothecin derivatives, quinoline alkaloids), alkylating agents (e.g., alkyl sulfonates, ethylenimines, nitrogen mustards, nitrosoureas, platinum derivatives, triazenes, etc.), alkaloids, terpenoids, and kinase inhibitors. Exemplary chemotherapeutic agents typically used to treat proliferative disorders, such as cancers and tumors, include, by way of example and not limitation, afatinib, afuresertib, alectinib, alisertib, alvocidib, amonafide, amuvatinib, axitinib, azacitidine, azathioprine, bafetinib, barasertib, bendamustine, bleomycin, bosutinib, bortezomib, busulfan, cabozantinib, camptothecin, canertinib, capecitabine, cabazitaxel, carboplatin, carmustine, cenisertib, ceritinib, chlorambucil, cisplatin, cladribine, clofarabine, crenolanib, crizotinib, cyclophosphamide, cytarabine, dabrafenib, dacarbazine, dacomitinib, dactinomycin, danusertib, dasatinib, daunorubicin, decitabine, dinaciclib, docetaxel, dovitinib, doxorubicin, epirubicin, epitinib, eribulin mesylate, errlotinib, etirinotecan, etoposide, everolimus, exemestane, floxuridine, fludarabine, fluorouracil, gefitinib, gemcitabine, hydroxyurea, ibrutinib, icotinib, idarubicin, ifosfamide, imatinib, imetelstat, ipatasertib, irinotecan, ixabepilone, lapatinib, lenalidomide, lestaurtinib, lomustine, lucitanib, masitinib, melphalan, mercaptopurine, methotrexate, midostaurin, mitomycin, mitoxantrone, mubritinib, nelarabine, neratinib, nilotinib, nintedanib, omacetaxine mepesuccinate, orantinib, oxaliplatin, paclitaxel, palbociclib, palifosfamide tris, pazopanib, pelitinib, pemetrexed, pentostatin, plicamycin, ponatinib, poziotinib, pralatrexate, procarbazine, quizartinib, raltitrexed, regorafenib, ruxolitinib, seliciclib, sorafenib, streptozocin, sulfatinib, sunitinib, tamoxifen, tandutinib, temozolomide, temsirolimus, teniposide, theliatinib, thioguanine, thiotepa, topotecan, valrubicin, vandetanib, vemurafenib (Zelbora®), vincristine, vinblastine, vinorelbine, vindesine, and the like. In some embodiments, a chemotherapeutic agent can be chosen that does not adversely affect the subject's immune response.

In some embodiments, the antibodies can be used in combination with a biologic drug used to treat tumors, cancers or autoimmune diseases. Exemplary biologic drugs that can be used in combination with the antibodies herein include, among others, anti-BAFF (e.g., belimumab); anti-CCR4 (e.g., mogamulizumab); anti-CD19/CD3 (e.g., blinatumomab); anti-CD20 (e.g., obinutuzumab, rituximab, ibritumomab tiuxetan, ofatumumab, tositumomab); anti-CD22 (e.g., moxetumomab pasudotox); anti-CD30 (e.g., brentuximab vedotin); anti-CD33 (e.g., gemtuzumab); anti-CD37 (e.g., otlertuzumab); anti-CD38 (e.g., daratumumab); anti-CD52 (e.g., alemtuzumab); anti-CD56 (e.g., lorvotuzumab mertansine); anti-CD74 (e.g., milatuzumab); anti-CD105; anti-CD248 (TEM1) (e.g., ontuxizumab); anti-CTLA4 (e.g., tremelimumab, ipilimumab); anti-EGFL7 (e.g., parsatuzumab); anti-EGFR (HER1/ERBB1) (e.g., panitumumab, nimotuzumab, necitumumab, cetuximab, imgatuzumab, futuximab); anti-FZD7 (e.g., vantictumab); anti-HER2 (ERBB2/neu) (e.g., margetuximab, pertuzumab, ado-trastuzumab emtansine, trastuzumab); anti-HER3 (ERBB3); anti-HGF (e.g., rilotumumab, ficlatuzumab); anti-IGF-1R (e.g., ganitumab, figitumumab, cixutumumab, dalotuzumab); anti-IGF-2R; anti-KIR (e.g., lirilumab, onartuzumab); anti-MMP9; anti-PD-1 (e.g., nivolumab, pidilizumab, lambrolizumab); anti-PD-L1; anti-PDGFRa (e.g., ramucirumab, tovetumab); anti-PD-L2; anti-PlGF (e.g., ziv-aflibercept); anti-RANKL (e.g., denosumab); anti-TNFRSF9 (CD137/4-1 BB) (e.g., urelumab); anti-TRAIL-R1/DR4, R2/D5 (e.g., dulanermin); anti-TRAIL-R1/D4 (e.g., mapatumumab); anti-TRAIL-R2/D5 (e.g., conatumumab, lexatumumab, apomab); anti-VEGFA (e.g., bevacizumab, ziv-aflibercept); anti-VEGFB (e.g., ziv-aflibercept); and anti-VEGFR2 (e.g., ramucirumab).

In particular, the antibody described herein can be used in combination with therapeutic agents that activate, e.g., stimulate, the immune system. In some embodiments, these can comprise agents that positively activate the immune system, or agents that inhibit downregulation of immune activation. The immuno-activating or immune stimulating agents can be small molecule compounds, antibodies, antisense compounds, gene therapy, and the like. Various biological targets for therapeutic immune activation agents include, by way of example and not limitation, CTLA-4, KIR (Killer-cell immunoglobulin-like receptor), PD-1, PD-L1, PD-L2, CD137, CD227, IL-15 receptor, IL-6, IL-6 receptor, TGF-β1, TGF-β2, TGF-β3, and apolipoprotein J (Clusterin). In some embodiments, the immune system activating agent includes antibodies or other binding agents directed against the therapeutic targets, for example, anti-CTLA4, anti-PD-1, anti-PD-L1, anti-PD-L2, anti-CD137, anti-TGF-β1, anti-TGF-β2, anti-TGF-β3, and anti-apolipoprotein J (Clusterin). Exemplary immune activating agents include, among others, ipilimumab, tremelimumab (Ribas et al, 2013, J Clin Oncol. 31:616-22), nivolumab (Wolchok et al., 2013, N Engl J Med. 369:122-33), BMS-936559 (MDX-1105: Brahmer et al, 2012, N Engl J Med. 366:2455-65), MEDI4736 (anti-PD-L1), MPDL3280A (anti-PDL-1), lambrolizumab (Hamid et al., 2013, N Engl J Med. 369:134-44), pidilizumab (anti-PD-1; Berger R et al 2008, Clin Can Res. 14:3044-51), AMP-224 (PD-L2-Ig), lambrolizumab, urelumab (Li and Liu, 2013, Clin Pharm: Advances & Application 5(Suppl 1):47-53), PF-05082566 (Fisher et al., 2012, Canc Immunol Immunother. 61:1721-33), ALT-803 (IL-15 agonist; Xu et al, 2013, Canc Res. 73:3075-86; Zhu et al, 2009, J Immunol 183:3598-607), AB-16B5 (anti-Clusterin), pirfenidone (Noble et al., 2011, Lancet 377:1760-9), fresolimumab (Trachtman et al., Kidney Int. 79:1236-43), sultiximab, and tocilizumab.

In some embodiments, the immune activating agent for use in combination with the antibodies can comprise a cytokine or chemokine that stimulates the immune response. Exemplary cytokines and chemokines include, among others, IL-2, IL-7, IL-12, IL-15, IL-21, GM-CSF, IFN-α, and CCL-21. In some embodiments, the immune stimulating cytokines and chemokines can be used ex vivo to treat immune cells, particularly immune cells obtained from the subject or patient to be treated.

In some embodiments, the antibody described herein can be used in combination with cancer vaccines, which includes antigen presenting cells (e.g., dendritic cells) activated with cancer vaccines. Exemplary cancer vaccines include, among others, prostatic acid phosphatase (e.g., Provenge®); gp-96-Ig (e.g., HS-410); PANVAC; HER2/neu (e.g., nelipepimut-S, AVX901); DCVax(R)-L; rindopepimut; IMA950 (multi tumor associated peptides); tumor-derived heat shock protein gp96 (Vitespen); surviving peptide (e.g., ISA-51: US patent publication 20110091489); EGFRvIII-NY-ESO-1 (e.g., ADU-623); CD-133; folate binding protein vaccines E39 and J65; HLA-A2 tumor antigen peptides; carcinoembryonic antigen (CEA); universal tumor antigen oncofetal antigen/immature laminin receptor protein (OFA/iLRP); mammaglobin-A; bi-shRNAfurin; HLA-A*2402 restricted epitope peptides CDCA1, URLC10, KIF20A, DEPDC1 and MPHOSPH1; hyperglocosylated MUC1 (e.g., ONT-10); poly-ICLC; human telomerase reverse transcriptase (e.g., hTERT, UV1, GV1001); HPV P16 37-63-peptide; HPV-16-E7 (e.g., ADX11-001), pNGVL4a-Sig; Herpes Zoster vaccine GSK1437173A; NY-ESO-1 antigen; leukemia-associated antigen WT1; bcr-abl p210-b3a2 breakpoint-derived pentapeptide CMLVAX100; lung cancer cell with GM-CSF (e.g., GVAX); Wilms tumor gene 1 (WT1) peptide (e.g., OCV-501); human MUC1 antigen (e.g., L-BLP25); MUC1 peptide tecemotide; HLA-A*0201 restricted epitope peptide URLC10, VEGFR1 and/or VEGFR2 9URLC10; cancer-testis antigens (e.g., URLC10, CDCA1, KIF20A, MAGE-C1, MAGE-A3/6, etc.); autophagosome-enriched vaccine Dribble, L523S protein; RNActive derived lung cancer vaccine CV9202; CSF-470 vaccine; melanoma antigen MAGE-3.A1; melanoma antigen NA17.A2; melanoma antigen IMP321; melanoma antigen LAG-3; IBBL antigen (e.g., A2/4-1BBL) melanoma vaccine; MART-1; gp100 (e.g., g209-2M, G280-9V); KRN7000; PVX-410; PROSTVAC; peptide pyroEH-WSYGLRPG (PEP223); prostate specific antigen; and PSMA antigen (e.g., BPX-201).

In some embodiments, the cancer vaccine used in combination with the antibodies can be tumor cells or tumor cell lysates, which vaccines include antigen presenting cells (e.g., dendritic cells) activated with tumor cells or tumor cell lysates. Exemplary tumor cells and corresponding tumor cells lysates useful as vaccines include, among others, bladder cancer cells, glioblastoma cells, breast cancer cells, cervical cancer cells, lymphoma cells, kidney cancer cells, leukemic cells, lung cancer cells, melanoma cells, multiple myeloma cells, non-Hodgkin's lymphomas, pancreatic cancer cells, and prostate cancer cells.

In some embodiments, the antibodies can be used in combination with antiviral drugs used to treat viral infections characterized by presence of elevated sMIC ligands, for example, infections with hepatitis-B virus, respiratory syncytial virus, human cytomegalovirus, hepatitis c virus, and human immunodeficiency virus. Drugs for treating hepatitis-B viral infections include, among others, interferons (e.g., interferon alpha-2b or pegylated interferon), lamivudine, adefovir dipivoxil, entecavir, telbivudine, and tenofovir. Drugs for treating respiratory syncytial virus include, among others, RSV hyperimmune globulin; palivizumab; benzimidazoles BMS-433771, TMC353121 and JNJ-2408068; ribavirin; and antisense phosphorodiamidate morpholino oligomers (see review Olszewska and Openshaw, 2009, Expert Opin Emerg Drugs 14(2): 207-17). Drugs for treating hepatitis C virus include, among others, interferons (e.g., interferon alpha-2b or pegylated interferon), boceprevir, telaprevir, ribavirin, simeprevir, sofosbuvir, daclatasvir, and combinations thereof. Drugs for treating human immunodeficiency virus include, among others, efavirenz, emtricitabine, tenofovir disoproxil fumarate, rilpivirine, cobicistat, lamivudine, zidovudine, abacavir, zalcitabine, stavudine, nevirapine, etravirine, delavirdine, tipranavir, indinavir, saquinavir mesylate, lopinavir, ritonavir, darunavir, atazanavir sulfate, nelfinavir mesylate, maraviroc, raltegravir, enfuvirtide, and combinations thereof.

In some embodiments of the combination therapy, the antibody described herein can be used prior to, concurrently with, or subsequent to the administration of the other therapeutic agent. In some embodiments, the antibody of the disclosure and the combination therapeutic agent can be administered successively to the patient on the same day, for example during the same patient visit. Successive administration can occur 1, 2, 3, 4, 5, 6, 7 or 8 hours or more hours apart. In some embodiments, the antibody of the disclosure and the combination therapeutic agent can be administered separately, e.g., on different days, for example, the antibody and the combination therapeutic agent can be administered at a 1-day, 2-day or 3-day, one-week, 2-week or monthly intervals. Other treatment regimens for the combination of the antibody of the disclosure and other therapeutic agents will be apparent to the skilled artisan in light of the guidance herein.

In another aspect, the present disclosure provides articles of manufacture and kits containing materials useful for practicing the antibodies and methods described herein. In some embodiments, the article can comprise a container comprising the antibodies of the present disclosure. Suitable containers include, among others, bottles, vials, bags, and syringes. The containers can be made of various materials, such as plastic or glass. In some embodiments, the containers can have a sterile access port, for example, a stopper or membrane for inserting a hypodermic injection needle.

In some embodiments, the articles can also include at least a second container containing materials to be used in combination with the antibodies, such as sterile water or sterile buffer, for example for reconstituting the compositions for use. In some embodiments, the second container or a third container can comprise an additional therapeutic agent, including, a chemotherapeutic agent or biological agent for use in combination with the antibody compositions of the present disclosure.

In some embodiments, the article comprises a label or package insert that describes the composition used for treating one or more disease conditions. The articles can also include instructions or descriptions of the compositions and instructions for their use on a suitable electronic medium, such as optical discs and static random access memory chips.

The articles of manufacture can be provided in the form of kits comprising the containers, package inserts, and/or electronic medium. It may further include other materials desirable for commercial distribution and the user, such as other buffers, diluents, filters, needles and syringes.

Having now generally described the invention, the same will be more readily understood through reference to the following examples which are provided by way of illustration, and are not intended to be limiting of the present invention, unless specified.

EXAMPLES

Example 1: Methods Related to Generation of Monoclonal Antibodies to the Alpha-3 Domain of MICA Production of Extracellular Alpha-3 Domain MICA Immunogen by Baculovirus Expression.

To prepare the extracellular alpha-3 domain of MICA as an immunogen for antibody production, a Baculovirus protein expression system was used to generate the appropriate protein glycosylation on expressed MICA. Recombinant alpha-3 domain MICA cDNA (allele 001) corresponding to the GenBank MICA sequence NP_000238.1 (FIG. 1) encoding residues 205 to 297 of the alpha-3 domain of MICA (FIG. 1C: SEQ ID NO:3), which are amino acid residues 182 to 274 of the processed MICA protein (e.g., FIG. 4-A), was synthetically generated along with convenient restriction enzymes sites for further subcloning into the Baculovirus transfer vector, and then ligated into an appropriate DNA cloning vector. The Baculovirus transfer vector contained a six C-terminal Histidine residue tag for purification. Exemplary MICA peptide immunogens with purification tags and cleavage sites can also be selected from the following, where the MICA sequences are underlined:

(a)
(SEQ ID NO: 73)
MEFVPPMVNVTRSEASEGNITVTCRASGFYPWNITLSWRQDGVSLSHDT
QQWGDVLPDGNGTYQTWVATRICQGEEQRFTCYMEHSGNHSTHPVPSEN
LYFQGHHHHHH;

(b)
(SEQ ID NO: 74)
MEFTWVATRICQGEEQRFTCYMEHSGNHSTH PVPSENLYFQGHHHHHH;

(c)
(SEQ ID NO: 75)
MEFRSEASEGNITVTCRASGFYPWNITLSWRQDGVSLSHDTQQWGDVLP
DGNGTYQTWVATRICQGEEQRFTCYMEHSGNHSTHPVPSENLYFQGHHH
HHH;

(d)
(SEQ ID NO: 76)
MEFRSEASEGNITVTCRASGFYPWNITLSWRQDGVSLSHDTQQWGDVLP
DGNGTYQTWVATRICQGEEQRFTCYMEHSGNHSTHENLYFQGHHHHHH;
and (e)
(SEQ ID NO:77)
MEFRSEASEGNITVTCRASGFYPWNITLSWRQDGVSLSHDTQQWGDVLP
DGNGTYQTWVATRICQGEEQRENLYFQGHHHHHH.

Upon confirmation of both the MICA and the additional DNA sequences in the subclone, a Baculovirus expression system was used to recombine the two DNA components in E. coli bacteria to generate a bacmid construct containing the recombinant viral DNA. A recombinant bacmid clone with the correct sequence was used to produce recombinant Baculovirus by transfection into Sf9 insect cells.

In order to produce recombinant protein, Sf9 cells were infected with recombinant virus in serum-free medium, such as SF-900 (Life Technologies), and the cells harvested at day 4 or 5 after infection. To purify the MICA alpha-3 domain polypeptide from the infected cells, the cells were lysed, centrifuged briefly to collect the supernatant, and then subjected to affinity chromatography using $Ni^{2+}$ chelation. Protein recovery was improved by the addition of 8M urea to the sample buffer prior to chromatography. Dialysis against a carbonate buffer was used to remove the urea. The pure protein may also be concentrated by centrifugation filters (Amicon) to achieve a more stable protein preparation.

In another embodiment, a similar strategy can be taken to prepare the alpha-3 domain from MICB as the recombinant protein to be used in immunization of mice (sequence presented in FIG. 1D: SEQ ID NO:4). Exemplary MICB peptide immunogens with purification tags and cleavage sites can also be selected from the following, where the MICB sequences are underlined:

(a)
(SEQ ID NO: 78)
MEFVPPMVNVTCSEVSEGNITVTCRASSFYPRNITLTWRQDGVSLSHNT
QQWGDVLPDGNGTYQTWVATRIRQGEEQRFTCYMEHSGNHGTHPVPSEN
LYFQGHHHHHH;

(b)
(SEQ ID NO: 79)
MEFTWVATRIRQGEEQRFTCYMEHSGNHGTHPVPSENLYFQGHHHHHH;

(c)
(SEQ ID NO: 80)
MEFCSEVSEGNITVTCRASSFYPRNITLTWRQDGVSLSHNTQQWGDVLP
DGNGTYQTWVATRIRQGEEQRFTCYMEHSGNHGTHPVPSENLYFQGHHH
HHH;

-continued (d)

(SEQ ID NO: 81)
MEFCSEVSEGNITVTCRASSFYPRNITLTWRQDGVSLSHNTQQWGDVLP
DGNGTYQTWVATRIRQGEEQRFTCYMEHSGNHGTHENLYFQGHHHHHH;
and (e)

(SEQ ID NO: 82)
MEFCSEVSEGNITVTCRASSFYPRNITLTWRQDGVSLSHNTQQWGDVLP
DGNGTYQTWVATRIRQGEEQRENLYFQGHHHHHH.

Monoclonal Antibody Generation and Primary Screening.

The alpha-3 domain MICA immunogen was prepared in an aqueous solution (about 0.5 mg/ml) and injected five times, over a two-week period, into immunocompetent mice using a RapidPrime™ method (ImmunoPrecise, British Columbia, Canada). Following immunization, the lymphocytes from the lymph tissue of the immunized mice were removed and the lymphocytes chemically fused with, but not limited to, polyethylene glycol (PEG) or a PEG derivative, to murine SP2/O myeloma cells for immortalization. The fused cells were grown in a methylcellulose-containing semi-solid HAT drug-selection medium in order to select clonal B-cell/myeloma fusion hybridoma cells capable of producing antibodies. The primary screening of hybridoma clones involved testing antibody-containing supernatants for their ability to bind recombinant antigen (alpha-3 domain of MICA) by ELISA. The primary screen produced 146 hits from a total of 948 (15%) hybridoma clones assayed, while the isotyping assay identified 98/146 clones (67%) for a specific antibody type, equivalent to 10% of the 948 initial clones.

Secondary Screening Using Indirect ELISA.

Several secondary indirect ELISA screens were performed to help select high quality hybridoma clones for further analysis. Hybridoma supernatant containing antibody were assessed for binding to: (a) test alpha-3 domain MICA protein; (b) a His-tagged protein with no relation to MIC proteins to rule out potential His tag binding antibodies; (c) recombinant E. coli-produced ectodomain protein from human MICA (including complete alpha-3 subdomain, but without a His-tag) (Bio Basic, Markham, Canada); and (d) recombinant E. coli-produced ectodomain protein from human MICB (including complete alpha-3 subdomain, but without a His-tag) (Bio Basic, Markham, Canada).

The proteins above were bound to an ELISA plate overnight at 4'C at a concentration ranging from 0.1 to 0.2 µg per well in carbonate buffer (pH 9.6). The plates were then blocked with skim milk powder/PBS pH 7.4, washed and then treated for 1 hour with primary antibody (100 µl of hybridoma supernatant) or with positive control MIC murine monoclonal antibodies (BAMO3, a MIC alpha-3 specific IgG$_{2a}$ mAb; and BAMO1, a MIC alpha 1+2 specific IgG$_1$ mAb; both from MBL International, MA, USA) or with isotype-matched negative control antibodies. After washing, the wells were treated with secondary goat anti-mouse IgG/IgM (H+L)-HRP conjugated antibody for 1 hour. HRP substrate, tetramethylbenzidine (TMB), was added to the washed wells, and the color was developed for 5 minutes in the dark. The reactions were stopped by the addition of 1M HCl, and the plates were read at 450 nm.

These ELISA experiments resulted in only a minor number of hybridoma supernatants reacting very weakly with the His-tagged protein, suggesting that the antibodies generated were target, i.e., MICA, specific. We also determined that many of the hybridomas tested produced antibodies that bound strongly to both the alpha-3 target MICA protein as well as to the bacterially-produced MICA and/or MICB proteins, enabling the collection of different clones with varying binding capabilities. Of particular interest were the clones that produced antibodies, which included clones 1F5 and 8C7, capable of binding the target MICA alpha-3 domain recombinant protein as well as the MICA and MICB recombinant ectodomain proteins. The ELISA experiments also indicated, retrospectively, that control MIC antibody BAMO3 (MIC alpha-3 specific), but not BAMO1 (MIC alpha 1+2 specific), was capable of producing strong signal by indirect ELISA against the recombinant alpha-3 MICA target protein, confirming that the test alpha-3 domain antigen was indeed correctly expressed in the Baculovirus system.

Secondary Screen Using Flow Cytometry Assay.

A secondary screen used the same antibody-containing supernatants to test for their ability to bind recombinant extracellular regions (alpha-1, -2 and -3 domains) of MICA or MICB proteins by indirect ELISA, and for their inability to bind MIC proteins on the cell surface of MIC expressing heat-shocked HCT116 colon carcinoma cells by flow cytometric analysis.

To assay for binding to cell bound MIC protein, MIC expressing heat-shocked HCT116 colon carcinoma cells were heat-treated at 42° C. for 60 min and then allowed to recover for 22 hr at 37° C. Upon recovery, a viability test was performed on post-trypsinized cells, and a viability level of 97% was determined Heat-treated HCT116 cells were then prepared for flow cytometry by first blocking briefly with Clear Back™ human Fc receptor blocking reagent (MBL International, MA, USA), and then treating with primary antibody which was selected from one of the following: (a) test hybridoma supernatant; (b) positive control murine antibodies capable of binding either to the alpha-1 plus alpha-2 MIC subdomains only, or to the alpha-3 MIC subdomain only (BAMO1 and BAMO3 mABs described above: MBL International, MA, USA), or (c) negative control murine antibodies isotype-matched to the positive control antibodies (IgG$_1$ anti-human transferrin antibody and IgG$_{2a}$—anti-trout Ig). After incubation and extensive washing, the cells were treated with phycoerythrin (PE) conjugated goat anti-mouse secondary antibody (Jackson Immuno Research, PA, USA). Cells were then fixed with BD Cytofix™ (BD Biosciences, CA, USA), re-suspended in preservative buffer, and then subjected to flow cytometry on a GuavaFlow FACS machine.

Strong binding to the cell surface was detected with both positive control antibodies (alpha-1+2 specific, or alpha-3 specific), but no binding was observed with either negative control antibodies (not shown) or with hybridoma test supernatants whose antibodies had previously been determined to bind to the MICA alpha-3 subdomain recombinant protein in ELISA assay format. Specifically, antibodies from hybridoma clones 1F5 (IgG$_1$) and 8C7 (IgG$_1$) were incapable of binding to the cell-surface expressed MIC proteins on HCT116 cells (FIG. 9). These two hybridoma clones IF5 and 8C7 were further characterized.

Example 2: Characterization of 1F5 and 8C7 Antibodies

Analysis of Binding Affinity.

Biomolecular interactions between antigen and antibody were directly measured by Bio-Layer Interferometry (BLI) using a Pall ForteBio Octet RED96 machine (Pall ForteBio, CA, USA). Real-time kinetic analyses were performed on the test MICA monoclonal antibodies 1F5 and 8C7, as well as two control antibodies, one of which could bind the alpha-3 MICA subdomain antigen (positive control) and one of which could not (negative control, binds other MICA subdomains), as previously determined by ELISA. The Octet RED96 apparatus operates under the principle of Bio-Layer Interferometry, a label-free technique that measures molecular interactions and complex formation. A key component of the technique is the optical biosensor whose tip is immersed in the fluids of the test well and then used to assay interference patterns between waves of light. Here, the ligand (monoclonal antibody) is localized to the surface of the biosensor through capture by previously bound anti-mouse IgG, while the analyte biomolecule (antigen) is kept in solution. Binding responses between ligand and analyte were measured and reported in real-time. Both association and dissociation kinetics were monitored and $K_D$ values were calculated. This model assumed a 1:1 interaction of ligand to analyte.

At pH 7.4, the affinity constant $K_D$ for the positive control MICA antibody was about $6.07 \times 10^{-9}$ M. The negative control MICA antibody that does not bind tightly had a $K_D$ of about $9.6 \times 10^{-6}$ M. For the two MICA monoclonal antibodies, antibody from clone 1F5 had a measured $K_D$ of about $7.83 \times 10^{-10}$ M while the antibody from clone 8C7 had a measured $K_D$ of about $6.81 \times 10^{-09}$ M.

Sequencing of Antigen Binding Domains. Hybridoma cells were lysed with detergent-containing buffer, and mRNA was isolated by standard procedures. RT-PCR was carried out using 5' RACE (RLM-RACE) and gene specific reverse primers, which amplify mouse immunoglobulin heavy chain ($IgG_1$) and light chain (kappa) variable region sequences. The reaction mixture was separated by gel electrophoresis, and the specific PCR bands were gel-excised. The purified PCR product was cloned into pCR-Blunt II-TOPO vector, and the constructs transformed into *E. coli*. Twenty three colonies of each chain were picked and PCR screened for the presence of amplified regions prior to sequencing. PCR positive clones (about 8 to 10) for each chain were sequenced. DNA sequences were analyzed by BLAST to confirm homology to mouse antibody sequences. Sequences of the variable regions of antibody 1F5 are depicted in FIG. 6 (A-H). Sequences of the variable regions of antibody 8C7 are depicted in FIG. 7 (A-H).

The foregoing descriptions of specific embodiments of the present invention have been presented for purposes of illustration and description. They are not intended to be exhaustive or to limit the invention to the precise forms disclosed, and many modifications and variations are possible in light of the above teaching.

All patents, patent applications, publications, and references cited herein are expressly incorporated by reference to the same extent as if each individual publication or patent application was specifically and individually indicated to be incorporated by reference.

What is claimed is:

1. An isolated antibody having a CDR L1 consisting of the amino acid sequence RSSKSLLQSNGNTFLY (SEQ ID NO:86); a CDR L2 consisting of the amino acid sequence RMSNLAS (SEQ ID NO:87); a CDR L3 consisting of the amino acid sequence MQHLEYPFT (SEQ ID NO:88); a CDR H1 consisting of an amino acid sequence NYGMN (SEQ ID NO:92), a CDR H2 consisting of the amino acid sequence WINTNTGEPTYAEEFKG (SEQ ID NO:93); and a CDR H3 consisting of the amino acid sequence SGGSSP-FAY (SEQ ID NO:94), wherein the antibody specifically binds soluble MICA or soluble MICB.

2. The isolated antibody of claim 1, comprising a light chain variable region (VL) consisting of the amino acid sequence of SEQ ID NO: 31 and a heavy chain variable region (VH) consisting of the amino acid sequence of SEQ ID NO: 35.

3. A pharmaceutical composition comprising an isolated antibody of claim 1 or 2, and a pharmaceutically acceptable carrier.

* * * * *